(12) United States Patent
Tamai et al.

(10) Patent No.: US 10,550,165 B2
(45) Date of Patent: Feb. 4, 2020

(54) PEPTIDE FOR INDUCING REGENERATION OF TISSUE AND USE THEREOF

(71) Applicants: STEMRIM INC., Osaka (JP); OSAKA UNIVERSITY, Osaka (JP)

(72) Inventors: Katsuto Tamai, Osaka (JP); Takehiko Yamazaki, Osaka (JP); Tsutomu Kanezaki, Osaka (JP); Shigeru Sakurai, Osaka (JP); Yukiko Noguchi, Osaka (JP); Mayumi Endo, Osaka (JP); Natsumi Hamabuchi, Osaka (JP); Kana Naito, Osaka (JP)

(73) Assignees: STEMRIM INC., Osaka (JP); OSAKA UNIVERSITY, Osaka (JP)

(*) Notice: Subject to any disclaimer, the term of this patent is extended or adjusted under 35 U.S.C. 154(b) by 0 days.

(21) Appl. No.: 15/691,017

(22) Filed: Aug. 30, 2017

(65) Prior Publication Data
US 2018/0072785 A1   Mar. 15, 2018

Related U.S. Application Data

(63) Continuation of application No. 14/114,395, filed as application No. PCT/JP2012/059113 on Apr. 3, 2012.

(30) Foreign Application Priority Data

Apr. 26, 2011  (JP) ................. 2011-098270
Oct. 3, 2011   (JP) ................. 2011-219454

(51) Int. Cl.
| | | |
|---|---|---|
| A61K 38/00 | (2006.01) | |
| C07K 14/00 | (2006.01) | |
| C07K 14/47 | (2006.01) | |
| A61K 38/17 | (2006.01) | |

(52) U.S. Cl.
CPC ...... *C07K 14/4705* (2013.01); *C07K 14/4702* (2013.01); *A61K 38/17* (2013.01)

(58) Field of Classification Search
None
See application file for complete search history.

(56) References Cited

U.S. PATENT DOCUMENTS

| | | | |
|---|---|---|---|
| 3,896,810 A | 7/1975 | Kkiyama | |
| 4,732,155 A | 3/1988 | Zetter et al. | |
| 5,661,127 A | 8/1997 | Bhatnagar et al. | |
| 5,851,986 A | 12/1998 | Takada et al. | |
| 5,902,799 A | 5/1999 | Herrmann et al. | |
| 7,220,723 B2* | 5/2007 | Tracey ............... | C07K 14/4702 514/16.7 |
| 7,288,250 B2* | 10/2007 | Newman ............ | C07K 14/4718 424/133.1 |
| 7,585,504 B2* | 9/2009 | Wu ...................... | C07K 16/24 424/142.1 |
| 8,673,580 B2 | 3/2014 | Tamai et al. | |
| 2002/0058019 A1 | 5/2002 | Berenson et al. | |
| 2003/0003482 A1 | 1/2003 | Halle et al. | |
| 2003/0060410 A1 | 3/2003 | Tracey et al. | |
| 2004/0031072 A1 | 2/2004 | La Rosa et al. | |
| 2004/0053841 A1 | 3/2004 | Tracey et al. | |
| 2004/0156851 A1 | 8/2004 | Newman | |
| 2004/0191246 A1 | 9/2004 | Connelly et al. | |
| 2004/0249448 A1 | 12/2004 | Gault | |
| 2004/0265971 A1 | 12/2004 | Sato et al. | |
| 2005/0014255 A1 | 1/2005 | Tang et al. | |
| 2005/0260174 A1 | 11/2005 | Fraser et al. | |
| 2006/0035851 A1 | 2/2006 | Bianchi et al. | |
| 2006/0039896 A1 | 2/2006 | Kleinsek et al. | |
| 2006/0111287 A1 | 5/2006 | Bianchi | |
| 2006/0127373 A1 | 6/2006 | Son et al. | |
| 2006/0281674 A1 | 12/2006 | Tessier et al. | |
| 2007/0154529 A1 | 7/2007 | Bullerdiek et al. | |
| 2007/0238663 A1 | 10/2007 | Capogrossi et al. | |

(Continued)

FOREIGN PATENT DOCUMENTS

| | | |
|---|---|---|
| AU | 2003228099 A1 | 1/2004 |
| AU | 2004203732 A1 | 7/2004 |

(Continued)

OTHER PUBLICATIONS

Ryckman, C. et al., "Proinflammatory Activities of S100: Proteins S100A8, S100A9, and S100A8/A9 Induce Neutrophil Chemotaxis and Adhesion," Journal of Immunology, 2003, 170(6): 3233-3242.
Santamaria-Kiseil, L. et al., "Calcium-dependent and -independent interactions of the S100 protein family," Biochem J., 2006, 396: 201-214.
Sasaki, M. et al., "Mesenchymal Stem Cells Are Recruited into Wounded Skin and Contribute to Wound Repair by Transdifferentiation into Multiple Skin Cell Type," Journal of Immunology, 2008, 180(4): 2581-2587.
Schäffer, M.R. et al., "Wound Fluid Inhibits Wound Fibroblast Nitric Oxide Synthesis," Journal of Surgical Research, 2004, 122(1): 43-48.
Schön et al., "Psoriasis," The New England Journal of Medicine, May 5, 2005, 352(18): 1899-1912.

(Continued)

*Primary Examiner* — Michail A Belyavskyi
(74) *Attorney, Agent, or Firm* — Saliwanchik, Lloyd & Eisenschenk

(57) ABSTRACT

(Objective) An objective of the present invention is to provide therapeutic agents that, in association with stimulation of PDGFRα-positive cells such as bone marrow mesenchymal stem cells, promote their mobilization into blood and accumulation in a damaged tissue, and induce tissue regeneration in a living body.
(Means for solution) Multiple peptides were synthesized, and the migration-promoting activity of each peptide was evaluated. As a result, the present inventors successfully identified multiple peptides that have migration-promoting activity on a PDGFRα-positive bone marrow mesenchymal stem cell line (MSC-1). Further, the present inventors confirmed that the identified peptides also have migration-promoting activity on skin fibroblasts, which are PDGFRα-positive cells.

13 Claims, 29 Drawing Sheets

Specification includes a Sequence Listing.

(56) References Cited

U.S. PATENT DOCUMENTS

| | | |
|---|---|---|
| 2008/0214454 A1 | 9/2008 | Tracey et al. |
| 2008/0286324 A1 | 11/2008 | Stolen et al. |
| 2009/0053277 A1 | 2/2009 | Nagaya et al. |
| 2009/0062187 A1 | 3/2009 | Bianchi et al. |
| 2009/0202500 A1 | 8/2009 | Tamai et al. |
| 2009/0280488 A1 | 11/2009 | Okazawa |
| 2010/0280493 A1 | 11/2010 | Nayak |
| 2011/0091928 A1 | 4/2011 | Tamai et al. |
| 2011/0097309 A1 | 4/2011 | Tamai et al. |
| 2011/0104803 A1 | 5/2011 | Tamai et al. |
| 2012/0251510 A1 | 10/2012 | Tamai et al. |
| 2015/0273017 A1 | 10/2015 | Tamai et al. |
| 2015/0274792 A1 | 10/2015 | Tamai et al. |

FOREIGN PATENT DOCUMENTS

| | | |
|---|---|---|
| CA | 2325226 A | 5/2001 |
| CA | 2512512 A1 | 7/2004 |
| CA | 202636788 | 5/2008 |
| CN | 1439717 A | 9/2003 |
| CN | 1516739 A | 7/2004 |
| CN | 1671742 A | 9/2005 |
| CN | 101366728 A | 2/2009 |
| CN | 101374538 A | 2/2009 |
| CN | 102076350 A | 5/2011 |
| CN | 102443064 | 5/2012 |
| CN | 102711777 A | 10/2012 |
| EP | 0791601 A2 | 8/1997 |
| EP | 1114862 A2 | 7/2001 |
| EP | 1459759 A1 | 9/2004 |
| EP | 2039367 | 3/2009 |
| EP | 2055308 A1 | 5/2009 |
| EP | 2284255 A1 | 2/2011 |
| EP | 2301559 A1 | 3/2011 |
| JP | H9227403 | 9/1997 |
| JP | 2001321434 A | 11/2001 |
| JP | 2003505506 A | 2/2003 |
| JP | 2005508913 A | 4/2005 |
| JP | 2005512507 A | 5/2005 |
| JP | 2005537253 A | 12/2005 |
| JP | 2006510619 A | 3/2006 |
| JP | 2006-124389 A | 5/2006 |
| JP | 2006-517537 A | 7/2006 |
| JP | 2006523085 A | 10/2006 |
| JP | 2007320919 A | 12/2007 |
| JP | 2008507505 A | 3/2008 |
| JP | 2008511300 A | 4/2008 |
| JP | 2010503630 A | 2/2010 |
| KR | 20090078304 A | 7/2009 |
| RU | 2005102593 A | 10/2005 |
| RU | 2410125 C2 | 1/2011 |
| WO | 200108683 A1 | 2/2001 |
| WO | 2002074337 A | 9/2002 |
| WO | 2002088181 A2 | 11/2002 |
| WO | 2002092004 A2 | 11/2002 |
| WO | 2003026691 A2 | 4/2003 |
| WO | 2003043651 A1 | 5/2003 |
| WO | 2004004763 A2 | 1/2004 |
| WO | 2004004770 A1 | 1/2004 |
| WO | 2004044001 A2 | 5/2004 |
| WO | 2004046345 A2 | 6/2004 |
| WO | 2004061456 A2 | 7/2004 |
| WO | 2005025604 A2 | 3/2005 |
| WO | 2005074984 A | 8/2005 |
| WO | 2006008779 A1 | 1/2006 |
| WO | 2006010628 A | 2/2006 |
| WO | 2006024547 A2 | 3/2006 |
| WO | 2006047820 | 5/2006 |
| WO | 2006077614 A | 7/2006 |
| WO | 2006080434 A1 | 8/2006 |
| WO | 2006100651 A1 | 9/2006 |
| WO | 2006114805 A2 | 11/2006 |
| WO | 2007015546 A1 | 2/2007 |
| WO | 2007031100 A1 | 3/2007 |
| WO | 2007130725 A | 11/2007 |
| WO | 2008018641 A1 | 2/2008 |
| WO | 2008031612 A1 | 3/2008 |
| WO | 2008053892 A1 | 5/2008 |
| WO | 2008155659 A2 | 12/2008 |
| WO | 2009133939 A1 | 11/2009 |
| WO | 2009133940 A1 | 11/2009 |
| WO | 2009133943 A1 | 11/2009 |
| WO | 2011046570 | 4/2011 |
| WO | 2011052668 A1 | 5/2011 |
| WO | 2014065347 A1 | 5/2014 |

OTHER PUBLICATIONS

Seong, Y.S. et al., "Hydrophobicity: an acient damage-associated molecular pattern that initiates innate immune responses," Nature Reviews: Immunology, Jun. 2004, 4(6): 469-478.

Shibata, F. et al., "Fibroblast growth-stimulating activity of S100A9 (MRP-14)," European Journal of Biochemistry, 2004, 271(11): 2137-2143.

Shing, Y. et la., "Heparin Affinity: Purification of a Tumor-Derived Capillary Endothelial Cell Growth Factor," Science, 1984, 223(4642): 1296-1299.

Slater, M. et al., "Endometriotic cells exhibit metaplastic change and oxidative DNA damage as well as decreased function, compared to normal endometrium,"Journal of Molecular Histology, 2005, 36(4): 257-263.

Somia, N. et al., "Reviews, Gene Therapy: Trials and Tribulations," Nat. Rev. Genet., Nov. 2000, 1(2): 91-99, Macmillan Publishers Ltd.

Soo, E.T.L. et al., "Heat Shock Proteins as Novel Therapeutic Targets in Cancer," in vivo, 2008, 22(3): 311-315.

Straino, S. et al., "High-Mobility Group Box 1 Protein in Human and Murine Skin: Involvement in Wound Healing," Journal of Investigative Dermatology, 2008, 128:1545-1553.

Sun, S. et al., "Isolation of Mouse Marrow Mesenchymal Progenitors by a Novel and Reliable Method," Stem Cells, 2003, 21(5): 527-535.

Tagami, K. et al., "Elevation of serum high-mobility group box 1 protein during granulocyte colony-stimulating factor-induced peripheral blood stem cell mobilisation," British Journal of Haematology, 2006, 135(4): 567-569. Epub Oct. 10, 2006.

Tagliafico, E. et al., "TGF β/BMP activate the smooth muscle/bone differentiation programs in mesoangioblasts," Journal of Cell Science, 2004, 117(pt 19): 4377-4388.

Tamai et al., "Nihon Hiuka Gakkai Zasshi," Japanese Journal of Dermatology, 2008, 118(4): 645 (#EL28-4) (translated English abstract attached, titled "New Wave of Wound Healing").

Tamai, K. et al., "PDGFRα-positive cells in bone marrow are mobilized by high mobility group box 1 (HMGB1) to regenerate inured epithelia," Proceedings of the National Academy of Sciences, 2011, 108(16): 6609-6614.

Tamai et al., U.S. Appl. No. 11/997,475, "Mesenchymal Stem Cell Inducer, Tissue Regeneration Promoter and Method of Preparing Mesenchymal Stem Cell," filed Jan. 31, 2008, Now Abandoned.

Tamai, K. et al., U.S. Appl. No. 14/436,906, "Novel Method for Treating Cardiac Infarction Using HMGBI Fragment," filed Apr. 20, 2015, and assigned to Genomix Co., Ltd. and Osaka University.

Tamai, K. et al., U.S. Appl. No. 14/436,920, "Novel Method for Treating Spinal Cord Injury Using HMGB1 Fragment," filed Apr. 20, 2015, assigned to Genomix Co., Ltd. and Osaka University.

Tamai, K. et al., "Development and Outlook of Internal Regeneration-Inducing Pharmaceuticals that use in vivo Bone Marrow Mesenchymal Stem / Progenitor Cell-Mobilizing Factors," Gene & Medicine MOOK, Jul. 22, 2012, pp. 207-212.

Tang, D. et al., "High-Mobility Group Box 1, Oxidative Stress, and Disease," Antioxidants & Redox Signaling, 2011, 14(7): 1315-1335. doi: 10.1089/ars.2010.3356.

Takahashi, K. et al., "Modulated Inflammation by Injection of High-Mobility Group Box 1 Recovers Post-Infarction Chronically Failing Heart," Circulation, Sep. 2008, 118(14 Suppl): S106-S114.

Takahashi, K. et al., "Effects of HMGB1 on Postinfarction Chronic Heart Failure—Novel Mechanism Regarding Therapeutic Effects of Cell Therapy," Supplement, 2011, 27 I-E-19: S189.

(56) References Cited

OTHER PUBLICATIONS

Takami, Y. et al., "Synergistic Induction of Hepatocyte Growth Factor in Human Skin Fibroblasts by the Inflammatory Cytokines Interleukin-1 and Interferon-γ," Biochemical and Biophysical Research Communications, 2005, 327: 212-217.
Takeishi, Y. et al., "Importance of Inflammation and Immune Response in Heart Failure—Toll-Like Receptor-Mediated Signaling Pathway and Ventricular Remodeling After Myocardial Infarction," Journal of Clinical and Experimental Medicine, Jan. 30, 2010, 232(5): 378-385.
Tatsumi, R. et al., "HGF/SF Is Present in Normal Adult Skeletal Muscle and Is Capable of Activating Satellite Cells," Developmental Biology, 1998, 194: 114-128.
Telusma, G. et al., "Dendritic cell activating peptides induce distinct cytokine profiles," International Immunology, 2006, 18(11): 1563-1573. Epub Sep. 11, 2006.
Thorey, I.S. et al., "The Ca2+-binding Proteins S100A8 and S100A9 Are Encoded by Novel Injury-regulated Genes*," Journal of Biological Chemistry, 2001, 276(38): 35818-35825. Epub Jul. 19, 2001.
Türker, S. et al., "Nasal route and drug delivery systems," Pharmacy World and Science, 2004, 26: 137-142.
Uchida et al., "Nihon Seikei Geka Gakkai Zasshi," The Journal of Japanese Orthopaedic Surgical Society, 2005, 79(8): S832, 1-P6-6. (English translation attached, titled "The chemotactic activity of PDGF-bb BMP-2, and FGF-2 towards committed and uncommitted mesenchymal stem cells").
Ulloa, L. et al., "High-mobility group box 1 (HMGB1) protein: Friend and foe," Cytokine & Growth Factor Reviews, 2006, 17: 189-201.
Uno, K. et al., "Late Miocene to Pliocene carbon isotope record of differential diet change among East African Herbivores," Proceedings of the National Academy of Sciences, 2011, 108(16): 6509-6514.
Vandal, K. et al., "Blockade of S100A8 and S100A9 Suppresses Neutrophil Migration in Response to Lipopolysaccharide," Journal of Immunology, 2003, 171(5): 2602-2609.
Venereau, E. et al., "Mutually exclusive redox forms of HMGB1 promote cell recuitment of proinflammatory cytokine release," J. Exp. Med., 2012, 209(9): 1519-1528.
Wang, H. et al., "HMG-1 as a Late Mediator of Endotoxin Lethality in Mice," Science, 1999, 285(5425): 248-251.
Wang, H. et al., "Kansaibou no riron to gijutu," Science Press, Mar. 2005, 5: 58-61 (English translation attached, titled "Theories and Technologies for Stem Cells").
Wang, H.L. et al., "High mobility group protein B1 and the research progress of its biological effect," Journal of Chinese Modern Surgery, 2006, 3(22): 1806-1809 (English translation attached).
Wang, L. et al., "Ischemic cerebral tissue and MCP-1 enhance rat bone marrow stromal cell migration in interface culture," Experimental Hematology, 2002, 30: 831-836.
Wang, Y., "Biology of hematopoietic stem cell and the research method therof," Science Press, Mar. 2007, 1st Edition, pp. 56-58.
Wang, W. et al., "Intravenous administration of bone marrow mesenchymal stromal cells is safe for the lung in a chronic myocardial infarction model," Regen Med, Mar. 2011, 6(2): 179-190.
Wexler, S. et al., "Adult Bone Marrow is a Rich Source of Human Mesenchymal 'Stem' Cells but Umbilical Cord and Mobilized Adult Blood are Not," British Journal of Haematology, 2003, 121(2): 368-374.
Wolf, G. et al., "From the Periphery of the Glomerular Capillary Wall Toward the Center of Disease," Diabetes, Jun. 2005, 54(6): 1626-1634.
Woodbury, D. et al., "Adult Rat and Human Bone Marrow Stromal Cells Differentiate into Neurons," Journal of Neuroscience Research, Aug. 15, 2000, 61(4): 364-370.
Wu, Y. et al., "Mesenchymal Stem Cells Enhance Wound Healing Through Differentiation and Angiogenesis," Stem Cells, 2007, 25(10): 2648-2659. Epub Jul. 5, 2007.

Yamada, T. et al., "Regulation of osteoclast development by Notch signaling directed to osteoclast precursors and trough stromal cells," Blood, Mar. 2003, 101(6): 2227-2234.
Yang, D. et al., "High mobility group box-1 protein induces the migration and activation of human dendritic cells and acts as an alarmin," Journal of Leukocyte Biology, 2007, 81(1): 59-66. Epub Sep. 11, 2006.
Youn, J.H. et al., "High Mobility Group Box 1 Protein Binding to Lipopolysaccharide Facilitates Transfer of Lipopolysaccharide to CD14 and Enhances Lipoplysaccharide-Mediated TNF-α Production in Human Monocytes," Journal of Immunology, 2008, 180(7): 5067-5074.
Yuan, Y. et al., "Differentiation of Mesenchymal Stem Cells in Cardiomyogenic Cells Under the Induction of Myocardial Cell Lysate," Chinese Journal of Cardiology, 2005, 33(2): 170-173.
Zhou, X. et al., "Exogenous High-Mobility Group Box 1 Protein Injection Improves Cardiac Function after Myocardial Infarction: Involvement of Wnt Signaling Activation," Journal of Biomedicine and Biotechnology, 2012, vol. 2012, pp. 1-5.
Ishikane, Shin, et al., "Development of multi-growth factor secreted fetal membrane-derived mesenchymal stem cell sheets." Grants-in-Aid for Scientific Research, 2014, pp. 1-6.
Narumi, T., et al., "High-mobility Group Box 1 Attenuates Mitochondrial Dysfunction and Apoptosis via Heat Shock Protein Beta 1 Induction in Doxorubicin-induced Cardiomyopathy." Bulletin of Yamagata University (Medical Science ), 2015, 33(2): 126-127. http://www.lib.yamagata-u.ac.jp/alllib/elib/kiyou/kiyoum/kiyoum-33-2/image/kiyoum-33-2-125to131.pdf.
Panepucci, R. A. et al., "Comparison of Gene Expression of Umbilical Cord Vein and Bone Marrow-Derived Mesenchymal Stem Cells." Stem Cells, Dec. 2004, 22 (7): 1263-1278.
Alden, T. et al., "In Vivo Endochondral Bone Formation Using a Bone Morphogenetic Protein 2 Adenoviral Vector, " Human Gene Therapy, 1999, 10(13): 2245-2253.
Arminan A. et al., "Mesenchymal Stem Cells Provide Better Results Than Hematopoietic Precursors for the Treatment of Myocardial Infarction," JACC, May 18, 2010, 55(20): 2244-2253.
Basso, D.M. et al., "Basso Mouse Scale for Locomotion Detects differences in Recovery after Spinal cord Injury in Five Common Mouse Strains," Journal of Neurotrauma, 2006, 23(5): 635-659.
Berry, M. et al., "Mesenchymal stem cell injection after myocardial infarction improves myocardial compliance," Am J. Physiol Heart Circ Physiol, Jun. 2006, 290(6): H2196-H2203.
Bianchi, M.E. et al., "High mobility group 1 protein (HMGB1) N-terminal peptide," Geneseq Accession No. ADO80180, Aug. 12, 2004.
Bianchi, M.E. et al., "The DNA binding site of HMG1 protein is composed of two similar segments (HMG boxes), both of which have counterparts in other eukaryotic regulatory proteins," The EMBO Journal, Mar. 1992, 11(3): 1055-1063.
Bittira, B. et al., "Mobilization and homing of bone marrow stromal cells in myocardial infarction," European Journal of Cardiothoracic Surgery, 2003, 24(3): 393-398.
Bustin, M. et al., "Regulation of DNA-Dependent Activities by the Functional Motifs of the High-Mobility-Group Chromosomal Proteins," Molecular and Cellular Biology, 1999, 19(8): 5237-5246.
Castro, R. et al., "Failure of Bone Marrow Cells to Transdifferentiate into Neural Cells in Vivo," Science, 2002, 297(5585): 1299.
Chamberlain, G. et al., "Concise Review: Mesenchymal Stem Cells: Their Phenotype, Differentiation Capacity, Immunological Features, and Potential for Homing," Stem Cells, 2007, 25: 2739-2749.
Charoonpatrapong, K. et al., "HMGB1 Expression and Release by Bone Cells," Journal of Cellular Physiology, 2006, 207(2): 480-490.
Chen, X. et al., "Human Bone Marrow Stromal Cell Cultures Conditioned by Traumatic Brain Tissue Extracts: Growth Factor Production," Journal of Neuroscience Research, 2002, 69: 687-691.
Chen, Y. et al., "Coaxing bone marrow stromal mesenchymal stem cells towards neuronal differenctiation: progress and uncertainties," Cellular and Molecular Life Sciences, 2006, 63(14): 1649-1657.
Chopp, M. et al., "Treatment of neural injury with narrow stromal cells," The Lancet Neurology, 2002, 1(2): 92-100.

(56) References Cited

OTHER PUBLICATIONS

Chou, D. et al., "Identity of nuclear high-mobility-group protein, HMG-1, and sulfoglucuronyl carbohydrate-binding protein, SBP-1, in brain," Journal of Neurochemistry, 2001, 77(1): 120-131.
Cole, J., "Pharmacologic Mobilization of Mesenchymal Stem Cells for Enhanced Bone Formation," Colby College, Rush University, 2009, UMI No. 1466383, pp. 1-82.
Degryse, B. et al., "The High Mobility Group (HMG) Boxes of the Nuclear Protein HMG1 Induce Chemotaxis and Cytoskeleton Reorganization in Rat Smooth Muscle Cells," Journal of Cell Biology, 2001, 152(6): 1197-1206.
Delarosa, O. et al., "Modulation of Adult Mesenchymal Stem Cells Activity by Toll-Like Receptors: Implications on Therapeutic Potential," Mediators of Inflammation, 2010, 2010:865601. Epub Jun. 14, 2010.
De Souza, A.W.S. et al., "HMGB1 in Vascular Diseases: Its Role in Vascular Inflammation and Atherosclerosis," Autoimmunity Reviews, 2012, 11: 909-917.
Dong, Y. et al., "HMGB1 Protein Does Not Mediate the Inflammatory Response in Spontaneous Spinal Cord Regeneration," The Journal of Biological Chemistry, Jun. 21, 2013, 288(25): 18204-18218.
Eckert, R. et al., "S100 Proteins in the Epidermis," Journal of Investigative Dermatology, 2004, 123(1): 23-33.
Ehrchen, J.M. et al., The endogenous Toll-like receptor 4 agonist S100A8/S100A9 (calprotectin) as innate amplifier of infection, autoimmunity, and cancer, Journal of Leukocyte Biology, 2009, 86: 557-566.
Erlandsson, H. et al., "The nuclear protein HMGB1 as a proinflammatory mediator," European Journal of Immunology, 2004, 34(6): 1503-1512.
Esposito, E. et al., "Melatonin reduces stress-activated/mitogen-activated protein kinases in spinal cord injury," J. Pineal Res., 2009, 46: 79-86.
Fang, P. et al., "HMGB1 Contributes to Regeneration After Spinal Cord Injury in Adult Zebrafish," Mol Neurobiol, 2014, 49: 472-483.
Forte, G. et al., "Hepatocyte Growth Factor Effects on Mesenchymal Stem Cells: Proliferation, Migration, and Differentiation," Stem Cells, 2006, 24: 23-33.
Fujii, M. et al., Roles of Bone Morphogenetic Protein Type 1 Receptors and Smad Proteins in Osteoblast and Chrondoblast Differentiation, Molecular Biology of the Cell, 1999, 10(11): 3801-3813.
Germani, A. et al., "Pivotal Advance: High-mobility group box 1 protein—a cytokine with a role in cardiac repair," Journal of Leukocyte Biology, 2007, 81(1): 41-45. Epub Aug. 29, 2006.
Gong, W. et al., "The Anti-Inflammatory Activity of HMGB1 A Box is Enhanced When Fused with C-Terminal Acidic Tail," Journal of Biomedicine and Biotechnology, 2010, vol. 2010, Article ID 915234, 6, pp. 2-10. doi:10.115/2010915234.
Granero-Molto, F. et al., "Role of mesenchymal stem cells in regenerative medicine: application to bone and cartilage repair," Expert Opinion on Biological Therapy, 2008, 8(3): 255-268.
Gudjonsson, J. et al., "Psoriasis," Fitzpatrick's Dermatology in General Medicine, 8th edition, New York: Mc-Graw Hill Medical, 2012, pp. 197-217.
Gueukdjian S.A., "Intra-Arterial Injections in the Treatment of Peripheral Vascular Disease," Postgrad Medical Journal, Jan. 1955, 31(351): 30-31.
Harris, H. et al., "Alarmin(g) news about danger," EMBO Reports, 2006, 7(8): 774-778. Epub Jul. 21, 2006.
Healthwise Staff, "Age-related Macular Degeneration," University of Michigan Health System, Aug. 2015, https:www.uofmhealth.org/health-library/hw176039.
Heil, M. et al., "An engineered heparin-binding form of VEGF-E (hbVEGF-E)," Angiogenesis, 2003, 6(3): 201-211.
Herrera, M.B. et al., "Exogenous mesenchymal stem cells localize to the kidney by means of CD44 following acute tubular injury," Kidney International, 2007, 72: 430-441.
Hiratsuka S. et al., "Tumour-mediated upregulation of chemoattractants and recruitment of myeloid cells predetermines lung metastasis," Natural Cell Biology, 2006, 8(12): 1369-1375. Epub Nov. 26, 2006.
HMGBiotech, "BoxA from HMGB1, human & mouse, LPS-free." HMGBiotech Srl, 2008, C.F. e P.IVA 04942740962, http://www.hmgbiotech.com/products.php?ID=91.
HMGBiotech, "BoxA from HMGB1, human & mouse, LPS-free-Datasheet." HMGBiotech Srl, 2008, Via Moretto Brescia 25, 20133—Milano, Italy, http://www.hmgbiotech.com/upload/documenti/0515122144_boxa.
Hori, O. et al., "The Receptor for Advanced Glycation End Products (RAGE) Is a Cellular Binding Site for Amphoterin," Journal of Biological Chemistry, 1995, 270(43): 25752-25761.
Huttunen, H.J. et al., "Receptor for Advanced Glycation End Products-binding COOH-terminal Motif of Amphoterin Inhibits Invasive Migration and Metastasis," Cancer Research, 2002, 62: 4805-4811.
Ishikane, S., "Therapeutic application of allogenic fetal membrane-derived mesenchymal stem cells transplantation in regenerative medicine," Pharmaceutical Bulletin of Fukuoka University, Mar. 2011, 11(0): 17-25.
Jansen, J. et al., "Transplantation of hematopoietic stem cells from the peripheral blood," Journal of Cellular and Molecular Medicine, 2005, 9(1): 37-50.
Jayaraman, L. et al., "High mobility group protein-1 (HMG-1) is a unique activator of p53," Genes & Development, 1998, 12(4): 462-472.
Jiang, Y. et al., "Pluripotency of mesenchymal stem cells derived from adult marrow," Nature, 2002, 418(6893): 41-49. Epub Jun. 20, 2012.
Jiao, C. et al., "Researchers find nerve damage may precede diabetic retinopathy," EurekAlert! Science News, Apr. 2016, https://www.eurekalert.org/pub_releases/2016-04/uoih-rfv042616.php.
Kassis, I. et al., "Isolation of mesenchymal stem cells from G-CSF mobilized human peripheral blood using fibrin microbeads," Bone Marrow Transplant, 2006, 37(10): 967-976.
Kawabata, H. et al., "High Mobility Group Box 1 Is Upregulated After Spinal Cord Injury and Is Associated With Neuronal Cell Apoptosis," Spine, 2010, 35(11): 1109-1115.
Kern, S. et al., "Comparative Analysis of Mesenchymal Stem Cells from Bone Marrow, Umbilical Cord Blood, or Adipose Tissue," Stem Cells, 2006, 24(5): 1294-1301. Epub Jan. 12, 2006.
Kessler, M.W. et al., "Tissue Engineering and Cartilage," Organogenesis, Jan. 2008, 4(1): 28-32.
Institutional Animal Care and Use Committe (IACUC), "Blood Collection: The Mouse," May 2014, University of California, San Fransisco. Taken from web: iacuc.usfc.edu/Policies/BloodCollectionMice.doc.
Instruction Manual of HiTrap Chelating HP (Amersham Biosciences), 2003, pp. 1-6.
Kikuchi, K. et al., "HMGB1 as a therapeutic target in spinal cord injury: A hypothesis for novel therapy development (Review)," Experimental and Therapeutic Medicine, 2011, 2: 767-770.
Kim, S. et al., "Skin Regeneration Using Keratinocytes and Dermal Fibroblasts Cultured on Biodegradable Microspherical Polymer Scaffolds," Journal of Biomedical Materials Research Part B: Applied Biomaterials, 2005, 75(2): 369-377.
Kitahara, T. et al., "High-Mobility Group Box 1 Restores Cardiac Function After Myocardial Infarcation in Transgenic Mice," Cardiovascular Research, European Society of Cardiology, Oct. 1, 2008, 80: 40-46.
Kirov, S.A. et al., "In Vivo 2-Photon Microscopy Reveals G-CSF Enhanced Mobilization and Targeting of Neo-Endogenous Bone Marrow Stromal Cells to Stroke Injury Sites," Stroke, Apr. 2009, 40(4): 1-2, e133, Abstract No. 107.
Koc, O. et al., "Mesenchymal Stem Cells: Heading into the Clinic," Bone Marrow Transplantation, 2001, 27(3): 235-239.
Kohno, T. et al., "High Mobility Group Box 1 Protein is Associated With Post-Infarction Healing Process and Left Ventricular Remodeling," Circ. J., 2008, 72 Supplement 1, p. J-004: 510-511.
Laflamme, M. et al., "Regenerating the heart," Nature Biotechnology, 2005, 23(7): 845-856.

(56) References Cited

OTHER PUBLICATIONS

La Rosa, T.J. et al., "Glycine max protein SEQ ID No. 211221," Geneseq Accession No. AFQ20044, 2007.
Lanza, R. et al., "Essentials of Stem Cell Biology—Chapter 27, Mesenchymal Stem Cells," Elsevier Academic Press, 2006, pp. 205-210.
Li, S. et al., "Millennium Review, Nonviral gene therapy: promises and challenges," Gene Ther., 2000, 7: 31-34, Macmillan Publishers Ltd.
Li, Y. et al., "Advancement of Human Multiply, Sex health and Reproductive Medical Science," Peking University Medical Press, Mar. 2007, 1st Edition, pp. 270-271.
Li, Z. et al., "Heat-Shock Proteins," Current Protocols in Immunology, 2003, Supplement 58, A.IT.1-A.IT.6.
Limana, F. et al., "Exogenous High-Mobility Group Box 1 Protein Induces Myocardial Regeneration After Infarction via Enhanced Cardiac C-Kit+ Cell Proliferation and Differentiation," Circulation Research, 2005, 97(8): e73-83. Epub Sep. 15, 2005.
Lin, S. et al., "The isolation of novel mesenchymal stromal cell chemotactic factors from the conditioned medium of tumor cells," Experimental Cell Research, 2008, 314(17): 3107-3117. Epub Aug. 8, 2008.
Liotta, F. et al., "Toll-Like Receptors 3 and 4 Are Expressed by Human Bone Marrow-Derived Mesenchymal Stem Cells and Can Inhibit Their T-Cell Modulatory Activity by Impairing Notch Signaling," Stem Cells, 2008, 26(1): 279-289. Epub Oct. 25, 2007.
Liu, K.et al., "Human Placental Extract Stimulates Liver Regeneration in Rats," Biological and Pharmaceutical Bulletin, 1998, 21(1): 44-49.
Lonza BenchGuides_Poietics hMSC Human Mesenchymal Stem Cells and Media( Document # TS-PT-212-7 04/08).
Mansbridge, J. et al., "Skin Tissue Engineering," J. Biomater, Sci. Polymer, Ed., Aug. 1, 2008, 19(8): 955-968.
Martin-Murphy, B.V. et al., "The Role of Damage Associated Molecular Pattern Molecules in Acetaminophen-Induced Liver Injury in Mice," Toxicol Lett, Feb. 2010, 192(3): 1-20.
Maruyama, I., "Inflammation and HMGB1/RAGE system," Kekkan Igaku, 2005, 6(5): 519-525 (English translation attached).
Matsumoto, K., et al., "Up-Regulation of Hepatocyte Growth Factor Gene Expression by Inerleukin-1 in Human Skin Fibrosis," Biochemical and Biophysical Research Communications, 1992, 188(1): 235-243.
Meng, E. et al., "High Mobility Group Box 1 Protein Inhibits the Proliferation of Human Mesenchymal Stem Cells and Promotes Their Migration and Differentiation along Osteoblastic Pathway," Stem Cells and Development, 2008, 17(4): 805-814.
Meng, E. et al., "HMGB1 induces migration of human bone marrow-derived mesenchymal stem cells," Bulletin of the Academy of Militaryt Medical Sciences, 2006, 30(3): 213-216 (English translation attached).
Merenmies, J. et al., "30-kDa Heparin-binding Protein of Brain (Amphoterin) Involved in Neurite Outgrowth," Journal of Biological Chemistry 1991, 266(25): 16722-16729.
Mistry, A.R. et al., "Recombinant HMG1 Protein Produced in Pichia pastoris: A Nonviral Gene Delivery Agent," Biotechniques, 1997, 22(4): 718-729.
Mori, T. et al., "Stem Cells/ES cells—Mesenchymal Stem Cells—Human Bone Marrow Derived Mesenchymal Stem Cells," Saisei Iryou—Regenerative Medicine, 2005, 4(3): 421-429, 351.
Morosetti, R. et al., "MyoD expression restores defective myogenic differentiation of human mesoangioblasts from inclusion-body myositis muscle," PNAS, Nov. 7, 2006, 103(45): 16995-17000.
Muhammad, S. et al., "The HMGB1 Receptor RAGE Mediates Ischemic Brain Damage," Journal of Neuroscience, 2008, 28(46): 12023-12031.
Müller, S. et al., "The double life of HMGB1 chromatin protein: architectural factor and extracellular signal," EMBO Journal, 2001, 20(16): 4337-4340.
Nakajima et al., "Dynamics and Role of High Mobility Group Box-1 (HMGB-1) in Injured Spinal Cord," Nihon Seikei Geka Gakkai Zasshi (J. Jpn. Orthop. Assoc.), 2010, 84(8): S1050.
Nakamura, K. et al., "p38 Mitogen-Activated Protein Kinase Functionally Contributes to Chondrogenesis Induced by Growth/Differentiation Factor-5 in ATDC5 Cells," Experimental Cell Research, 1999, 250(2): 351-363.
Opitz, C.E. et al., "Toll-Like Receptor Engagement Enhances the Immunosuppressive Properties of Human Bone Marrow-Derived Mesenchymal Stem Cells by Inducing Indoleamine-2, 3-dioxygenase-1 via Interferon-β and Protein Kinase R," Stem Cells, 2009, 27(4): 909-919.
Otsuru, S. et al., "BMP-2 mobilizes robust bone marrow mesenchymal progenitor cells to the circulating blood in bone regeneration," The 28th Meeting of the Molecular Biology Society of Japan, 2005, 733(3P-1012) (translated English abstract attached).
Ozaki, Y. et al., "Comprehensive Analysis of Chemotactic Factors for Bone Marrow Mesenchymal Stem Cells," Stem Cells and Development, 2007, 16(1): 119-129.
Palumbo, R. et al., "Extracellular HMGB1, a signal of tissue damage, induces mesoangioblast migration and proliferation," The Journal of Cell Biology, 2004, 164(3): 441-449.
Palumbo, R. et al., "Cells migrating to sites of tissue damage in response to the danger signal HMGB1 require NF-kB activation," Journal of Cell Biology, 2007, 179(1): 33-40.
Palumbo, R. et al., "High mobility group box 1 protein, a cue for stem cell recruitment," Biochemical Pharmacology, 2004, 68(6): 1165-1170.
Panepucci, R.A. et al., "Abstract # 4427: Comparison of Gene Expression of Mesenchymal Stem Cells from the Umbilical Cord and from the Bone Marrow," Blood, Nov. 2003, 16(102): Abstract.
Pankov, R. et al., "Fibronectin at a glance, J. Cell Sci., Oct. 2002, 115(20): 3861-3863.
Paul, S.R. et al., "Stromal Cell-Associated Hematopoiesis: Immortalization and Characterization of a Primate Bone Marrow-Derived Stromal Cell Line," Blood, 1991, 77(8): 1723-1733.
Pevsner-Fischer, M. et al., "Toll-like receptors and their ligands control mesenchymal stem cell functions," Blood, 2007, 109(4): 1422-1432. Epub Oct. 12, 2006.
Pittenger, M. et al., "Multilineage Potential of Adult Human Mesenchymal Stem Cells," Science, 1999, 284(5411): 143-147.
Popovic, K. et al., "Increased Expression of the Novel Proinflammatory Cytokine High Mobility Group Box Chromosomal Protein 1 in Skin Lesions of Patients With Lupus Erythematosus," Arthritis & Rheumatism, 2005, 52(11): 3639-3645.
Pusterla, T. et al., "High mobility group B2 is secreted by myeloid cells and has mitogenic and chemoattractant activities similar to high mobility group B1," Autoimmunity, 2009, 42(4): 308-310.
Quertainmont, R. et al., "Mesenchymal Stem Cell Graft Improves Recovery after Spinal Cord Injury in Adult Rats through Neurotrophic and Pro-Angiogenic Actions," PLoS One, Jun. 2012, 7(6): 1-15.
Rahimi-Movaghar, V. et al., "Effect of Decompression on Complete Spinal Cord Injury in Rats," International Journal of Neuroscience, 2008, 118: 1359-1373.
Raicevic, G. et al., "Inflammation modifies the pattern and the function of Toll-like receptors expressed by human mesenchymal stromal cells," Human Immunology, 2010, 71(3): 235-244. Epub Jan. 6, 2010.
Robinson, M.J. et al., "The S100 Family Heterodimer, MRP-8/14, Binds with High Affinity to Heparin and Heparan Sulfate Glycosaminoglycans on Endothelial Cells," Journal of Biological Chemistry, 2002, 277(5): 3658-3665. Epub Nov. 26, 2001.
"Isolating culture and induced differentiation of marrow mesenchyma stem cells," Principles and Protocols of Tissue Engineering, Jun. 2004, 277-8 (English translation attached).
Tamai, K. et al., US. Appl. No. 15/674,835, "Method for Collecting Functional Cells In Vivo With High Efficiency." filed Aug. 11, 2017.
Tamai, Katsuto et al., "PDGFRα-positive cells in bone marrow are mobilized by high mobility group box 1 (HMGB1) to regenerate injured epithelia," http://www.pnas.org/content/early/2011/03/30/1016753108.full.pdf+html, http://www.pnas.org/content/early/2011/03/30/1016753108/suppl/DCSupplemental, http://www.pnas.org/content/suppl/2011/03/31/1016753108.DCSupplemental/pnas.

(56) References Cited

OTHER PUBLICATIONS

201016753SI.pdf, http://www.pnas.org/content/early/2011/03/30/1016753108.abstract, http://www.pnas.org/content/early/2011/03/30/1016753108.full.pdf.

Tamai, Katsuto et al., "PDGFRα-positive cells in bone marrow are mobilized by high mobility group box 1 (HMGB1) to regenerate injured epithelia," http://www.pnas.org/content/108/16/6609.full.pdf+html, http://www.pnas.org/content/108/16/6609/suppl/DCSupplemental, http://www.pnas.org/content/suppl/2011/03/31/1016753108.DCSupplemental/pnas.201016753SI.pdf, http://www.pnas.org/content/108/16/6609.abstract, http://www.pnas.org/content/108/16/6609.figures-only, http://www.pnas.org/content/108/16/6609.full.pdf, http://www.pnas.org/.

Goto, et al., "Investigation of the application of myocardial regeneration inducing therapy using HMGB1 to cardiac infarction." Regenerative Medicine, Feb. 1, 2017, 16: 289.

Kikuchi, et al., "Systemic administration of HMGB1 improves bleomycin-induced skin fibrosis by locally accumulating bone marrow mesenchymal stem cells." Regenerative Medicine, Feb. 1, 2017, 16: 422.

Komurasaki, et al., "HMGB1 ameliorates bleomycin-induced skin fibrosis by promoting accumulation of mesenchymal stem cells to the lesion." The 48th Annual Meeting of the Japanese Society of Matrix Biology and Medicine, 2016, p. 78.

Saver, J.L, "Time Is Brain-Quantified." Stroke, 2006, 37: 263-266.

Tamai, K., "Development of regeneration-inducing medicine utilizing the in vivo injured tissue regeneration mechanism of peripheral circulating mesenchymal cells." BIO Clinica, Sep. 10, 2016, 31(10): 1042-1046.

Tamai, et al., "Tissue repair mechanism by bone-marrow-derived stem cells." Experimental Mediciner, 2013, 31(5): 655-661.

Wang, F.-C., et al., "Overexpression of HMGB1 A-box reduced lipopolysaccharide-induced intestinal inflammation via HMGB1/TLR4 signaling in vitro." World J Gastroenterol, Jul. 7, 2015, 21(25): 7764-7776.

Zheng, X., et al., "Adeno-associated virus-mediated colonic secretory expression of HMGB1 A box attenuates experimental colitis in mice." J Gene Med, 2016, 18(10): 261-272.

Chen, T., et al., "Involvement of high mobility group box-1 in imiquimod-induced psoriasis-like mice model." Journal of Dermatology, 2017, 44: 573-581.

Yamaoka, S., et al., "1043 Systemic delivery of HMGB1 peptide ameliorates imiquimod-induced psoriasis-like dermatitis." Journal of Investigative Dermatology, 2018, 138(5): S177.

Yang, H., et al., "Reversing established sepsis with antagonists of endogenous high-mobility group box 1." Proceedings of the National Academy of Sciences, 2004, 101(1): 296-301.

\* cited by examiner

Migration-promoting activity on primary culture mesenchymal stem cells

C57/Bl6 mouse bone marrow cells

Sorting

CD11b(+)     CD11b(−)

Macrophage     Mesenchymal stem cells

PDGFRα (−)     PDGFRα (+)

GFP Fluorescence

Bright field

CD11b-negative, PDGFRα-positive cells

Peptide (1-44)  40   0
(μg/mL)

Bone differentiation

PDGFR α (+)Lin(-)c-kit(-)

Adipocyte differentiation

PDGFR α (+)Lin(-)c-kit(-)

HEK293-derived peptides migration-promoting activity
Peptide (1-44)

PDGFRα
Keratinocytes
Immunohistochemical images

PDGFRα
Fibroblasts
Immunohistochemical images

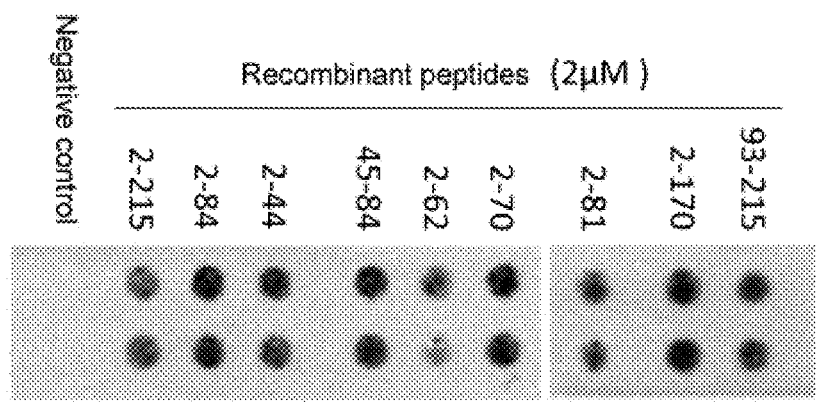
FIG. 18B
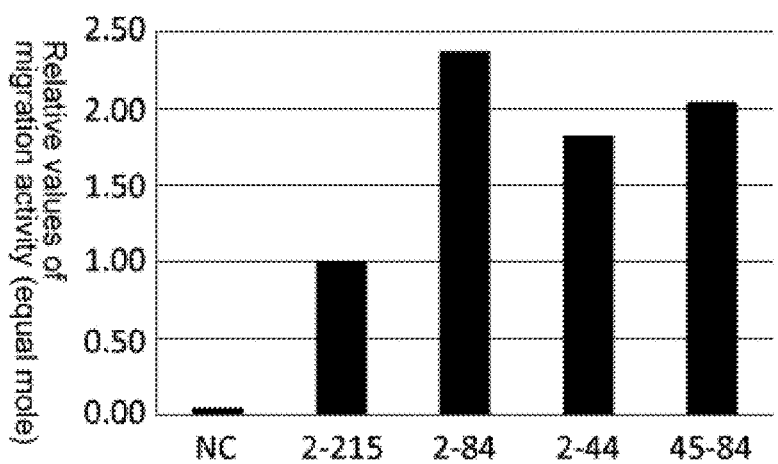
FIG. 18C
| Relative values of migration activity | | |
|---|---|---|
| | Equal mole (2 μM) | Equal mass conversion |
| NC | 0.04 | – |
| 2-215 | 1 | 1 |
| 2-84 | 2.37 | 5.5 |
| 2-44 | 1.82 | 7.1 |
| 45-84 | 2.04 | 8.1 |
FIG. 18D Recombinant peptides (final concentration 2 μM)

Cell : Human MCS   1.5 x 10$^6$ cells /ml

Seven weeks later

PBS-administered group | 1-215(HEK) (100μg/individual/day) | 1-44(Synthetic peptide) (50μg/individual/day)

(mm)

PEPTIDE FOR INDUCING REGENERATION OF TISSUE AND USE THEREOF

CROSS-REFERENCE TO RELATED APPLICATIONS

This application is a continuation Application of application Ser. No. 14/114,395, filed Feb. 6, 2014; which is a National Stage Application of International Application Number PCT/JP2012/059113, filed Apr. 3, 2012; which claims priority to Japanese Application No. 2011-098270, filed Apr. 26, 2011; and Japanese Application No. 2011-219454, filed Oct. 3, 2011; all of which are incorporated herein by reference in their entirety.

TECHNICAL FIELD

The present invention relates to peptides for inducing tissue regeneration and uses thereof.

The Sequence Listing for this application is labeled "SeqList-18Feb14.txt", which was created on Feb. 18, 2014, and is 13 KB. The entire content is incorporated herein by reference in its entirety.

BACKGROUND OF THE INVENTION

It has been becoming clear that each organ or tissue in the living organism has tissue stem cells that maintain its structural and functional homeostasis. For example, cardiac stem cells are present in the heart, neural stem cells are present in the brain, and epidermal stem cells and hair follicle stem cells are present in the skin. They provide cardiomyocytes, neurons, and epidermal cells and hair follicle epithelial cells to the heart, brain, and skin, respectively, over a lifetime to maintain their structures and functions. Meanwhile, hematopoietic stem cells, which differentiate into blood cells such as erythrocytes, leukocytes, and platelets, are present in the bone marrow. The blood cells derived from hematopoietic stem cells circulate through all organs or tissues in the body via blood flow and serve essential functions for the maintenance of life, such as oxygen supply, immune response, arrest of hemorrhage, and repair of damaged tissues. Thus, it is fair to say that bone-marrow hematopoietic stem cells contribute to maintaining the homeostasis of all tissues in the body via peripheral circulation, rather than maintaining the homeostasis of bone marrow and bone tissues where they are localized.

Recently, it has been demonstrated that, in addition to hematopoietic stem cells, mesenchymal stem cells capable of differentiating into not only mesodermal tissues such as bone, cartilage, and adipose but also ectodermal tissues such as neuron and epidermis are present in the bone marrow. However, little is understood about the significance of the presence of mesenchymal stem cells in the living body. However, given that hematopoietic stem cells that maintain the homeostasis of all organs and tissues by supplying blood cells via peripheral circulation are present in the bone marrow, it is expected that mesenchymal stem cells present in the bone marrow may also contribute to the homeostatic maintenance of living tissues by supplying cells capable of differentiating into bone, cartilage, adipose, neuron, epithelium, etc., to tissues or organs in need thereof in the living body via peripheral circulation.

Currently, regenerative medicine is under intensive development, in which bone marrow mesenchymal stem cells are prepared by collecting bone-marrow blood, and after expansion by cell culture, the cells are grafted into the site of intractable tissue damage or into peripheral circulation to induce regeneration of the damaged tissue. Clinical application of bone marrow mesenchymal stem cell transplantation has already been underway in regenerative medicine for cerebral infarction, cardiac infarction, intractable skin ulcer, etc. Furthermore, transplanted bone marrow mesenchymal stem cells have been demonstrated to produce the effect of suppressing inflammation and immune response as well as the effect of suppressing fibrous scar formation at local sites in the body. Clinical trials have begun on bone marrow mesenchymal stem cell transplantation therapy as a new therapeutic method to treat scleroderma, which is an autoimmune disease, or to treat graft versus host disease (GVHD), which is a serious side effect after bone marrow transplantation or blood infusion. However, bone-marrow blood containing bone marrow mesenchymal stem cells is collected only by an invasive method where thick needles are repeatedly inserted into the iliac bone. In addition, continuous passages of bone marrow mesenchymal stem cells outside the body lead to gradual loss of their proliferative ability and multipotency. Moreover, since culturing bone marrow mesenchymal stem cells with high quality control for ensuring the safety of in vivo transplantation requires special cell culture facilities such as cell processing center (CPC), it can only be performed currently in very limited universities and companies. Thus, in order to make the regenerative medicine using bone marrow mesenchymal stem cells available to a large number of patients around the world suffering from intractable tissue damage, it is an urgent task to develop techniques for mesenchymal stem cell regenerative medicine that can be performed in any medical facilities.

High mobility group box 1 (HMGB1) protein was identified about 30 years ago as a non-histone chromatin protein that regulates gene expression and DNA repair by regulating the structure of nuclear chromatin. The structure of the HMGB1 protein is primarily constituted by two DNA-binding domains, and those at the N- and C-terminal are referred to as A-box and B-box, respectively. Past studies have revealed that the domain which binds TLR to induce inflammatory reaction is located within the B-box of the HMGB1 molecule.

PRIOR-ART DOCUMENTS

Patent Documents

Patent Document 1: WO2008/053892
Patent Document 2: WO2007/015546
Patent Document 3: WO2009/133939
Patent Document 4: WO2009/133943
Patent Document 5: WO2009/133940
Patent Document 6: Japanese Patent Kohyo Publication No. (JP-A) 2005-537253 (unexamined Japanese national phase publication corresponding to a non-Japanese international publication)

Non-Patent Documents

Non-patent Document 1: Bustin et al., Mol Cell Biol, 19: 5237-5246, 1999
Non-patent Document 2: Hori et al., J. Biol. Chem., 270, 25752-25761, 1995
Non-patent Document 3: Wang et al., Science, 285: 248-251, 1999
Non-patent Document 4: Muller et al., EMBO J, 20: 4337-4340, 2001

Non-patent Document 5: Wang et al., Science, 285: 248-251, 1999

Non-patent Document 6: Germani et al., J Leukoc Biol. January; 81(1): 41-5, 2007

Non-patent Document 7: Palumbo et al., J. Cell Biol., 164: 441-449, 2004

Non-patent Document 8: Merenmies et al., J. Biol. Chem., 266: 16722-16729, 1991

Non-patent Document 9: Wu Y et al., Stem cells, 25: 2648-2659, 2007

Non-patent Document 10: Tamai et al., Proc Natl Acad Sci USA. 2011 Apr. 4. [Epub ahead of print], 108: 6609-6614, 2011

Non-patent Document 11: Yang et al., J Leukoc Biol. January; 81(1): 59-66, 2007

DISCLOSURE OF THE INVENTION

Problems to be Solved by the Invention

The present inventors recently conducted studies to elucidate the mechanism of regeneration of exfoliated epidermis in "epidermolysis bullosa", which is an intractable hereditary skin disorder showing skin exfoliation of the whole body and burn-like symptoms all over the body due to abnormality in the gene of an adhesion molecule in the basal membrane region of skin. Using epidermolysis bullosa model mice transplanted with green fluorescent protein (GFP) transgenic bone marrow cells, the present inventors revealed that the high mobility group box 1 (HMGB1) protein released from exfoliated epidermis to blood stimulates and recruits platelet-derived growth factor receptor alpha (PDGFRα)-positive cells from bone marrow to blood and thereby promotes the accumulation of the cells to the site of epidermal exfoliation, and that PDGFRα-positive cells localized at the site of epidermal exfoliation differentiated into fibroblasts and epidermal cells and had a great contribution to the regeneration of damaged skin. The present inventors also revealed that, when a recombinant HMGB1 protein was administered via the caudal vein after induction of skin ulcer or cerebral infarction in mice, PDGFRα-positive cells were recruited from the bone marrow into the blood and accumulated to the site of skin ulceration or cerebral infarction, thereby strongly inducing regeneration from skin ulceration or cerebral infarction. Intramedullary PDGFRα-positive cells have been previously reported to be mesenchymal stem cells capable of differentiating into bone, cartilage, and adipose, and also into neuron and epithelium. Thus, it has been found possible to allow many mesenchymal stem cells to accumulate at damaged tissues in the living organism by administering HMGB1 to mobilize intramedullary PDGFRα-positive mesenchymal stem cells into peripheral circulation, without performing special ex vivo culture of cells collected from the body.

If HMGB1 is developed into a pharmaceutical agent for inducing regeneration of damaged tissues by recruiting bone marrow mesenchymal stem cells to blood in the body, every medical facility will be able to perform regenerative medicine based on bone marrow mesenchymal stem cells. This will solve many problems that the above-mentioned current bone marrow mesenchymal stem cell-based regenerative medicine faces.

As described above, HMGB1 pharmaceuticals are revolutionary therapeutic agents that promote the recruitment of bone marrow mesenchymal stem cells into blood and accumulation of the cells to damaged tissues, thereby inducing tissue regeneration in the body. In previous studies conducted by the present inventors, no side effects were observed even when a high concentration of recombinant HMGB1 protein was administered to mice or rats. In view of this, as well as the fact observed by the present inventors that a significantly high level of HMGB1 is present in the peripheral blood of epidermolysis bullosa patients who have no severe symptoms except epidermal exfoliation, it is expected that HMGB1 administration is highly safe. However, there are also reports that HMGB1 has an inflammatory effect. As described above, there are several findings on HMGB1; however, nothing is known about the effect of fragments of the HMGB1 protein on mesenchymal stem cells or what roles they play in tissue regeneration.

Means for Solving the Problems

The present inventors had a peptide consisting of amino acids at positions 1 to 84 of an HMGB1 protein and a peptide consisting of amino acids at positions 85 to 169 of the HMGB1 protein respectively secreted as recombinant proteins into HEK293 cell media. The proteins of interest in the media were each purified by chromatography, and their migration-promoting activity on the PDGFRα-positive bone marrow mesenchymal stem cell line (MSC-1) was examined. As a result, the present inventors found that the peptide consisting of amino acids of positions 1 to 84 showed migration-promoting activity.

Then, based on the peptide consisting of amino acids at positions 1 to 84 of the HMGB1 protein which was confirmed to have migration-promoting activity on MSC-1, the present inventors prepared a peptide consisting of amino acids at positions 1 to 44 and a peptide consisting of amino acids at positions 45 to 84, and examined each peptide for migration-promoting activity. The results showed that both peptide fragments exhibited migration-promoting activity on the PDGFRα-positive bone marrow mesenchymal stem cell line (MSC-1).

Then, various peptide fragments overlapping each other around the above respective fragments were chemically synthesized, and evaluated for their migration-promoting activity on the PDGFRα-positive bone marrow mesenchymal stem cell line (MSC-1). As a result, the present inventors identified several peptides showing migration-promoting activity.

Further, the present inventors confirmed that the identified peptides have migration-promoting activity on skin fibroblasts, which are PDGFRα-positive, and have an effect of reducing the size of cerebral infarcts in a cerebral infarction model mouse.

The present inventors had a recombinant protein consisting of amino acids of positions 2 to 84 of the HMGB1 protein and a recombinant protein consisting of amino acids of positions 89 to 215 of the HMGB1 protein expressed in *E. coli*. The expressed proteins were purified by column chromatography, and examined for their migration-promoting activity on the PDGFRα-positive bone marrow mesenchymal stem cell line (MSC-1) and on human bone marrow mesenchymal stem cells. As a result, the present inventors confirmed migration-promoting activity of the peptide consisting of amino acids of positions 2 to 84 and the peptide consisting of amino acids of positions 89 to 215.

Next, based on the peptide consisting of amino acids of positions 2 to 84 which was confirmed to have migration-promoting activity on MSC-1 and human bone marrow mesenchymal stem cells, the present inventors prepared a peptide consisting of amino acids of positions 2 to 44 and a peptide consisting of amino acids of positions 45 to 84, and examined them for their migration-promoting activities. The result showed that both peptide fragments prepared exhibited migration-promoting activity on MSC-1 and human bone marrow mesenchymal stem cells.

Next, based on the peptide consisting of amino acids of positions 89 to 215 which was confirmed to have migration-promoting activity on MSC-1 and human bone marrow mesenchymal stem cells, the present inventors prepared peptides with the C-terminus increasingly shortened, i.e. a peptide consisting of amino acids of positions 89 to 205, a peptide consisting of amino acids of positions 89 to 195, and a peptide consisting of amino acids of positions 89 to 185, and examined each of them for migration-promoting activity. The result showed that among the prepared peptide fragments, those with a shorter C terminus demonstrated more enhanced migration-promoting activity on the PDGFRα-positive bone marrow mesenchymal stem cell line (MSC-1) and human bone marrow mesenchymal stem cells.

Further, when three types of fusion peptides were generated by adding to the peptide consisting of amino acids of positions 2 to 84, a whole or partial C-terminal acidic tail consisting of aspartic acid and glutamic acid (10-, 20-, or 30-amino acid sequence), it was surprisingly found that the migration-promoting activity of the 2-84 peptide was extremely reduced for all fusion peptides. This shows that a whole or partial acidic tail suppressively regulates the migration-promoting activity of full-length HMGB1. It became clear by the above fragmentation that there are at least three or more migration-promoting activity domains, and this suggests that these domains in their full-length state might be suppressed by the acidic tail.

Further, the inventors confirmed that the identified peptides have therapeutic effect in a damaged skin model.

Based on these findings, the present application provides the following:

[1] a composition for use in stimulating migration of a cell, comprising a substance of any of (a) to (c) below:
(a) a peptide consisting of a portion of an HMGB1 protein and having an activity of stimulating migration of a cell;
(b) a cell secreting the peptide of (a); and
(c) a vector into which a DNA encoding the peptide of (a) is inserted;

[2] A composition for use in mobilizing a cell from bone marrow to peripheral blood, comprising a substance of (a) to (c) below:
(a) a peptide consisting of a portion of an HMGB1 protein and having an activity of stimulating migration of a cell;
(b) a cell secreting the peptide of (a); and
(c) a vector into which a DNA encoding the peptide of (a) is inserted;

[3] a composition for use in regenerating a tissue, comprising a substance of any of (a) to (c) below:
(a) a peptide consisting of a portion of an HMGB1 protein and having an activity of stimulating migration of a cell;
(b) a cell secreting the peptide of (a); and
(c) a vector into which a DNA encoding the peptide described in (a) is inserted;

[4] the composition of any one of embodiments 1-3, wherein the cell stimulated to migrate or mobilized from bone marrow to peripheral blood is a PDGFRα-positive cell:

[5] the composition of any one of embodiments 1-4, wherein the cell stimulated to migrate or mobilized from bone marrow to peripheral blood is a stem cell;

[6] the composition of any one of embodiments 1-5, wherein the cell stimulated to migrate or mobilized from bone marrow to peripheral blood is a bone marrow cell;

[7] the composition of any one of embodiments 1-6, wherein the cell stimulated to migrate or mobilized from bone marrow to peripheral blood is a bone marrow mesenchymal stem cell;

[8] the composition of any one of embodiments 1-7, wherein the peptide consisting of a portion of an HMGB1 protein and having an activity of stimulating migration of a cell is a peptide consisting of the whole or part of the amino acid sequence of positions 1 to 195 or positions 1 to 185 in the amino acid sequence of any one of SEQ ID NOs: 1, 3, and 5, and having an activity of stimulating migration of a cell;

[9] the composition of any one of embodiments 1-7, wherein the peptide consisting of a portion of an HMGB1 protein and having an activity of stimulating migration of a cell is a peptide comprising any of the amino acid sequences below and having an activity of stimulating migration of a cell:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;
(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5; and
(5) the amino acid sequence of position 89 to position 185 in the amino acid sequence of any one of SEQ ID NOs: 1, 3, and 5;

[10] the composition of any one of embodiments 1-7, wherein the peptide consisting of a portion of an HMGB1 protein and having an activity of stimulating migration of a cell is a peptide having an activity of stimulating migration of a cell which consists of the whole or part of the amino acid sequence of positions 1 to 195 or positions 1 to 185 in the amino acid sequence of any one of SEQ ID NOs: 1, 3, and 5, and comprises any of the amino acid sequences below:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;
(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5; and
(5) the amino acid sequence of position 89 to position 185 in the amino acid sequence of any one of SEQ ID NOs: 1, 3, and 5;

[11] a composition for use in stimulating migration of a cell, which comprises a peptide comprising any of the amino acid sequences below and having an activity of stimulating migration of a cell:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;

(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5; and
(5) the amino acid sequence of position 89 to position 185 in the amino acid sequence of any one of SEQ ID NOs: 1, 3, and 5;

[12] a composition for use in mobilizing a cell from bone marrow to peripheral blood, which comprises a peptide comprising any of the amino acid sequences below and having an activity of stimulating migration of a cell:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;
(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5; and
(5) the amino acid sequence of position 89 to position 185 in the amino acid sequence of any one of SEQ ID NOs: 1, 3, and 5;

[13] a composition for in regenerating a tissue, which comprises a peptide comprising any of the amino acid sequences below and having an activity of stimulating migration of a cell:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;
(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5; and
(5) the amino acid sequence of position 89 to position 185 in the amino acid sequence of any one of SEQ ID NOs: 1, 3, and 5;

[14] the composition of any one of embodiments 1-13, wherein the peptide is a synthetic peptide;
[15] the composition of any one of embodiments 1-14, wherein the peptide is a peptide produced using a cell;
[16] the composition of any one of embodiments 1-15, wherein the peptide is a peptide to which a tag is added;
[17] the composition of any one of embodiments 1-15, wherein the peptide is a peptide to which a tag-derived peptide fragment is added;
[18] a peptide that consists of a portion of an HMGB1 protein and has an activity of stimulating migration of a cell;
[19] the peptide of embodiment 18, which is a peptide consisting of the whole or part of the amino acid sequence of positions 1 to 195 or positions 1 to 185 in the amino acid sequence of any one of SEQ ID NOs: 1, 3, and 5, and having an activity of stimulating migration of a cell;
[20] the peptide of embodiment 18, which comprises any of the amino acid sequences below and has an activity of stimulating migration of a cell:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;
(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5;
(5) the amino acid sequence of position 89 to position 185 in the amino acid sequence of any one of SEQ ID NOs: 1, 3, and 5;

[21] the peptide of embodiment 18, which is a peptide having an activity of stimulating migration of a cell which consists of the whole or part of the amino acid sequence of positions 1 to 195 or positions 1 to 185 in the amino acid sequence of any one of SEQ ID NOs: 1, 3, and 5, and comprises any of the amino acid sequences below:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;
(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5;
(5) the amino acid sequence of position 89 to position 185 in the amino acid sequence of any one of SEQ ID NOs: 1, 3, and 5;

[22] a peptide that comprises any of the amino acid sequences below and has an activity of stimulating migration of a cell:
(1) the amino acid sequence of position 17 to position 25 in the amino acid sequence of any one of SEQ ID NOs: 1, 3, and 5;
(2) the amino acid sequence of position 45 to position 74 in the amino acid sequence of any one of SEQ ID NOs: 1, 3, and 5;
(3) the amino acid sequence of position 55 to position 84 in the amino acid sequence of any one of SEQ ID NOs: 1, 3, and 5;
(4) the amino acid sequence of position 85 to position 169 in the amino acid sequence of any one of SEQ ID NOs: 1, 3, and 5;
(5) the amino acid sequence of position 89 to position 185 in the amino acid sequence of any one of SEQ ID NOs: 1, 3, and 5;

[23] the peptide of any one of embodiments 18-22, which is a synthetic peptide;
[24] the peptide of any one of embodiments 18-22, which is a peptide produced using a cell;
[25] the peptide of any one of embodiments 18-22, which is a peptide to which a tag is added;
[26] the peptide of any one of embodiments 18-22, which is a peptide to which a tag-derived peptide fragment is added;
[27] a DNA encoding the peptide of any one of embodiments 18-26;
[28] a vector comprising the DNA of embodiment 27; and

[29] a transformed cell comprising the DNA of embodiment 27 or the vector of embodiment 28.

BRIEF DESCRIPTION OF THE DRAWINGS

FIG. 18B is a photograph showing migration activity of an established PDGFRα-positive bone marrow mesenchymal stem cell line towards HMGB1 fragments. The fragments were all produced using E. coli.

FIG. 18C is a diagram obtained by quantifying migration activity of an established PDGFRα-positive bone marrow mesenchymal stem cell line towards the HMGB1 fragments, and graphing the average values of the respective activities.

FIG. 18D is a table showing the average values of the quantified migration activity of an established PDGFRα-positive bone marrow mesenchymal stem cell line towards the HMGB1 fragments.

MODES FOR CARRYING OUT THE INVENTION

Figure 1:
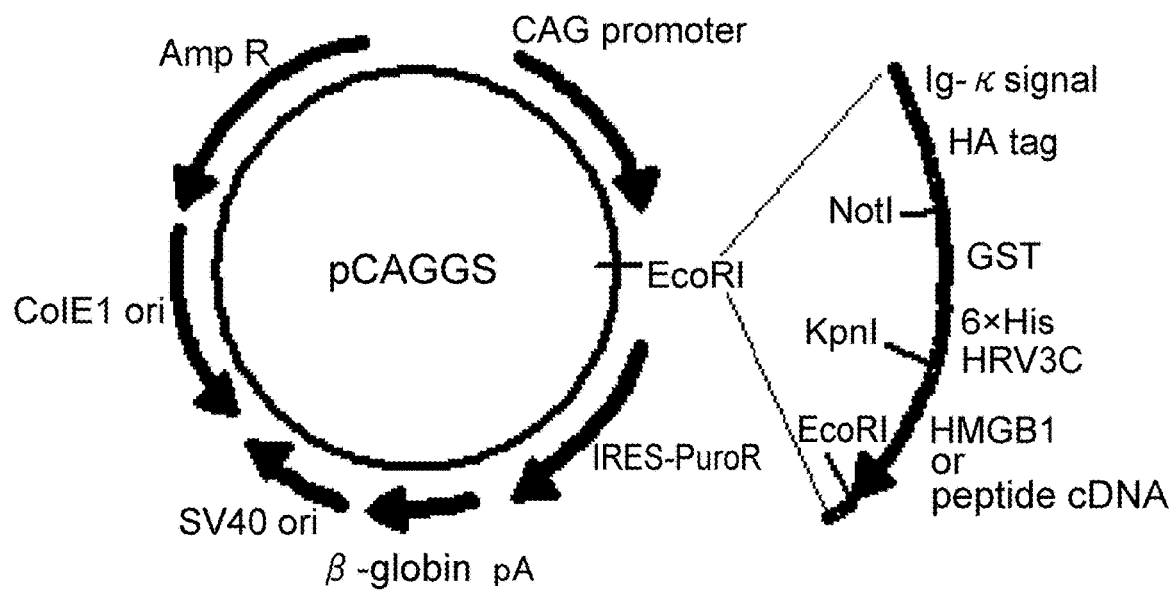
FIG. 1 shows an expression vector for producing peptides and proteins using HEK293 cells.

The present invention provides compositions for use in stimulating cell migration, comprising a substance of any one of (a) to (c) below:
(a) a peptide consisting of a portion of an HMGB1 protein and having cell migration-stimulating activity;
(b) a cell secreting the peptide of (a); and
(c) a vector into which a DNA encoding the peptide of (a) is inserted.

The compositions used for stimulating cell migration in the present invention include reagent compositions and pharmaceutical compositions. In the present specification, reagent compositions are also expressed as reagents, and pharmaceutical compositions are also expressed as pharmaceuticals, agents, or pharmaceutical compositions.

Reagent compositions used for stimulating cell migration in the present invention can be used as reagents needed for basic research and clinical research in, for example, regenerative medicine and development of regeneration-inducing medicine. For example, such reagent compositions can be used to recruit cells to a living tissue in experimental animals, and then evaluate the levels of tissue repair and tissue function reconstruction. Further, such reagent compositions can be used to carry out in vitro research on tissue regeneration by cell recruitment.

Pharmaceutical compositions used for stimulating cell migration in the present invention can be used as pharmaceuticals in, for example, regenerative medicine and regeneration-inducing medicine. For example, such pharmaceutical compositions can be used for tissue regeneration. Also, for example, such pharmaceutical compositions can be used as so-called preventive drugs to prevent the impairment of tissue and organ function due to reduction of tissue stem cells, or alternatively as anti-aging drugs to delay the progression of age-related changes.

In the present specification, compositions used for stimulating cell migration are also expressed as agents used for stimulating cell migration, cell migration-stimulating agents, compositions used for inducing cell migration, agents used for inducing cell migration, cell-migration-inducing agents, or cell-attracting agents.

In the present invention, cell-migration-stimulating activity refers to an activity to stimulate cell migration. In the present specification, cell-migration-stimulating activity is also expressed as cell-migration-inducing activity or cell-attracting activity.

The present invention provides compositions for use in mobilizing bone marrow cells from bone marrow to peripheral blood, comprising a substance of any one of (a) to (c) below:
(a) a peptide consisting of a portion of an HMGB1 protein and having cell-migration-stimulating activity;
(b) a cell secreting the peptide of (a); and
(c) a vector into which a DNA encoding the peptide of (a) is inserted.

The compositions used for mobilizing bone marrow cells from bone marrow to peripheral blood in the present invention include reagent compositions and pharmaceutical compositions.

Reagent compositions used for tissue regeneration in the present invention can be used as reagents needed for basic research and clinical research in, for example, regenerative medicine and development of regeneration-inducing medicine. Pharmaceutical compositions used for tissue regeneration in the present invention can be used as pharmaceuticals in, for example, regenerative medicine and regenerative-inducing medicine. For example, such pharmaceutical compositions can be used to recruit bone marrow tissue stem cells into peripheral circulation and regenerate tissues. Further, it is also possible to collect cells ex vivo that have been recruited into the peripheral blood using said pharmaceutical compositions, and then administer the concentrated cells to a tissue for treatment. Conventional methods are invasive to the living body because cells are collected from the bone marrow which is in the deep part of the body; however, when the pharmaceutical compositions of the present invention are used, bone marrow cells can be collected from peripheral blood less invasively, and used in bone marrow cell transplantation. In the present specification, compositions used for mobilizing bone marrow cells from bone marrow to peripheral blood can be expressed as compositions used for attracting bone marrow cells from bone marrow to peripheral blood.

The present invention provides compositions used for tissue regeneration, comprising a substance of any one of (a) to (c) below:
(a) a peptide consisting of a portion of an HMGB1 protein and having cell-migration-stimulating activity;
(b) a cell secreting the peptide of (a); and
(c) a vector into which a DNA encoding the peptide of (a) is inserted.

The compositions used for tissue regeneration in the present invention include reagent compositions and pharmaceutical compositions.

Reagent compositions used for tissue regeneration in the present invention can be used as reagents needed for basic research and clinical research in, for example, regenerative medicine and development of regeneration-inducing medicine. Pharmaceutical compositions used for tissue regeneration in the present invention can be used as pharmaceuticals in, for example, regenerative medicine and regeneration-inducing medicine.

In the present specification, compositions used for tissue regeneration are also expressed as compositions used for inducing or promoting tissue regeneration, agents used for inducing or promoting tissue regeneration, tissue regeneration-inducing agents or tissue regeneration-promoting agents. Tissue regeneration also includes tissue repair.

Compositions used for tissue regeneration in the present invention can be administered/added to any sites. That is, the compositions can exert their effects no matter which tissue they are administered to, such as a tissue in need of regeneration, a tissue other than a tissue in need of regeneration, or blood. For example, when the compositions are administered/added, cells are recruited to the site of administration/addition or its nearby tissue, thereby inducing or promoting tissue regeneration. Also, for example, when the compositions are administered/added to a damaged tissue site or its nearby region, cells are recruited to the damaged tissue, thereby inducing or promoting tissue regeneration. Further, for example, when the compositions are administered/added to a tissue other than a tissue in need of regeneration, bone marrow cells are mobilized from bone marrow to the tissue in need of regeneration through peripheral circulation, thereby inducing or promoting tissue regeneration. Here, "peripheral circulation" is also called "blood circulation" or "peripheral circulation bloodstream".

The tissue in need of regeneration includes, for example, damaged tissues, necrotic tissues, tissues after surgery, tissues with reduced function, fibrosing tissues, aged tissues, and diseased tissues. Examples of the tissues include live skin tissues and tissues obtained by internal biopsy (surgery) (brain, lung, heart, liver, stomach, small intestine, large intestine, pancreas, kidney, urinary bladder, spleen, uterus, testis, blood, etc.).

Administration to a tissue other than a tissue in need of regeneration refers to administration to a site that is not a site in need of regeneration (a site other than a site in need of regeneration). Accordingly, "a tissue other than a tissue in need of regeneration" can also be referred to as:
a site other than a tissue in need of regeneration; a site other than a site in need of regeneration; a site distant from a tissue in need of regeneration; a site distant from a site in need of regeneration; a site distal to a site in need of regeneration; a tissue distal to a tissue in need of regeneration; a distal site; or a distal tissue.

Thus, compositions of the present invention are effectively used to regenerate tissues (brain, heart, etc.) to which it is difficult to directly administer pharmaceutical agents from outside of the body.

Cells recruited to a tissue in need of regeneration differentiate into various types of cells to contribute to functional regeneration of the tissue in need of regeneration and maintenance/enhancement of the functions. In the present invention, examples of tissue in need of regeneration include, but are not limited to, tissues damaged by various pathological conditions due to ischemic/hypoperfusive/hypoxic conditions, trauma, burns, inflammation, autoimmunity, gene abnormalities, and the like.

Tissues in the present invention are not particularly limited as long as they are tissues into which bone marrow-derived cells can differentiate. Examples include all types of tissues in the living body, such as skin tissue, bone tissue, cartilage tissue, muscle tissue, adipose tissue, cardiac muscle tissue, neurological tissue, pulmonary tissue, gastrointestinal tissues, hepatic/biliary/pancreatic tissues, and genitourinary organs. Moreover, with use of the above compositions, treatments for inducing functional tissue regeneration becomes possible not only in cutaneous diseases such as intractable cutaneous ulcers, skin wounds, bullosis, and alopecia, but also in tissues in need of regeneration such as cerebral infarction, myocardial infarction, bone fracture, pulmonary infarction, gastric ulcers, and enteritis. Animal species to be administered with the above compositions are not particularly limited, and include mammals, birds, fish, and such. Mammals include human and non-human animals, which can be exemplified by, but are not limited to, humans, mice, rats, monkeys, pigs, dogs, rabbits, hamsters, guinea pigs, horses, sheep, and whales.

Examples of the tissue other than a tissue in need of regeneration include blood tissues, muscle tissues, subcutaneous tissues, intradermal tissues, abdominal cavity, and such.

Nerve tissues include central nervous tissues, but are not limited thereto. Compositions used for regenerating nerve tissues can be used to treat, for example, without limitation, cerebral infarction, brain hemorrhage, and brain contusion. Compositions used for regenerating bone tissues can be used to treat, for example, without limitation, bone fracture. In addition, compositions used for regenerating skin tissues can be used to treat, for example, without limitation, skin ulcers, insufficient suture closure of surgical wounds, burns, cuts, bruises, skin erosions, and abrasions.

In the present invention, cells that are stimulated to migrate or cells mobilized from bone marrow to peripheral blood include undifferentiated cells and cells in various stages of differentiation, but are not limited thereto. In the present invention, cells that are stimulated to migrate or cells mobilized from bone marrow to peripheral blood include stem cells, non-stem cells, and such, but are not limited thereto. Stem cells include circulatory stem cells and non-circulatory stem cells. Non-circulatory stem cells are, for example, stem cells residing in a tissue. Circulatory stem cells are, for example, circulatory stem cells in blood.

Further, cells stimulated to migrate or cells mobilized from bone marrow to peripheral blood include bone marrow-derived cells and hematopoietic stem cells, but are not limited thereto. In the present specification, "hematopoietic stem cells" are stem cells that can differentiate into blood cells such as red blood cells, platelets, mast cells, and dendritic cells, as well as white blood cells including neutrophils, eosinophils, basophils, lymphocytes, monocytes, macrophages, and such. Their markers are known to be CD34-positive and CD133-positive in human, and CD34-negative, c-Kit-positive, Sca-1-positive, and lineage marker-negative in mouse. Hematopoietic stem cells are difficult to be cultured alone when cultured in culture dishes, and they need to be co-cultured with stromal cells.

In the present specification, "bone marrow cells" means cells present inside bone marrow while "bone marrow-derived cells" means "bone marrow cells" mobilized from bone marrow to outside of bone marrow. "Bone marrow cells" include cells containing tissue progenitor cell populations present inside bone marrow. Further, "bone marrow-derived cells" may be cells containing mesoangioblasts or cells free of mesoangioblasts.

Tissue progenitor cells are defined as undifferentiated cells having a unidirectional potency to differentiate into cells of a specific tissue other than the blood system, and include undifferentiated cells having the potency to differentiate into mesenchymal tissues, epithelial tissues, nerve tissues, parenchymatous organs, and vascular endothelium as mentioned above.

"Bone marrow cells" and "bone marrow-derived cells" are hematopoietic stem cells and differentiated cells derived therefrom such as leukocytes, erythrocytes, platelets, osteoblasts, and fibrocytes, or are stem cells represented by cells which have been hitherto called bone marrow mesenchymal stem cells, bone marrow stromal pluripotent stem cells, or bone marrow pluripotent stem cells. As used herein, "bone marrow stem cells" refer to stem cells present inside bone marrow, while "bone marrow-derived stem cells" refer to "bone marrow stem cells" mobilized from bone marrow to outside of bone marrow. In the present invention, cells stimulated to migrate or mobilized from bone marrow to peripheral blood include "bone marrow-derived stem cells", but are not limited thereto. "Bone marrow cells" and "bone marrow-derived cells" can be isolated by bone marrow collection (bone marrow cell collection) or peripheral blood collection. Hematopoietic stem cells are nonadherent, while some of the "bone marrow cells" and "bone marrow-derived cells" are obtained as adherent cells by means of a cell culture of a monocyte fraction of blood obtained by the bone marrow collection (bone marrow cell collection) or peripheral blood collection.

Moreover, "bone marrow cells" and "bone marrow-derived cells" include mesenchymal stem cells, and have a potential to differentiate into, preferably, osteoblasts (which can be identified by observing calcification after inducing differentiation), chondrocytes (which can be identified by alcian blue positive staining, safranin O positive staining, or the like), adipocytes (which can be identified by Sudan III positive staining), and other mesenchymal cells such as fibroblasts, smooth muscle cells, stromal cells, and tendon cells; and further nerve cells, epithelial cells (for example, epidermal keratinocytes and intestinal epithelial cells express cytokeratin family), and vascular endothelial cells. The cells to be differentiated into are not limited to the above cells, and the potential to differentiate into cells of parenchymatous organs such as liver, kidney, and pancreas is also included.

Herein, "bone marrow mesenchymal stem cells", "bone marrow stromal pluripotent cells" or "bone marrow pluripotent stem cells" refer to cells existing in the bone marrow, which are directly collected from the bone marrow or indirectly collected from other tissues (blood, skin, fat, and other tissues), and can be cultured and proliferated as adherent cells on a culture dish (made of plastic or glass). These cells are characterized in having a potential to differentiate into mesenchymal tissues such as bone, cartilage, and fat (mesenchymal stem cells), or into skeletal muscle, heart muscle, nervous tissues, and epithelial tissues (pluripotent stem cells), and can be obtained by collection of bone marrow cells.

On the other hand, "bone marrow-derived bone marrow mesenchymal stem cells", "bone marrow-derived bone marrow stromal pluripotent cells", or "bone marrow-derived bone marrow pluripotent stem cells" mobilized from bone marrow to outside of the bone marrow are cells that can be obtained by collection from peripheral blood, mesenchymal tissues such as fat, epithelial tissues such as skin, or nervous tissues such as brain.

In addition, these cells are also characterized in having a potential to differentiate into epithelial tissues such as keratinocytes that constitute skin, or nervous tissues that constitute brain, when administered to a lesion area of the living body immediately after collection or after once being adhered onto a culture dish.

Bone marrow mesenchymal stem cells, bone marrow stromal pluripotent stem cells, bone marrow pluripotent stem cells, or these cells recruited from bone marrow to outside of the bone marrow preferably have a potency to differentiate into: osteoblasts (which can be identified by observing calcification after inducing differentiation), chondrocytes (which can be identified by alcian blue positive staining, safranin O positive staining, or the like), adipocytes (which can be identified by Sudan III positive staining), and other mesenchymal cells such as fibroblasts, smooth muscle cells, skeletal muscle cells, stromal cells, and tendon cells; nerve cells, pigment cells, epidermal cells, hair follicle cells (which express cytokeratin family, hair keratin family, or the like), epithelial cells (for example, epidermal keratinocytes and intestinal epithelial cells express cytokeratin family or the like), and endothelial cells; and further preferably into cells of parenchymatous organs such as liver, kidney, and pancreas. However, differentiated cells are not limited to the above cells.

Human bone marrow cells and human bone marrow-derived cells can be exemplified by, but are not limited to, cells which can be directly obtained by collecting bone marrow (cells), peripheral blood, or fat, or obtained as adherent cells through culturing of an isolated monocyte fraction. Markers for human bone marrow cells and human bone marrow-derived cells include, for example, all or some of the following but are not limited thereto: PDGFRα-positive, Lin-negative, CD45-negative, CD44-positive, CD90-positive, and CD29-positive, Flk-1-negative, CD105-positive, CD73-positive, CD90-positive, CD7-positive, Stro-1-positive, CD106-positive, CD166-positive, and CD31-negative.

Moreover, mouse bone marrow cells and mouse bone marrow-derived cells can be exemplified by, but are not limited to, cells which can be directly obtained by collecting bone marrow (cells), peripheral blood, or fat, or obtained as adherent cells through culturing of an isolated monocyte fraction. Markers for mouse bone marrow cells and mouse bone marrow-derived cells include, for example, all or some of the following but are not limited thereto: CD44-positive, PDGFRα-positive, PDGFRβ-positive, CD45-negative, Lin-negative, Sca-1 positive, c-kit negative, CD90-positive, CD29-positive, and Flk-1-negative.

In the present invention, cells stimulated to migrate or mobilized from bone marrow to peripheral blood are, for example, PDGFRα-positive cells, but are not limited thereto. Further, markers other than PDGFRα can be exemplified by all or some of CD29-positive, CD44-positive, CD90-positive, CD271-positive, CD11b-negative, and Flk-1-negative, but are not limited thereto. PDGFRα-positive cells include, but are not limited to, for example, PDGFRα-positive bone marrow-derived cells, PDGFRα-positive bone marrow-derived bone marrow mesenchymal stem cells, tissue cells residing in PDGFRα-positive tissues (for example, fibroblasts and such), PDGFRα-positive bone marrow-derived cells obtained as adherent cells by means of cell culture of a monocyte fraction of blood obtained by bone marrow collection (bone marrow cell collection) or peripheral blood collection.

Compositions of the present invention may contain substances other than at least one of the substances (a) to (c) mentioned above. In the compositions of the present invention, there is no particular limitation in substances other than at least one of the substances (a) to (c) mentioned above, so long as they do not inhibit the cell migration-stimulating activity, cell mobilization activity, or tissue regeneration promoting activity. For example, in addition to at least one of the substances (a) to (c) mentioned above, the compositions of the present invention may contain: related molecule(s) enhancing the function of substances (a) to (c) mentioned above; molecule(s) which inhibit unanticipated actions of substances (a) to (c) mentioned above; factors which regulate proliferation and differentiation of cells; and other factors which enhance/maintain these factors or cellular functions.

The HMGB1 protein in the present invention includes, but is not limited to, for example, a protein comprising the amino acid sequence of SEQ ID NO: 1 as a human-derived HMGB1 protein, and DNA encoding said protein includes, but is not limited to, for example, a DNA comprising the nucleotide sequence of SEQ ID NO: 2.

Further, the mouse-derived HMGB1 protein includes, but is not limited to, for example, a protein comprising the amino acid sequence of SEQ ID NO: 3, and DNA encoding said protein includes, but is not limited to, for example, a DNA comprising the nucleotide sequence of SEQ ID NO: 4.

Further, the rat-derived HMGB1 protein includes, but is not limited to, for example, a protein comprising the amino acid sequence of SEQ ID NO: 5, and DNA encoding said protein includes, but not limited to, for example, a DNA comprising the nucleotide sequence of SEQ ID NO: 6.

Compositions of the present invention comprise a peptide consisting of a portion of an HMGB1 protein and having cell migration-stimulating activity. The peptide consisting of a portion of an HMGB1 protein of the present invention is not particularly limited as long as it contains a domain having cell migration-stimulating activity.

The cell migration-stimulating activity of a peptide consisting of a portion of an HMGB1 protein can be verified by, for example, methods described in the Examples and methods shown below, without limitation; and it can also be measured using another in vitro or in vivo method for measuring cell migration ability.

Method in which a silicone tube inserted with an HMGB1 protein or peptide is implanted under the skin and such, and taken out after a certain period of time to observe cells that migrate into the tube.

Method in which resin beads and the like bound to an HMGB1 protein or peptide are implanted in a body tissue, and taken out after a certain period of time to observe cells that migrate into the beads.

Method in which polymers that have a sustained release action, such as gelatin and hyaluronic acid, are impregnated with an HMGB1 protein or peptide and implanted in a body tissue, and taken out after a certain period of time to observe cells that migrate into the polymers.

In the present invention, the peptide consisting of a portion of an HMGB1 protein and having cell migration-stimulating activity can be exemplified by the peptides below, but are not limited thereto.

In the present invention, the peptide consisting of a portion of an HMGB1 protein and having cell migration-stimulating activity includes, for example, a peptide having an activity of mobilizing cells from bone marrow to peripheral blood, or an activity of promoting tissue regeneration.

In the present invention, the peptide consisting of a portion of an HMGB1 protein and having cell migration-stimulating activity includes, for example, a peptide consisting of the whole or part of the amino acid sequence of positions 1 to 195 or positions 1 to 185 in the amino acid sequence of any of SEQ ID NOs: 1, 3, and 5, and having cell migration-stimulating activity.

In the present invention, the peptide consisting of a portion of an HMGB1 protein and having cell migration-stimulating activity includes, for example, a peptide that comprises at least any one of the amino acid sequences below and has cell migration-stimulating activity. The following amino acid sequences are part of the amino acid sequence of any of SEQ ID NOs: 1, 3, and 5:
(1) the amino acid sequence of position 17 to position 25;
(2) the amino acid sequence of position 45 to position 74;
(3) the amino acid sequence of position 55 to position 84;

(4) the amino acid sequence of position 85 to position 169;
(5) the amino acid sequence of position 89 to position 185; and
(6) the amino acid sequence of position 93 to position 215.

In the present invention, the peptide consisting of a portion of an HMGB1 protein and having cell migration-stimulating activity includes a peptide having cell migration-stimulating activity which consists of the whole or part of the amino acid sequence of positions 1 to 195 or positions 1 to 185 in the amino acid sequence of any one of SEQ ID NOs: 1, 3, and 5, wherein the peptide comprises at least any one of the amino acid sequences below. The following amino acid sequences are part of the amino acid sequence of any one of SEQ ID NOs: 1, 3, and 5:
(1) a peptide comprising the amino acid sequence of position 17 to position 25;
(2) a peptide comprising the amino acid sequence of position 45 to position 74;
(3) a peptide comprising the amino acid sequence of position 55 to position 84;
(4) a peptide comprising the amino acid sequence of position 85 to position 169; and
(5) a peptide comprising the amino acid sequence of position 89 to position 185.

In the present invention, the peptide consisting of a portion of an HMGB1 protein and having cell migration-stimulating activity includes a peptide having cell migration-stimulating activity which consists of a portion of the amino acid sequence of any one of SEQ ID NOs: 1, 3, and 5, wherein the peptide comprises at least the amino acid sequence of position 17 to position 25 in the amino acid sequence of any one of SEQ ID NOs: 1, 3, and 5. Examples of such peptides include, but are not limited to, a peptide consisting of the whole or part of the amino acid sequence of positions 1 to 195 in the amino acid sequence of any one of SEQ ID NOs: 1, 3, and 5 (the number of amino acids in said peptide is an amino acid number selected from natural numbers less than or equal to 195), a peptide consisting of the whole or part of the amino acid sequence of positions 1 to 185 in the amino acid sequence of any one of SEQ ID NOs: 1, 3, and 5 (the number of amino acids in said peptide is an amino acid number selected from natural numbers less than or equal to 185), a peptide consisting of the whole or part of the amino acid sequence of positions 1 to 170 in the amino acid sequence of any one of SEQ ID NOs: 1, 3, and 5 (the number of amino acids in said peptide is an amino acid number selected from natural numbers less than or equal to 170), a peptide consisting of the whole or part of the amino acid sequence of positions 1 to 84 in the amino acid sequence of any one of SEQ ID NOs: 1, 3, and 5 (the number of amino acids in said peptide is an amino acid number selected from natural numbers less than or equal to 84), a peptide consisting of the whole or part of the amino acid sequence of positions 1 to 44 in the amino acid sequence of any one of SEQ ID NOs: 1, 3, and 5 (the number of amino acids in said peptide is an amino acid number selected from natural numbers less than or equal to 44), wherein the peptide comprises at least the amino acid sequence of positions 17 to 25 in said amino acid sequence and has cell migration-stimulating activity.

The following description is regarding "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 17 to position 25 in said amino acid sequence". However, other peptides included in said peptide, such as "a peptide having cell migration-stimulating activity which consists of the whole or part of the amino acid sequence of positions 1 to 185 in the amino acid sequence of any one of SEQ ID NOs: 1, 3, and 5, and wherein the peptide comprises at least the amino acid sequence of position 17 to position 25 in said amino acid sequence", can also be described similarly.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 17 to position 25 in said amino acid sequence" may also be expressed as "a peptide having cell migration-stimulating activity which consists of a consecutive amino acid sequence selected from the amino acid sequence of positions 1 to 195 in the amino acid sequence of any one of SEQ ID NOs: 1, 3, and 5, wherein the peptide comprises at least the amino acid sequence of position 17 to position 25 in said amino acid sequence".

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 17 to position 25 in said amino acid sequence" includes a peptide having cell migration-stimulating activity which consists of the whole or part of the amino acid sequence of any one of (1) to (60) shown below, and comprises at least the amino acid sequence of position 17 to position 25 in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 17 to position 25 in said amino acid sequence" includes a peptide having cell migration-stimulating activity which consists of the whole or part of the amino acid sequence of position 1 to position 195 in the amino acid sequence of any one of SEQ ID NOs: 1, 3, and 5, wherein the peptide comprises at least the amino acid sequence of any one of (1) to (57) and (59) to (61) shown below in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 17 to position 25 in said amino acid sequence" includes a peptide having cell migration-stimulating activity which consists of the amino acid sequence of any one of (1) to (61) shown below. The following amino acid sequences are part of the amino acid sequence of any one of SEQ ID NOs: 1, 3, and 5:
(1) the amino acid sequence of position 1 to position 44;
(2) the amino acid sequence of position 1 to position 25;
(3) the amino acid sequence of position 1 to position 34;
(4) the amino acid sequence of position 1 to position 42;
(5) the amino acid sequence of position 1 to position 43;
(6) the amino acid sequence of position 1 to position 45;
(7) the amino acid sequence of position 1 to position 46;
(8) the amino acid sequence of position 1 to position 47;
(9) the amino acid sequence of position 1 to position 48;
(10) the amino acid sequence of position 1 to position 49;

(11) the amino acid sequence of position 1 to position 50;
(12) the amino acid sequence of position 1 to position 51;
(13) the amino acid sequence of position 1 to position 52;
(14) the amino acid sequence of position 1 to position 62;
(15) the amino acid sequence of position 1 to position 84;
(16) the amino acid sequence of position 10 to position 25;
(17) the amino acid sequence of position 11 to position 25;
(18) the amino acid sequence of position 11 to position 27;
(19) the amino acid sequence of position 11 to position 28;
(20) the amino acid sequence of position 11 to position 29;
(21) the amino acid sequence of position 11 to position 30;
(22) the amino acid sequence of position 11 to position 34;
(23) the amino acid sequence of position 11 to position 44;
(24) the amino acid sequence of position 12 to position 25;
(25) the amino acid sequence of position 12 to position 30;
(26) the amino acid sequence of position 13 to position 25;
(27) the amino acid sequence of position 13 to position 30;
(28) the amino acid sequence of position 14 to position 25;
(29) the amino acid sequence of position 14 to position 30;
(30) the amino acid sequence of position 15 to position 25;
(31) the amino acid sequence of position 15 to position 30;
(32) the amino acid sequence of position 16 to position 25;
(33) the amino acid sequence of position 16 to position 30;
(34) the amino acid sequence of position 17 to position 30;
(35) the amino acid sequence of position 1 to position 70;
(36) the amino acid sequence of position 1 to position 81;
(37) the amino acid sequence of position 1 to position 170;
(38) the amino acid sequence of position 2 to position 25;
(39) the amino acid sequence of position 2 to position 34;
(40) the amino acid sequence of position 2 to position 42;
(41) the amino acid sequence of position 2 to position 43;
(42) the amino acid sequence of position 2 to position 44;
(43) the amino acid sequence of position 2 to position 45;
(44) the amino acid sequence of position 2 to position 46;
(45) the amino acid sequence of position 2 to position 47;
(46) the amino acid sequence of position 2 to position 48;
(47) the amino acid sequence of position 2 to position 49;
(48) the amino acid sequence of position 2 to position 50;
(49) the amino acid sequence of position 2 to position 51;
(50) the amino acid sequence of position 2 to position 52;
(51) the amino acid sequence of position 2 to position 62;
(52) the amino acid sequence of position 2 to position 70;
(53) the amino acid sequence of position 2 to position 81;
(54) the amino acid sequence of position 2 to position 84;
(55) the amino acid sequence of position 2 to position 170;
(56) the amino acid sequence of position 17 to position 44;
(57) the amino acid sequence of position 1 to position 185;
(58) the amino acid sequence of position 1 to position 195;
(59) the amino acid sequence of position 2 to position 185;
(60) the amino acid sequence of position 2 to position 195; and
(61) the amino acid sequence of position 17 to position 25.

In the present invention, the peptide consisting of a portion of an HMGB1 protein and having cell migration-stimulating activity includes a peptide having cell migration-stimulating activity which consists of a portion of the amino acid sequence of any one of SEQ ID NOs: 1, 3, and 5, wherein the peptide comprises at least the amino acid sequence of position 45 to position 74 in the amino acid sequence of any one of SEQ ID NOs: 1, 3, and 5. Examples of such peptides include, but are not limited to, a peptide consisting of the whole or part of the amino acid sequence of positions 1 to 195 in the amino acid sequence of any one of SEQ ID NOs: 1, 3, and 5 (the number of amino acids in said peptide is an amino acid number selected from natural numbers less than or equal to 195), a peptide consisting of the whole or part of the amino acid sequence of positions 1 to 185 in the amino acid sequence of any one of SEQ ID NOs: 1, 3, and 5 (the number of amino acids in said peptide is an amino acid number selected from natural numbers less than or equal to 185), a peptide consisting of the whole or part of the amino acid sequence of positions 1 to 170 in the amino acid sequence of any one of SEQ ID NOs: 1, 3, and 5 (the number of amino acids in said peptide is an amino acid number selected from natural numbers less than or equal to 170), a peptide consisting of the whole or part of the amino acid sequence of positions 1 to 84 in the amino acid sequence of any one of SEQ ID NOs: 1, 3, and 5 (the number of amino acids in said peptide is an amino acid number selected from natural numbers less than or equal to 84), a peptide consisting of the whole or part of the amino acid sequence of positions 45 to 84 in the amino acid sequence of any one of SEQ ID NOs: 1, 3, and 5 (the number of amino acids in said peptide is an amino acid number selected from natural numbers less than or equal to 40), wherein the peptide comprises at least the amino acid sequence of positions 45 to 74 in said amino acid sequence and has cell migration-stimulating activity.

The following description is regarding "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 45 to position 74 in said amino acid sequence". However, other peptides included in said peptide, such as "a peptide having cell migration-stimulating activity consisting of the whole or part of the amino acid sequence of positions 1 to 185 in the amino acid sequence of any one of SEQ ID NOs: 1, 3, and 5, wherein the peptide comprises at least the amino acid sequence of position 45 to position 74 in said amino acid sequence", can also be described similarly.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 45 to position 74 in said amino acid sequence" may also be expressed as "a peptide having cell migration-stimulating activity which consists of a consecutive amino acid sequence selected from the amino acid sequence of positions 1 to 195 in the amino acid sequence of any one of SEQ ID NOs: 1, 3, and 5, wherein the peptide comprises at least the amino acid sequence of position 45 to position 74 in said amino acid sequence".

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 45 to position 74 in said amino acid sequence" includes a peptide having cell migration-stimulating activity which consists of the whole or part of the amino acid sequence of any one of (a) to (k) below, and comprises at least the amino acid sequence of position 45 to position 74 in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 45 to position 74 in said amino acid sequence" includes a peptide having cell migration-stimulating activity which consists of the whole or part of the amino acid sequence of position 1 to position 195 in the amino acid sequence of any one of SEQ ID NOs: 1, 3, and 5, wherein the peptide comprises at least the amino acid sequence of any one of (a) to (h) and (j) to (l) in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 45 to position 74 in said amino acid sequence" includes a peptide having cell migration-stimulating activity which consists of the amino acid sequence of any one of (a) to (1). The following amino acid sequences are part of the amino acid sequence of any one of SEQ ID NOs: 1, 3, and 5:

(a) the amino acid sequence of position 1 to position 84;
(b) the amino acid sequence of position 45 to position 84;
(c) the amino acid sequence of position 1 to position 81;
(d) the amino acid sequence of position 1 to position 170;
(e) the amino acid sequence of position 2 to position 81;
(f) the amino acid sequence of position 2 to position 84;
(g) the amino acid sequence of position 2 to position 170;
(h) the amino acid sequence of position 1 to position 185;
(i) the amino acid sequence of position 1 to position 195;
(j) the amino acid sequence of position 2 to position 185;
(k) the amino acid sequence of position 2 to position 195; and
(l) the amino acid sequence of position 45 to position 74.

In the present invention, the peptide consisting of a portion of an HMGB1 protein and having cell migration-stimulating activity is a peptide having cell migration-stimulating activity which consists of a portion of the amino acid sequence of any one of SEQ ID NOs: 1, 3, and 5, wherein the peptide comprises at least the amino acid sequence of position 55 to position 84 in the amino acid sequence of any one of SEQ ID NOs: 1, 3, and 5.

Examples of such peptides include, but are not limited to, a peptide consisting of the whole or part of the amino acid sequence of positions 1 to 195 in the amino acid sequence of any one of SEQ ID NOs: 1, 3, and 5 (the number of amino acids in said peptide is an amino acid number selected from natural numbers less than or equal to 195), a peptide consisting of the whole or part of the amino acid sequence of positions 1 to 185 in the amino acid sequence of any one of SEQ ID NOs: 1, 3, and 5 (the number of amino acids in said peptide is an amino acid number selected from natural numbers less than or equal to 185), a peptide consisting of the whole or part of the amino acid sequence of positions 1 to 170 in the amino acid sequence of any one of SEQ ID NOs: 1, 3, and 5 (the number of amino acids in said peptide is an amino acid number selected from natural numbers less than or equal to 170), a peptide consisting of the whole or part of the amino acid sequence of positions 1 to 84 in the amino acid sequence of any one of SEQ ID NOs: 1, 3, and 5 (the number of amino acids in said peptide is an amino acid number selected from natural numbers less than or equal to 84), a peptide consisting of the whole or part of the amino acid sequence of positions 45 to 84 in the amino acid sequence of any one of SEQ ID NOs: 1, 3, and 5 (the number of amino acids in said peptide is an amino acid number selected from natural numbers less than or equal to 40), wherein the peptide comprises at least the amino acid sequence of positions 55 to 84 in said amino acid sequence and has cell migration-stimulating activity.

The following description is regarding "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 55 to position 84 in said amino acid sequence". However, other peptides included in said peptide, such as "a peptide having cell migration-stimulating activity which consists of the whole or part of the amino acid sequence of positions 1 to 185 in the amino acid sequence of any one of SEQ ID NOs: 1, 3, and 5, wherein the peptide comprises at least the amino acid sequence of position 55 to position 84 in said amino acid sequence", can also be described similarly.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 55 to position 84 in said amino acid sequence" may also be expressed as "a peptide having cell migration-stimulating activity which consists of a consecutive amino acid sequence selected from the amino acid sequence of positions 1 to 195 in the amino acid sequence of any one of SEQ ID NOs: 1, 3, and 5, wherein the peptide comprises at least the amino acid sequence of position 55 to position 84 in said amino acid sequence".

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 55 to position 84 in said amino acid sequence" includes a peptide having cell migration-stimulating activity which consists of the whole or part of the amino acid sequence of any of (A) to (J) below, and comprises at least the amino acid sequence of position 55 to position 84 in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 55 to position 84 in said amino acid sequence" includes a peptide having cell migration-stimulating activity which consists of the whole or part of the amino acid sequence of position 1 to position 195 in the amino acid sequence of any one of SEQ ID NOs: 1, 3, and 5, wherein the peptide comprises at least the amino acid sequence of any one of (A) to (G) and (I) to (K) below in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 55 to position 84 in said amino acid sequence" includes a peptide having cell migration-stimulating activity which consists of the amino acid sequence of any one of (A) to (K) below. The following amino acid sequences are part of the amino acid sequence of any one of SEQ ID NOs: 1, 3, and 5:

(A) the amino acid sequence of position 1 to position 84;
(B) the amino acid sequence of position 45 to position 84;
(C) the amino acid sequence of position 1 to position 170;

(D) the amino acid sequence of position 2 to position 84;
(F) a peptide comprising the amino acid sequence of position 2 to position 170;
(G) the amino acid sequence of position 1 to position 185;
(H) the amino acid sequence of position 1 to position 195;
(I) the amino acid sequence of position 2 to position 185;
(J) the amino acid sequence of position 2 to position 195; and
(K) the amino acid sequence of position 55 to position 84.

In the present invention, the peptide consisting of a portion of an HMGB1 protein and having cell migration-stimulating activity is a peptide having cell migration-stimulating activity which consists of a portion of the amino acid sequence of any one of SEQ ID NOs: 1, 3, and 5, wherein the peptide comprises at least the amino acid sequence of position 85 to position 169 in the amino acid sequence of any one of SEQ ID NOs: 1, 3, and 5.

Examples of such peptides include, but are not limited to, a peptide consisting of the whole or part of the amino acid sequence of positions 1 to 195 in the amino acid sequence of any one of SEQ ID NOs: 1, 3, and 5 (the number of amino acids in said peptide is an amino acid number selected from natural numbers less than or equal to 195), a peptide consisting of the whole or part of the amino acid sequence of positions 1 to 185 in the amino acid sequence of any one of SEQ ID NOs: 1, 3, and 5 (the number of amino acids in said peptide is an amino acid number selected from natural numbers less than or equal to 185), a peptide consisting of the whole or part of the amino acid sequence of positions 1 to 170 in the amino acid sequence of any one of SEQ ID NOs: 1, 3, and 5 (the number of amino acids in said peptide is an amino acid number selected from natural numbers less than or equal to 170), a peptide consisting of the whole or part of the amino acid sequence of positions 89 to 185 in the amino acid sequence of any one of SEQ ID NOs: 1, 3, and 5 (the number of amino acids in said peptide is an amino acid number selected from natural numbers less than or equal to 101), wherein the peptide comprises at least the amino acid sequence of positions 85 to 169 in said amino acid sequence and has cell migration-stimulating activity.

The following description is regarding "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 85 to position 169 in said amino acid sequence". However, other peptides included in said peptide, such as "a peptide having cell migration-stimulating activity which consists of the whole or part of the amino acid sequence of positions 1 to 185 in the amino acid sequence of any one of SEQ ID NOs: 1, 3, and 5, wherein the peptide comprises at least the amino acid sequence of position 85 to position 169 in said amino acid sequence", can also be described similarly.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 85 to position 169 in said amino acid sequence" may also be expressed as "a peptide having cell migration-stimulating activity which consists of a consecutive amino acid sequence selected from the amino acid sequence of positions 1 to 195 in the amino acid sequence of any one of SEQ ID NOs: 1, 3, and 5, wherein the peptide comprises at least the amino acid sequence of position 85 to position 169 in said amino acid sequence".

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 85 to position 169 in said amino acid sequence" includes a peptide having cell migration-stimulating activity which consists of the whole or part of the amino acid sequence of any one of (i) to (vi) below, and comprises at least the amino acid sequence of position 85 to position 169 in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 85 to position 169 in said amino acid sequence" includes a peptide having cell migration-stimulating activity which consists of the whole or part of the amino acid sequence of position 1 to position 195 in the amino acid sequence of any one of SEQ ID NOs: 1, 3, and 5, wherein the peptide comprises at least the amino acid sequence of any one of (i) to (iii) and (v) to (vii) below in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 85 to position 169 in said amino acid sequence" includes a peptide having cell migration-stimulating activity which consists of the amino acid sequence of any one of (i) to (vii) below. The following amino acid sequences are part of the amino acid sequence of any one of SEQ ID NOs: 1, 3, and 5:
(i) the amino acid sequence of position 1 to position 170;
(ii) the amino acid sequence of position 2 to position 170;
(iii) the amino acid sequence of position 1 to position 185;
(iv) the amino acid sequence of position 1 to position 195;
(v) the amino acid sequence of position 2 to position 185;
(vi) the amino acid sequence of position 2 to position 195; and
(vii) position 85 to position 169.

In the present invention, the peptide consisting of a portion of an HMGB1 protein and having cell migration-stimulating activity includes a peptide having cell migration-stimulating activity which consists of a portion of the amino acid sequence of any one of SEQ ID NOs: 1, 3, and 5, wherein the peptide comprises at least the amino acid sequence of position 89 to position 185 in the amino acid sequence of any one of SEQ ID NOs: 1, 3, and 5. Examples of such peptides include, but are not limited to, a peptide consisting of the whole or part of the amino acid sequence of positions 1 to 195 in the amino acid sequence of any one of SEQ ID NOs: 1, 3, and 5 (the number of amino acids in said peptide is an amino acid number selected from natural numbers less than or equal to 195), and a peptide consisting of the whole or part of the amino acid sequence of positions 1 to 185 in the amino acid sequence of any one of SEQ ID NOs: 1, 3, and 5 (the number of amino acids in said peptide is an amino acid number selected from natural numbers less than or equal to 185), wherein the peptide comprises at least the amino acid sequence of positions 89 to 185 in said amino acid sequence and has cell migration-stimulating activity.

The following description is regarding "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 89 to position 185 in said amino acid sequence". However, other peptides included in said peptide, such as "a peptide having cell migration-stimulating activity which consists of the whole or part of the amino acid sequence of positions 1 to 185 in the amino acid sequence of any one of SEQ ID NOs: 1, 3, and 5, wherein the peptide comprises at least the amino acid sequence of position 89 to position 185 in said amino acid sequence", can also be described similarly.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 89 to position 185 in said amino acid sequence" may also be expressed as "a peptide having cell migration-stimulating activity which consists of a consecutive amino acid sequence selected from the amino acid sequence of positions 1 to 195 in the amino acid sequence of any one of SEQ ID NOs: 1, 3, and 5, wherein the peptide comprises at least the amino acid sequence of position 89 to position 185 in said amino acid sequence".

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 89 to position 185 in said amino acid sequence" includes a peptide having cell migration-stimulating activity which consists of the whole or part of the amino acid sequence of any one of (I) to (VI) below, wherein the peptide comprises at least the amino acid sequence of position 89 to position 185 in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 89 to position 185 in said amino acid sequence" includes a peptide having cell migration-stimulating activity which consists of the whole or part of the amino acid sequence of position 1 to position 195 in the amino acid sequence of any one of SEQ ID NOs: 1, 3, and 5, wherein the peptide comprises at least the amino acid sequence of any one of (I) and (III) to (V) in the amino acid sequence of any one of SEQ ID NOs: 1, 3, and 5.

In the present invention, "a peptide having cell migration-stimulating activity which consists of the whole or part of the amino acid sequence of positions 1 to 195 in the amino acid sequence of any one of SEQ ID NOs: 1, 3, and 5, wherein the peptide comprises at least the amino acid sequence of position 89 to position 185 in said amino acid sequence" includes a peptide having cell migration-stimulating activity which consists of the amino acid sequence of any one of (I) to (V) below. The following amino acid sequences are part of the amino acid sequence of any one of SEQ ID NOs: 1, 3, and 5:
(I) the amino acid sequence of position 1 to position 185;
(II) the amino acid sequence of position 1 to position 195;
(III) the amino acid sequence of position 2 to position 185;
(IV) the amino acid sequence of position 2 to position 195; and
(V) the amino acid sequence of position 89 to position 185.

In the present invention, the peptide consisting of a portion of an HMGB1 protein and having cell migration-stimulating activity is a peptide having cell migration-stimulating activity which consists of a portion of the amino acid sequence of any one of SEQ ID NOs: 1, 3, and 5, wherein the peptide comprises at least the amino acid sequence of position 93 to position 215 in the amino acid sequence of any one of SEQ ID NOs: 1, 3, and 5.

Examples of such peptides include, but are not limited to, a peptide consisting of the whole or part of the amino acid sequence of positions 45 to 215 in the amino acid sequence of any one of SEQ ID NOs: 1, 3, and 5 (the number of amino acids in said peptide is an amino acid number selected from natural numbers less than or equal to 171), a peptide consisting of the whole or part of the amino acid sequence of positions 63 to 215 in the amino acid sequence of any one of SEQ ID NOs: 1, 3, and 5 (the number of amino acids in said peptide is an amino acid number selected from natural numbers less than or equal to 153), and a peptide consisting of the whole or part of the amino acid sequence of positions 89 to 215 in the amino acid sequence of any one of SEQ ID NOs: 1, 3, and 5 (the number of amino acids in said peptide is an amino acid number selected from natural numbers less than or equal to 123), wherein the peptide comprises at least the amino acid sequence of positions 93 to 215 in said amino acid sequence and has cell migration-stimulating activity.

The following description is regarding "a peptide having cell migration-stimulating activity which consists of the whole or part of the amino acid sequence of positions 45 to 215 in the amino acid sequence of any one of SEQ ID NOs: 1, 3, and 5, wherein the peptide comprises at least the amino acid sequence of position 93 to position 215 in said amino acid sequence". However, other peptides included in said peptide, such as "a peptide having cell migration-stimulating activity which consists of the whole or part of the amino acid sequence of positions 63 to 215 in the amino acid sequence of any one of SEQ ID NOs: 1, 3, and 5, wherein the peptide comprises at least the amino acid sequence of position 89 to position 215 in said amino acid sequence" can also be described similarly.

In the present invention, "a peptide having cell migration-stimulating activity which consists of the whole or part of the amino acid sequence of positions 45 to 215 in the amino acid sequence of any one of SEQ ID NOs: 1, 3, and 5, wherein the peptide comprises at least the amino acid sequence of position 93 to position 215 in said amino acid sequence" may also be expressed as "a peptide having cell migration-stimulating activity which consists of a consecutive amino acid sequence selected from the amino acid sequence of positions 45 to 215 in the amino acid sequence of any one of SEQ ID NOs: 1, 3, and 5, wherein the peptide comprises at least the amino acid sequence of position 93 to position 215 in said amino acid sequence".

In the present invention, "a peptide having cell migration-stimulating activity which consists of the whole or part of the amino acid sequence of positions 45 to 215 in the amino acid sequence of any one of SEQ ID NOs: 1, 3, and 5, wherein the peptide comprises at least the amino acid sequence of position 93 to position 215 in said amino acid sequence" includes a peptide having cell migration-stimulating activity which consists of the whole or part of the amino acid sequence of any one of (W) to (Y) below, wherein the peptide comprises at least the amino acid sequence of position 93 to position 215 in the amino acid sequence of any one of SEQ ID NOs: 1, 3, and 5.

In the present invention, "a peptide having cell migration-stimulating activity which consists of the whole or part of the amino acid sequence of positions 45 to 215 in the amino acid sequence of any one of SEQ ID NOs: 1, 3, and 5, wherein the peptide comprises at least the amino acid sequence of position 93 to position 215 in said amino acid sequence" includes a peptide having cell migration-stimulating activity which consists of the whole or part of the amino acid sequence of position 45 to position 215 in the amino acid sequence of any one of SEQ ID NOs: 1, 3, and 5, wherein the peptide comprises at least the amino acid sequence of any one of (X) to (Z) below in the amino acid sequence of any one of SEQ ID NOs: 1, 3, and 5.

In the present invention, "a peptide having cell migration-stimulating activity which consists of the whole or part of the amino acid sequence of positions 45 to 215 in the amino acid sequence of any one of SEQ ID NOs: 1, 3, and 5, wherein the peptide comprises at least the amino acid sequence of position 93 to position 215 in said amino acid sequence" includes a peptide having cell migration-stimulating activity which consists of the amino acid sequence of any one of (W) to (Z) below. The following amino acid sequences are part of the amino acid sequence of any one of SEQ ID NOs: 1, 3, and 5:

(W) a peptide comprising the amino acid sequence of position 45 to position 215;
(X) a peptide comprising the amino acid sequence of position 63 to position 215;
(Y) a peptide comprising the amino acid sequence of position 89 to position 215; and
(Z) a peptide comprising the amino acid sequence of position 93 to position 215.

Thus, the peptide consisting of a portion of an HMGB1 protein and having cell migration-stimulating activity in the present invention includes, but is not limited to, the following peptides:

<1> a peptide comprising the amino acid sequence of position 1 to position 44;
<2> a peptide comprising the amino acid sequence of position 1 to position 25;
<3> a peptide comprising the amino acid sequence of position 1 to position 34;
<4> a peptide comprising the amino acid sequence of position 1 to position 42;
<5> a peptide comprising the amino acid sequence of position 1 to position 43;
<6> a peptide comprising the amino acid sequence of position 1 to position 45;
<7> a peptide comprising the amino acid sequence of position 1 to position 46;
<8> a peptide comprising the amino acid sequence of position 1 to position 47;
<9> a peptide comprising the amino acid sequence of position 1 to position 48;
<10> a peptide comprising the amino acid sequence of position 1 to position 49;
<11> a peptide comprising the amino acid sequence of position 1 to position 50;
<12> a peptide comprising the amino acid sequence of position 1 to position 51;
<13> a peptide comprising the amino acid sequence of position 1 to position 52;
<14> a peptide comprising the amino acid sequence of position 1 to position 62;
<15> a peptide comprising the amino acid sequence of position 1 to position 84;
<16> a peptide comprising the amino acid sequence of position 10 to position 25;
<17> a peptide comprising the amino acid sequence of position 11 to position 25;
<18> a peptide comprising the amino acid sequence of position 11 to position 27;
<19> a peptide comprising the amino acid sequence of position 11 to position 28;
<20> a peptide comprising the amino acid sequence of position 11 to position 29;
<21> a peptide comprising the amino acid sequence of position 11 to position 30;
<22> a peptide comprising the amino acid sequence of position 11 to position 34;
<23> a peptide comprising the amino acid sequence of position 11 to position 44;
<24> a peptide comprising the amino acid sequence of position 12 to position 25;
<25> a peptide comprising the amino acid sequence of position 12 to position 30;
<26> a peptide comprising the amino acid sequence of position 13 to position 25;
<27> a peptide comprising the amino acid sequence of position 13 to position 30;
<28> a peptide comprising the amino acid sequence of position 14 to position 25;
<29> a peptide comprising the amino acid sequence of position 14 to position 30;
<30> a peptide comprising the amino acid sequence of position 15 to position 25;
<31> a peptide comprising the amino acid sequence of position 15 to position 30;
<32> a peptide comprising the amino acid sequence of position 16 to position 25;
<33> a peptide comprising the amino acid sequence of position 16 to position 30;
<34> a peptide comprising the amino acid sequence of position 17 to position 25;
<35> a peptide comprising the amino acid sequence of position 17 to position 30;
<36> a peptide comprising the amino acid sequence of position 45 to position 74;
<37> a peptide comprising the amino acid sequence of position 45 to position 84;
<38> a peptide comprising the amino acid sequence of position 45 to position 215;
<39> a peptide comprising the amino acid sequence of position 55 to position 84;
<40> a peptide comprising the amino acid sequence of position 63 to position 215;
<41> a peptide comprising the amino acid sequence of position 1 to position 70;
<42> a peptide comprising the amino acid sequence of position 1 to position 81;
<43> a peptide comprising the amino acid sequence of position 1 to position 170;
<44> a peptide comprising the amino acid sequence of position 2 to position 25;
<45> a peptide comprising the amino acid sequence of position 2 to position 34;
<46> a peptide comprising the amino acid sequence of position 2 to position 42;
<47> a peptide comprising the amino acid sequence of position 2 to position 43;

<48> a peptide comprising the amino acid sequence of position 2 to position 44;
<49> a peptide comprising the amino acid sequence of position 2 to position 45;
<50> a peptide comprising the amino acid sequence of position 2 to position 46;
<51> a peptide comprising the amino acid sequence of position 2 to position 47;
<52> a peptide comprising the amino acid sequence of position 2 to position 48;
<53> a peptide comprising the amino acid sequence of position 2 to position 49;
<54> a peptide comprising the amino acid sequence of position 2 to position 50;
<55> a peptide comprising the amino acid sequence of position 2 to position 51;
<56> a peptide comprising the amino acid sequence of position 2 to position 52;
<57> a peptide comprising the amino acid sequence of position 2 to position 62;
<58> a peptide comprising the amino acid sequence of position 2 to position 70;
<59> a peptide comprising the amino acid sequence of position 2 to position 81;
<60> a peptide comprising the amino acid sequence of position 2 to position 84;
<61> a peptide comprising the amino acid sequence of position 2 to position 170;
<62> a peptide comprising the amino acid sequence of position 85 to position 169;
<63> a peptide comprising the amino acid sequence of position 89 to position 185;
<64> a peptide comprising the amino acid sequence of position 89 to position 195;
<65> a peptide comprising the amino acid sequence of position 89 to position 205;
<66> a peptide comprising the amino acid sequence of position 89 to position 215;
<67> a peptide comprising the amino acid sequence of position 93 to position 215;
<68> a peptide comprising the amino acid sequence of position 17 to position 44;
<69> a peptide comprising the amino acid sequence of position 1 to position 185;
<70> a peptide comprising the amino acid sequence of position 1 to position 195;
<71> a peptide comprising the amino acid sequence of position 1 to position 205;
<72> a peptide comprising the amino acid sequence of position 2 to position 185;
<73> a peptide comprising the amino acid sequence of position 2 to position 195; and
<74> a peptide comprising the amino acid sequence of position 2 to position 205.

Further, in the present invention, peptides specified below can also be included in examples of the peptide having cell migration-stimulating activity:

a peptide having cell migration-stimulating activity which comprises a portion of the amino acid sequence of any one of SEQ ID NOs: 1, 3, and 5, wherein the peptide meets the following condition: when two peptides are selected from the group of <1> to <74> above with the short one being A and the long one being B, the peptide comprises at least A, and consists of the whole B or a portion thereof.

Further, the present invention provides peptides comprising at least any of the amino acid sequences below and having cell migration-stimulating activity, and uses thereof.

Such peptides also include peptides having cell migration-stimulating activity in which an amino acid sequence of one or more (for example, 200 or fewer, 100 or fewer, 50 or fewer, 40 or fewer, 30 or fewer, 20 or fewer, 10 or fewer, 5 or fewer, 3 or fewer, 2 or fewer, without limitation) amino acids have been added to any of the amino acid sequences below. The peptide having cell migration-stimulating activity which comprises at least any one of the amino acid sequences below does not include peptides consisting of the amino acid sequence of any one of SEQ ID NOs: 1, 3, and 5.

[1] the amino acid sequence of position 17 to position 25 in the amino acid sequence of any one of SEQ ID NOs: 1, 3, and 5;
[2] the amino acid sequence of position 45 to position 74 in the amino acid sequence of any one of SEQ ID NOs: 1, 3, and 5;
[3] the amino acid sequence of position 55 to position 84 in the amino acid sequence of any one of SEQ ID NOs: 1, 3, and 5;
[4] the amino acid sequence of position 85 to position 169 in the amino acid sequence of any one of SEQ ID NOs: 1, 3, and 5; and
[5] the amino acid sequence of position 89 to position 185 in the amino acid sequence of any one of SEQ ID NOs: 1, 3, and 5;

The amino acid sequence of position 1 to position 85 and the amino acid sequence of position 86 to position 169 in mouse, rat, and human HMGB1 are known as A-box and B-box, respectively. The amino acid sequences of positions 1 to 169 of mouse, rat, and human are all identical, and maintain 100% identity. Also, the amino acid sequences of position 14 to position 25 in mouse, rat, and human HMGB2 are identical to HMGB1.

The present invention provides peptides having cell migration-stimulating activity mentioned above. The present invention further provides DNAs encoding those peptides, vectors inserted with the DNAs, and transformed cells introduced with the vectors. DNAs encoding peptides of the present invention, vectors inserted with the DNAs, and transformed cells introduced with the vectors are produced using known techniques. The above DNAs may be, for example, artificially synthesized DNAs (for example, degenerate mutants) as long as they encode peptides of the present invention.

The present invention also provides peptides of the present invention produced using cells, and peptides of the present invention synthesized artificially. Peptides of the present invention can be obtained as recombinants by incorporating a DNA encoding the peptide into an appropriate expression system, or can be synthesized artificially. To obtain a peptide of the present invention by genetic engineering methods, a DNA encoding the peptide is incorporated into an appropriate expression system and allowed to express the peptide.

Thus, the present invention provides a method of producing a peptide of the present invention, comprising steps (a) and (b) below:
(a) introducing a DNA encoding a peptide of the present invention into cells, and expressing said peptide; and
(b) collecting said peptide from the cells.

Also, the present invention provides a method of producing a peptide of the present invention which has higher cell migration-stimulating activity than an HMGB1 protein, comprising steps (a) and (b) below:
(a) introducing a DNA encoding a peptide of the present invention into cells, and expressing said peptide; and
(b) collecting said peptide from the cells.

This production method can further comprise the following step: (c) selecting said peptide which has higher cell migration-stimulating activity than the HMGB1 protein.

Hosts that may be applied in the present invention include, but are not limited to, prokaryotic cells and eukaryotic cells. Further, hosts that may be applied in the present invention also include, but are not limited to, bacteria (for example, *E. coli*), yeasts, animal cells (for example, mammalian cells such as HEK293 cell and CHO cell, and insect cells such as silkworm cells), plant cells, and such.

Examples of host/vector systems applicable to the present invention include the expression vector pGEX and *E. coli*. With pGEX, foreign genes can be expressed as a fusion protein with glutathione-S-transferase (GST) (Gene, 67: 31-40, 1988). pGEX incorporated with DNA encoding a peptide of the present invention is introduced into an *E. coli* strain such as BL21 by heat shock, incubated for an appropriate time and then isopropylthio-β-D-galactoside (IPTG) is added to induce the expression of a GST-fused peptide. Since GST of the present invention adsorbs onto Glutathione Sepharose 4B, the expression product is readily separated and purified by affinity column chromatography.

In addition, the following may also be applied as host/vector systems to obtain genetic recombinants of the peptides of the present invention. First, when bacteria are used as hosts, expression vectors for fusion proteins that utilize tags and the like are commercially available. The recombinants of the present invention also include those to which a tag or a partial peptide thereof is attached.

Tags attached to the peptides of the present invention are not particularly limited as long as they do not affect the activity of the peptides of the present invention. Examples include a histidine tag (such as 6×His or 10×His), HA tag, FLAG tag, GST tag, T7-tag, HSV-tag, E-tag, lck tag, and B-tag.

Regarding yeasts, yeasts belonging to the genus Pichia are known to be effective for the expression of sugar chain-containing proteins. In terms of the addition of sugar chains, expression systems that utilize baculovirus vector with insect cells as a host are also useful (Bio/Technology, 6: 47-55, 1988). Further, using mammalian cells, transfection of a vector is carried out using promoters such as CMV, RSV, and SV40. Any of these host/vector systems can be used as an expression system of the peptides of the present invention. Moreover, genes can also be introduced using plasmid vectors and viral vectors such as retrovirus vectors, lentivirus vectors, adenovirus vectors, adeno-associated virus vectors, Sendai virus vectors, Sendai virus envelope vectors, and papilloma virus vectors, without limitation thereto. The vectors may also contain a promoter DNA sequence which effectively induces gene expression, a factor which regulates gene expression, and any molecule necessary for maintaining the stability of DNA.

Thus obtained proteins of the present invention may be isolated from inside or outside (medium and such) of the host cells, and can be purified as proteins that are substantially pure and homogenous. Proteins may be separated and purified using separation and purification methods which are commonly used in protein purification, and are not particularly limited. For example, proteins can be separated and purified by appropriately selecting and combining a chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

Examples of chromatographies include affinity chromatography, ion-exchange chromatography, hydrophobic chromatography, gel filtration, reverse phase chromatography, and adsorption chromatography (Marshak et al., Strategies for Protein Purification and Characterization: A Laboratory Course Manual. Ed Daniel R. Cold Spring Harbor Laboratory Press, 1996). These chromatographies can be performed using liquid phase chromatographies such as HPLC and FPLC.

Moreover, peptides of the present invention are preferably substantially purified peptides. Here, the term "substantially purified" means that the purity of the peptide of the present invention (proportion of the peptide of the present invention in total protein components) is 50% or more, 60% or more, 70% or more, 80% or more, 90% or more, 95% or more, 100% or close to 100%. The upper limit for "close to 100%" depends on the purification techniques and analytical techniques of those skilled in the art, of which examples are 99.999%, 99.99%, 99.9%, 99%, and the like.

Moreover, a substantially purified protein includes any protein purified by any purification method as long as the protein purity is as mentioned above. Examples include, but are not limited to, proteins substantially purified by appropriately selecting and combining the above-mentioned chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

In the present invention, cells secreting a peptide of the present invention can also be produced by the following manner. A vector is produced by inserting a DNA encoding the peptide linked with a secretion signal-encoding DNA (for example, ATG GAG ACA GAC ACA CTC CTG CTA TGG GTA CTG CTG CTC TGG OTT CCA GGT TCC ACT GGT GAC; SEQ ID NO: 10) into a known expression vector or a gene therapy vector. The produced vector is introduced into mammalian cells such as fibroblasts (such as normal skin fibroblasts and cell lines derived therefrom), insect cells, and other cells. Examples of secretion signal-encoding DNAs include, but are not limited to, DNAs having the above-described sequence. Furthermore, there are no particular limitations in the animal species from which these cells derive, although cells of the target animal species subjected to vector administration, cells from the target itself, or cells derived from a blood relative of the target subjected to vector administration, are preferably used.

Meanwhile, peptides consisting of a portion of HMGB1 can be artificially synthesized. For the peptide synthesis methods in the present invention, peptides can be chemically synthesized by either a liquid-phase peptide synthesis method or a solid-phase peptide synthesis method. In the present invention, peptides that are synthesized using a solid-phase peptide synthetic method are preferable. Solid-phase peptide synthesis is one of the generally used methods in chemical peptide synthesis. Polystyrene polymer gel beads with a diameter of about 0.1 mm, modified with amino groups on their surface, or such can be used as the solid phase, and an amino acid chain is extended one by one by dehydration reaction. When the sequence of a peptide of interest is developed, it is excised from the solid-phase surface to obtain the substance of interest. By solid-phase synthesis, it is possible to synthesize ribosome peptides, which are difficult to be synthesized within bacteria, to introduce non-natural amino acids such as D-amino acids or heavy-atom derivatives, to modify peptide and protein backbones, and such. In solid-phase synthesis, long peptide chains of 70 to 100 or more amino acids may be synthesized by using native chemical ligation to bind two peptide chains.

Methods for administering a composition of the present invention include oral administration and parenteral administration. Specifically, parenteral administration includes, but is not limited to, injection, transnasal administration, transpulmonary administration, transdermal administration, and such. As examples of injection, intravenous injection, intramuscular injection, intraperitoneal injection, subcutaneous injection, and such can be used to administer a composition of the present invention systemically or locally (for example, under the skin, in the skin, on the surface of skin, eyeball or palpebral conjunctiva, nasal cavity mucosa, intraoral mucosa and mucosa of the gastrointestinal tract, vaginal mucosa/intrauterine mucosa, damage site or such).

Methods of administering a composition of the present invention include, but are not limited to, for example, intravascular administration (intra-arterial administration, intravenous administration, or such), blood administration, intramuscular administration, subcutaneous administration, intradermal administration, intraperitoneal administration.

There is no limitation on the site of administration, and for example, it may be a tissue site in need of regeneration or its nearby region, a site different from the tissue in need of regeneration, or a site distant to and different from the tissue in need of regeneration. The site is, for example, in the blood (in arteries, in veins, or such), muscle, under the skin, in the skin, in the abdominal cavity, or such, without being limited thereto.

The method of administration may be appropriately selected according to the age and the symptoms of the patient. When a peptide of the present invention is administered, the dose per time of the protein can be selected within a range of 0.0000001 mg to 1000 mg per kg body weight of a patient. Alternatively, the dose can be selected within a range of 0.00001 mg to 100000 mg per body of patient, for example. When administering cells secreting a peptide of the present invention or gene therapy vectors inserted with DNA encoding the peptide, they may be administered such that the amount of the peptide is within the above range. However, the dosage of pharmaceutical compositions of the present invention is not limited thereto.

Pharmaceutical compositions of the present invention can be formulated according to the usual methods (for example, Remington's Pharmaceutical Science, latest edition, Mark Publishing Company, Easton, U.S.A.), and may contain pharmaceutically acceptable carriers and additives together. Examples include surfactants, excipients, colorants, perfumes, preservatives, stabilizers, buffers, suspending agents, isotonizing agents, binders, disintegrants, lubricants, flow promoters, and flavoring agents, although they are not limited thereto and other common carriers may be appropriately used. Specific examples include light anhydrous silicic acid, lactose, crystalline cellulose, mannitol, starch, carmellose calcium, carmellose sodium, hydroxypropylcellulose, hydroxypropylmethylcellulose, polyvinylacetaldiethylamino acetate, polyvinylpyrrolidone, gelatin, medium-chain fatty acid triglyceride, polyoxyethylene hydrogenated castor oil 60, white sugar, carboxymethyl cellulose, corn starch, and inorganic salts.

The present invention provides a kit comprising a substance of any one of (a) to (c) below:
(a) a peptide consisting of a portion of an HMGB1 protein and having cell migration-stimulating activity;
(b) a cell secreting the peptide of (a); and
(c) a vector into which a DNA encoding the peptide of (a) is inserted.

The kit can be used for stimulating cell migration, mobilizing bone marrow cells from bone marrow to peripheral blood, or regenerating tissues. Examples of the kit include those containing: (1) the above-described substance dissolved in fibrinogen and (2) thrombin; or (1) the above-described substance, (2) fibrinogen, and (3) thrombin. In the present invention, it is possible to use commercially-available fibrinogen and thrombin, including, for example, fibrinogen HT-Wf (Benesis-Mitsubishi Pharma), Beriplast (ZLB Behring), Tisseel (Baxter), Bolheal (KAKETSUKEN), and TachoComb (ZLB Behring); however, they are not limited to these examples.

Further, the use of a peptide consisting of a portion of an HMGB1 protein and having cell migration-stimulating activity, a cell secreting the peptide, and a vector into which a DNA encoding the peptide can be expressed as in (1) to (9) below.

(1) A method of stimulating migration of a cell, which comprises administering an effective amount of a substance of any one of (a) to (c) below;
(a) a peptide consisting of a portion of an HMGB1 protein and having cell migration-stimulating activity;
(b) a cell secreting the peptide of (a); and
(c) a vector into which a DNA encoding the peptide of (a) is inserted.

(2) A method of mobilizing a cell from bone marrow to peripheral blood, which comprises administering an effective amount of a substance of any one of (a) to (c) below:
(a) a peptide consisting of a portion of an HMGB1 protein and having cell migration-stimulating activity;
(b) a cell secreting the peptide of (a); and
(c) a vector into which a DNA encoding the peptide of (a) is inserted.

(3) A method of regenerating a tissue, which comprises administering an effective amount of a substance of any one of (a) to (c) below:
(a) a peptide consisting of a portion of an HMGB1 protein and having cell migration-stimulating activity;
(b) a cell secreting the peptide of (a); and
(c) a vector into which a DNA encoding the peptide of (a) is inserted.

(4) Use of a substance of any one of (a) to (c) below in the manufacture of a composition used for stimulating migration of a cell:
(a) a peptide consisting of a portion of an HMGB1 protein and having cell migration-stimulating activity;
(b) a cell secreting the peptide of (a); and
(c) a vector into which a DNA encoding the peptide of (a) is inserted.

(5) Use of a substance of any one of (a) to (c) below in the manufacture of a composition used for mobilizing a cell from bone marrow to peripheral blood:
(a) a peptide consisting of a portion of an HMGB1 protein and having cell migration-stimulating activity;
(b) a cell secreting the peptide of (a); and
(c) a vector into which a DNA encoding the peptide of (a) is inserted.

(6) Use of a substance of any one of (a) to (c) below in the manufacture of a composition used for regenerating a tissue:
(a) a peptide consisting of a portion of an HMGB1 protein and having cell migration-stimulating activity;
(b) a cell secreting the peptide of (a); and
(c) a vector into which a DNA encoding the peptide of (a).

(7) A substance of any one of (a) to (c) below for use in a method of stimulating migration of a cell:

(a) a peptide consisting of a portion of an HMGB1 protein and having cell migration-stimulating activity;
(b) a cell secreting the peptide of (a); and
(c) a vector into which a DNA encoding the peptide of (a) is inserted.

(8) A substance of any one of (a) to (c) below for use in a method of mobilizing a cell from bone marrow to peripheral blood:
(a) a peptide consisting of a portion of an HMGB1 protein and having cell migration-stimulating activity;
(b) a cell secreting the peptide of (a); and
(c) a vector into which a DNA encoding the peptide of (a) is inserted.

(9) A substance of any one of (a) to (c) below for use in a method of regenerating a tissue:
(a) a peptide consisting of a portion of an HMGB1 protein and having cell migration-stimulating activity;
(b) a cell secreting the peptide of (a); and
(c) a vector into which a DNA encoding the peptide of (a) is inserted.

Also, the use of a peptide comprising at least any of the amino acid sequences below and having cell migration-stimulating activity can be rephrased similarly as above.

[1] the amino acid sequence of position 17 to position 25 in the amino acid sequence of any one of SEQ ID NOs: 1, 3, and 5;
[2] the amino acid sequence of position 45 to position 74 in the amino acid sequence of any one of SEQ ID NOs: 1, 3, and 5;
[3] the amino acid sequence of position 55 to position 84 in the amino acid sequence of any one of SEQ ID NOs: 1, 3, and 5;
[4] the amino acid sequence of position 85 to position 169 in the amino acid sequence of any one of SEQ ID NOs: 1, 3, and 5; and
[5] the amino acid sequence of position 89 to position 185 in the amino acid sequence of any one of SEQ ID NOs: 1, 3, and 5.

All prior art documents cited herein are incorporated herein by reference.

Herein below, the present invention will be further illustrated with reference to Examples, but it is not to be construed as being limited thereto.

Example 1—Purification of HMGB-1 and HMGB1-Derived Peptides Using HEK293

RNA was extracted from newborn mouse skin using Trizol (Invitrogen), and then cDNA was synthesized using SuperScript III cDNA synthesis kit (Invitrogen). Using this cDNA as a template, HMGB1 cDNA was amplified by polymerase chain reaction (PCR). The resulting cDNA was inserted into pCAGGS, a plasmid vector for protein expression in mammalian cells, such that the vector would express the protein attached with an IgG κ chain signal sequence as a secretion signal, and with an HA tag, GST tag, and 6×His tag sequences at the N terminus of its amino acid sequence for the convenience of purification (FIG. 1). In addition, a sequence cleaved by HRV3C was inserted between the His tag and the protein or peptide of interest. After digestion with HRV3C, a peptide fragment of Gly Pro Gly Thy Gln (SEQ ID NO: 7) will be attached to the N-terminal of the protein or peptide of interest. In the meantime, restriction sites were added to the cDNA of the full-length HMGB1 or peptide by PCR, and the cDNA was inserted into the KpnI/EcoRI site of the vector.

The pCAGGS expression vector produced above was transfected into a human fetal kidney cell-derived cultured cell line HEK293 using polyethyleneimine (PEI). After 48 hours, the cells and culture supernatant were collected. The cells and culture supernatant were separately collected by centrifugation at 4,400 G at 4° C. for five minutes. Then, the collected supernatant was filtered through a cellulose acetate filter having pores with a diameter of 0.8 μm and then through a nitrocellulose filter having pores with a diameter of 0.45 μm to prepare a sample removed of insoluble fractions. The sample was loaded onto 5-ml HisTrap FF (GE) equilibrated with 50 ml of 50 mM Tris HCl (pH 8.0) containing 50 mM NaCl, and then the absorbed components were washed with 50 mM Tris HCl (pH 8.0) containing 50 mM NaCl and 10 mM imidazole to remove nonspecifically adsorbed components. The specifically adsorbed components were eluted from the column using 50 mM Tris HCl (pH 8.0) containing 50 mM NaCl and 100 mM imidazole. The adsorbed fractions were fractionated into silicone-coated plastic tubes (500 μl/tube). Protein-containing fractions were combined together, and then imidazole was removed using a desalting column PD10 (GE). The fractions were eluted using 50 mM Tris HCl (pH 7.5) containing 150 mM NaCl. HRV3C (Novagen) was added to the eluted samples and the mixture was incubated at 4° C. for eight hours. After cleavage of the tags, the sample was loaded onto a 1-ml HiTrap Heparin column (GE) equilibrated with 50 mM Tris HCl (pH 7.5) containing 150 mM NaCl. The inside of the column was washed with 50 mM Tris HCl (pH 7.5) containing 150 mM NaCl. The protein or peptide bound to the column was eluted with 50 mM Tris HCl (pH 7.5) containing 1,000 mM NaCl.

Migration Assay

Cells of a mouse bone marrow mesenchymal stem cell line (MSC-1 cells, established by Tamai et al. of Osaka University (PDGFRα-positive cells in bone marrow are mobilized by high mobility group box 1 (HMGB1) to regenerate injured epithelia. (Tamai et al., Proc Natl Acad Sci USA. Apr. 4, 2011))) were detached from dishes using trypsin, and collected by centrifugation at 1200 rpm and 4° C. for 10 minutes. The resulting pellet was loosened and suspended at a cell concentration of $2.0 \times 10^6$ to $3.0 \times 10^6$ cells/ml by adding Dulbecco's Modified Eagle Medium (D-MEM) containing 10% fetal bovine serum (FBS). The recombinant protein and peptides produced in HEK293 were diluted with D-MEM containing 10% FBS. The negative control used was phosphate buffered saline (PBS). An acrylic Boyden chamber was used; cells of the mouse bone marrow mesenchymal stem cell line prepared at a cell concentration of $3 \times 10^6$ cells/ml were placed in its upper layer, while a diluted protein or peptide is added to the bottom layer. More specifically, a 28 μl aliquot of a protein or peptide solution was added to each well of the bottom plate of a 48-well chemotaxis chamber (NEURO PROBE 48WELL CHEMOTAXIS CHAMBER), and a polycarbonate membrane with 8 μm pores (Neuro Probe, Inc, Cat: 866-417-0014) was placed on the bottom plate. Then, an upper plate was placed on the membrane and screwed tightly. 50 μl of cells of the mouse bone marrow mesenchymal stem cell line after concentration adjustment were added to the upper plate wells. The chamber was placed in an incubator under 5% $CO_2$ at 37° C. After four hours, the membrane was removed from the chamber and stained with Diff-Quik (Sysmex, Cat: 16920) to detect cells that migrated through membrane pores to the lower compartment.

39

Results

Figure 2A:
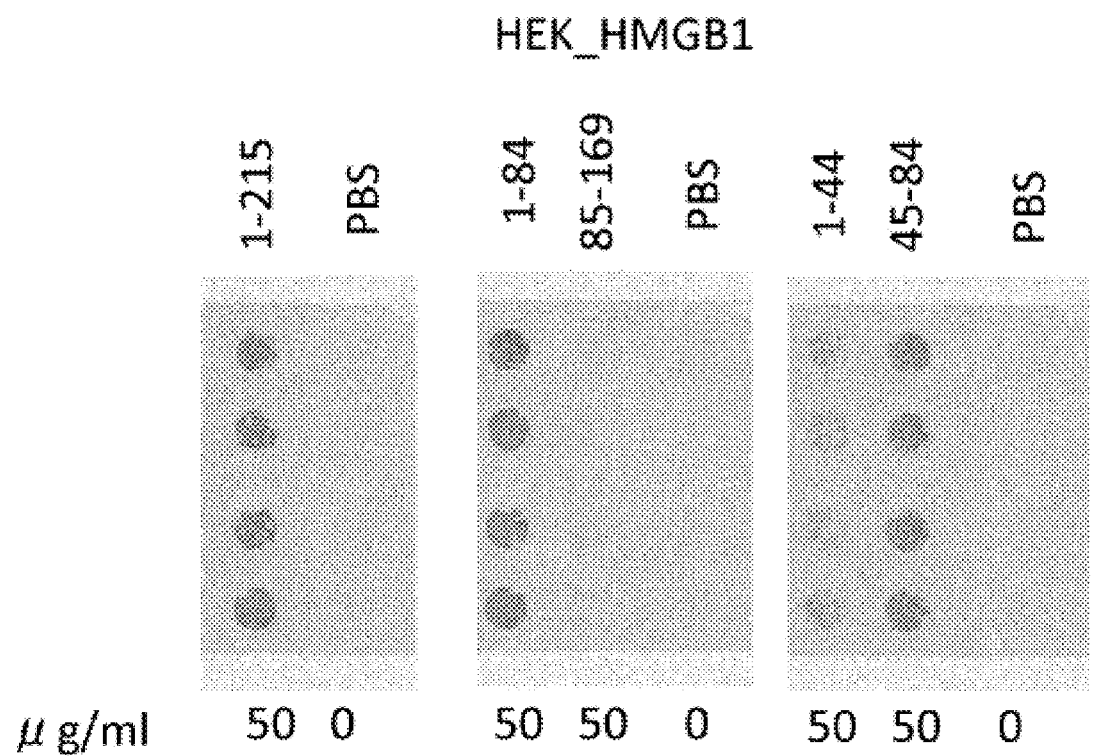
FIG. 2A is a photograph showing the migration activity of an established PDGFRα-positive bone marrow mesenchymal stem cell line towards peptides. Comparisons were made over the positive control full-length HMGB1 (1-215), a peptide consisting of amino acids of positions 1 to 84 (1-84), a peptide consisting of amino acids of positions 85 to 169 (85-169), a peptide consisting of amino acids of positions 1 to 44 (1-44), a peptide consisting of amino acids of positions 45 to 84 (45-84). All of these peptides were produced using HEK293.

The whole mouse HMGB1 (1-215), and a peptide of positions 1 to 84 (1-84), a peptide of positions 85 to 169 (85-169), a peptide of positions 1 to 44 (1-44), a peptide of positions 45 to 84 (45-84), and the negative control (PBS) were assessed for the presence of migration-promoting activity. All the protein and peptides were used at 50 µg/ml. The 85-169 did not show detectable migration-promoting activity, while the remaining 1-215, 1-84, 1-44, and 45-84 showed migration-promoting activity (FIG. 2A).

Figure 3:
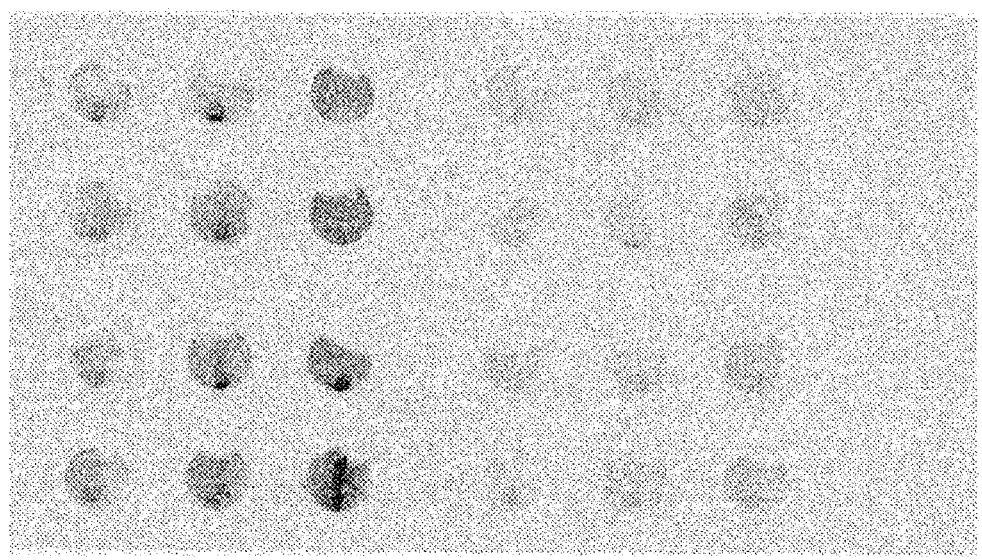
FIG. 3 is a photograph showing migration activity of an established PDGFRα-positive bone marrow mesenchymal stem cell line towards peptides. A comparison was made between a peptide consisting of amino acids of positions 45 to 215 (45-215) of HMGB1 and a peptide consisting of amino acids of positions 63 to 215 (63-215). These peptides were all produced using HEK293.

Furthermore, a peptide of positions 45 to 215 (45-215) and a peptide of positions 63 to 215 (63-215) were used at concentrations of 5, 15, and 25 µg/ml to test the migration-promoting activity (FIG. 3).

Discussion

In mouse, rat, and human HMGB1 (SEQ ID NOs: 3, 5, and 1, respectively), the amino acid sequence spanning positions 1 to 85 is known as A-box, while the amino acid sequence spanning positions 86 to 169 is known as B-box. Among mouse, rat, and human, the amino acid sequence of positions 1 to 185 is completely identical, maintaining 100% identity. The amino acid sequence from positions 186 to 215 is a repeat sequence of glutamic acid and aspartic acid, which is 100% identical between mouse and rat and only differs in two amino acids from the human sequence. The migration-promoting activity of the fragment 85-169 was undetectable, suggesting that it lacks the activity or has the activity below the detection limit under the conditions of the present experiment. On the other hand, 1-84, 1-44, and 45-84 showed excellent migration-promoting activity. Therefore, it is predicted that a domain with migration-promoting activity exist at least in two locations: within the amino acid sequence of positions 1 to 44 and the amino acid sequence of positions 45 to 84. HMGB1 is known to promote the migration of cells such as dendritic cells, and the migration is believed to be induced when HMGB1 stimulates a receptor called RAGE. The RAGE-binding domain is known to be situated in the region corresponding to amino acid positions 150 to 181 in HMGB1. The present discovery that at least two domains different from the RAGE-binding domain promoted the migration of bone marrow mesenchymal stem cells is surprising.

Both 45-215 and 63-215 exhibited migration-promoting activity in a concentration-dependent manner. The activity of 45-215 was stronger as compared to 63-215. It is therefore predicted that there is at least a domain with migration-promoting activity within the amino acids from positions 63 to 84. Furthermore, the following peptides produced using HEK293 also showed the activity of promoting the migration of bone marrow mesenchymal stem line MSC-1:

a peptide comprising the amino acid sequence of positions 1 to 42 (1-42),
a peptide comprising the amino acid sequence of positions 1 to 43 (1-43),
a peptide comprising the amino acid sequence of positions 1 to 45 (1-45),
a peptide comprising the amino acid sequence of positions 1 to 46 (1-46),
a peptide comprising the amino acid sequence of positions 1 to 47 (1-47),
a peptide comprising the amino acid sequence of positions 1 to 48 (1-48),
a peptide comprising the amino acid sequence of positions 1 to 49 (1-49),
a peptide comprising the amino acid sequence of positions 1 to 50 (1-50),
a peptide comprising the amino acid sequence of positions 1 to 51 (1-51),
a peptide comprising the amino acid sequence of positions 1 to 52 (1-52), and
a peptide comprising the amino acid sequence of positions 1 to 62 (1-62).

Example 2—Sorting of Primary Cultured PDGFRα-Positive Bone Marrow Mesenchymal Stem Cells and Assessment of Migration-Promoting Activity Thigh and tibial bones were excised from donor mice: B6.129S4-Pdgfratm11(EGFP)Sor/J (PDGFRα-GFP Mouse). After removing attached muscles and other tissues, the bones were crushed finely and incubated with 0.2% collagenase (Roche, REF: 10103586001)/DMEM/2% FBS (filtrated) at 37° C. for 40 minutes. Then, cell aggregates and muscle tissues were removed by filtration through a 40-µm nylon mesh. After centrifugation at 1200 rpm for 10 minutes, the resulting cells were suspended in αMEM containing 10% FBS and 1% P/S and cultured in an incubator under 5% $CO_2$ at 37° C. until they reached 100% confluence. The cells were harvested and the following experiment was carried out according to the protocol attached to CD11b MicroBeads (Miltenyi Biotec; order No: 130-049-601). The cells were adjusted to $10^7$ cells/90 µl with PBS(-), and CD11b MicroBeads were added at 10 µl/$10^7$ cells. After 15 minutes of reaction at 4° C., the cells were washed twice and suspended in 500 µl of PBS(-). The tube was placed in AutoMACS separator and the cells were collected according to the separation program "Depletes". The collected cells were plated onto an adherent cell culture dish. After adhesion, GFP fluorescence was observed using a fluorescence microscope. The above-described peptide 1-44 produced in HEK293 was tested for the migration-promoting activity using CD11b-negative cells. The peptide was used at a concentration of 40 µg/ml.

Results

Figure 4:
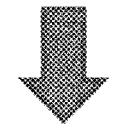
FIG. 4 is a set of photographs showing GFP fluorescence of CD11b-positive and CD11b-negative cells isolated by using MACS after harvesting bone marrow cells from a PDGFRα-GFP mouse, and culturing them for a certain period of time using adherent cell culture dishes.
Figure 4:
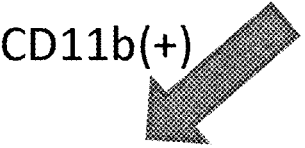
Figure 4:
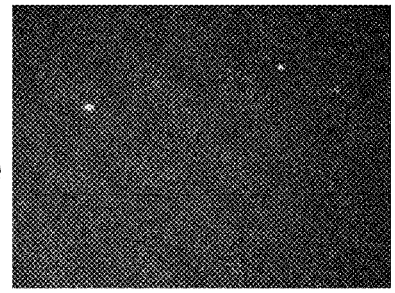
Figure 4:
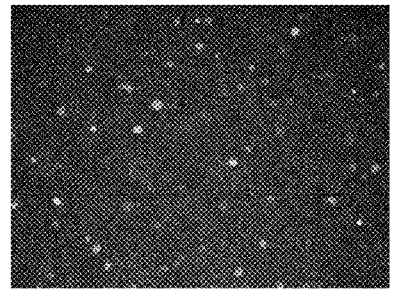
Figure 4:
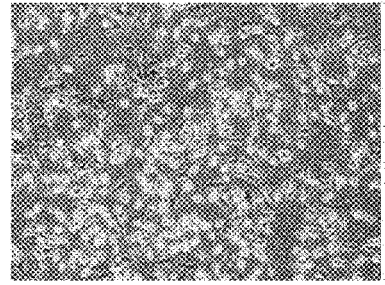
Figure 4:
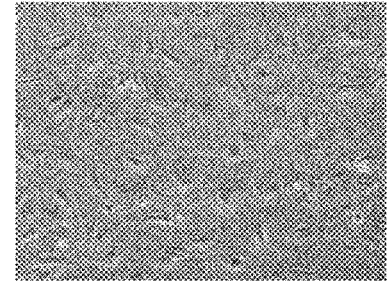
Figure 5:
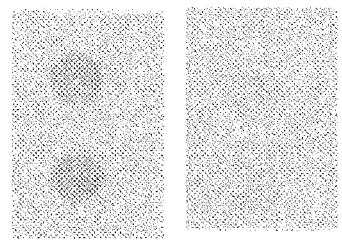
FIG. 5 is a photograph showing migration activity of primary cultured bone marrow mesenchymal cells towards the HMGB1_1-44 peptide.

PDGFRαGFP cells were barely detectable among CD11b-positive cells, while a large number of PDGFRαGFP cells were observed among CD11b-negative cells (FIG. 4). Meanwhile, peptide 1-44 produced using HEK293 exhibited strong migration-promoting activity on CD11b-negative, PDGFRα-positive cells (FIG. 5).

Discussion

CD11b-negative, PDGFRα-positive cells are considered to contain a large number of bone marrow mesenchymal stem cells, which are a type of bone marrow multipotent stem cells. Peptide 1-44 is expected to show migration-promoting activity not only on the established line of bone marrow mesenchymal stem cell but also primary cultured bone marrow mesenchymal stem cells.

Test for the expression of PDGFRα protein in human bone marrow mesenchymal stem cells Methods Human mesenchymal stem cells (hMSC) (Takara Bio; Product No. PT034) were cultured using human mesenchymal stem cell chemically-defined medium kit (MSCGM-CD™ BulletKit™) (Takara Bio; Product No.B0632) according to the product manual. At least cells that had been passaged five times or less were used in experiments.

For Western blotting, about $5 \times 10^7$ cells were harvested and suspended in 1 ml of PBS. The cell suspension was combined with 200 µl of 6×SDS-PAGE sample buffer, and heated at 95° C. for 5 minutes. A bacterial cell lysate of *E. coli* (JM109) expressing rat PDGFRα was dissolved in the sample buffer and used as a positive control. Then, 20 μl of each sample and Precision Plus Dual color Standard (Bio-Rad (cat#: 161-0374) as molecular weight markers were electrophoresed on a 7.5% SDS-PAGE gel. After electrophoresis, the gel was saved and transferred onto a PVDF membrane according to a conventional method. The sample-transferred PVDF membrane was blocked by immersing in 2% skim milk/0.1% Tween20 (PBS-T) at room temperature for one hour. Excess skim milk on the membrane was washed off using PBS-T. PDGFRα Rabbit anti-Human Polyclonal antibody (Lifespan Bioscience (cat#: LS-C9640) as a primary antibody was diluted 3000-fold with PBS-T/2% skim milk, and the blocked membrane was immersed in it for one hour. Then, the membrane was washed a total of three times by immersing in PBS-T for 10 minutes. Anti-Rabbit IgG; HRP-Linked Whole Ab Donkey (GE healthcare (cat#: NA934) as a secondary antibody was diluted 15000-fold with PBS-T/2% skim milk, and the membrane was immersed in it for one hour. Then, the membrane was washed a total of three times by immersing in PBS-T for 10 minutes. PDGFRα bands were detected using ECL Prime (GE healthcare (cat#: RPN2232) according to the product manual.

Results

Figure 2B:
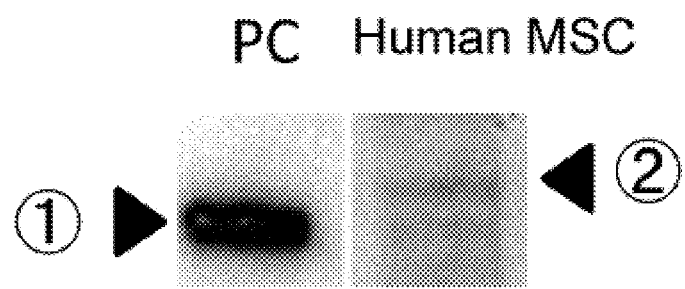
FIG. 2B shows Western blot confirming whether PDGFRα was expressed in bone marrow mesenchymal stem cells or not. PDGFRα expression in human bone marrow mesenchymal stem cells was confirmed.

The positive control, rat PDGFRα produced in *E. coli*, was detected as a band with a size of about 170 kDa. Meanwhile, PDGFRα of human bone marrow mesenchymal stem cells was detected at a position of a little higher molecular weight (FIG. 2B).

Discussion

PDGFRα protein expression was detected by Western blotting not only in mouse but also in human bone marrow mesenchymal stem cells. The reason why the size was a little larger than that of rat PDGFRα produced in *E. coli* may be because of the presence of modification such as glycosylation. PDGFRα was demonstrated to be also expressed in human bone marrow mesenchymal stem cells.

Example 3—Assessment of Primary Cultured PDGFRα-Positive Bone Marrow Mesenchymal Stem Cells for Multipotency FACS sorting of PDGFRα-positive, Lineage-negative, c-kit-negative cells Under sufficiently deep anesthesia with isoflurane, C57B16 mice (male, 6 weeks old) were euthanized by carbon dioxide inhalation. Thigh and tibial bones were excised and fat and muscle tissues were removed from them. The bones were soaked in EtOH to thoroughly remove attached tissues from them. Bone marrow tissues were obtained using a syringe with 26G needle. The obtained bone marrow cells were combined with DMEM containing 0.2% Collagenase A and incubated at 37° C. for 40 minutes. After adding DMEM containing 10% FBS, the cells were centrifuged at 1500 rpm for 10 minutes. The supernatant was discarded and the precipitated bone marrow cells were collected.

The cells were plated in a culture dish with a diameter of 10 cm and cultured using D-MEM containing 10% FBS supplemented with 1× streptomycin-penicillin in an incubator under 5% $CO_2$ at 37° C. The medium was changed with fresh one every three days. The medium of the adherent cells were discarded and the cells were washed twice by adding 10 ml of PBS. After adding 5 ml of 0.25% trypsin, the cells were incubated at 37° C. for 10 minutes. The cells detached from the culture dish were harvested and D-MEM containing 10% FBS was added to stop the reaction of trypsin. The cells were centrifuged at 1200 rpm for 3 minutes. The precipitated cells were collected, suspended at $1 \times 10^6$ cells/100 μl in PBS containing 2% FBS, and dispensed into each well of a round-bottomed 96-well plate. APC-mouse Lineage antibody cocktail (BD Phamingen; Cat. 558074) as a primary antibody was added in 10 μl/well. 1 μl each of PE-mouse CD140a (PDGFRα) (BD Bioscience; Cat. 12-1401-81) and FITC-mouse c-kit (BD Bioscience) were added to each well. The cells were incubated at 4° C. in the dark for 20 minutes. After adding 200 μl of PBS containing 2% FBS to each well, the cells were centrifuged at 1500 rpm for 10 minutes. The supernatant was discarded. Then, the cells were washed twice in the same manner. The cells were sorted using the BD FACSAria cell sorter.

Induction of Osteogenic Differentiation

When cells were grown to 70% confluency, the medium was changed with an osteogenic differentiation medium (R & D; prepared with SC010) every two to three days. The cells were cultured in an incubator at 37° C. under 5% $CO_2$. The culture was continued for about three weeks.

ALP Staining

Cells subjected to induction of osteogenic differentiation were fixed for 10 seconds with the fixative solution of the kit (prepared in advance from the fixative preparation solution), and stained at 37° C. for three minutes with a substrate solution prepared from Fast Blue RR Salt and the substrate stock solution (Muto Pure Chemicals; Cat. No. 1568-2). ALP-positive cells were stained bluish purple.

Induction of Adipogenic Differentiation

When cells were grown to 100% confluency, the medium was changed with an adipogenic differentiation medium (R & D; prepared with SC010) every three to four days. The cells were cultured in an incubator at 37° C. under 5% $CO_2$. The culture was continued for about two weeks.

Oil Red Staining

Cells subjected to induction of adipogenic differentiation were fixed with the propylene glycol fixative solution attached to the kit, and then adipocytes were stained using Oil Red O Solution (DBS; item#KT 025).

Results

Figure 6A:
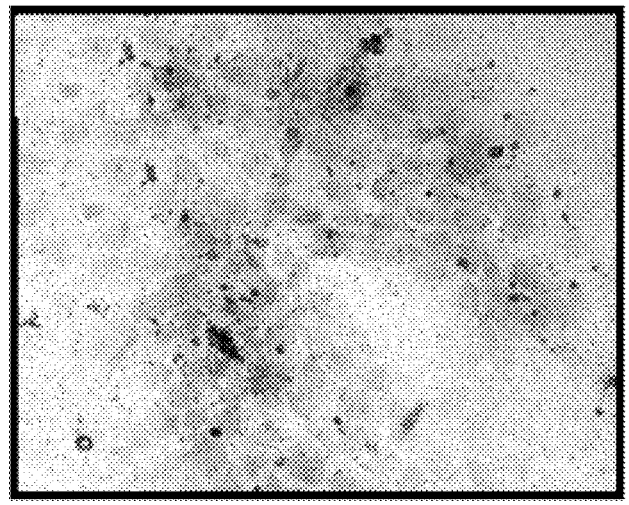
FIGS. 6A-6B are a set of photographs showing the bone differentiation ability (FIG. 6A) and adipocyte differentiation ability (FIG. 6B) of primary culture bone marrow mesenchymal cells (PDGFRα-positive, Lin-negative, and c-kit negative).
Figure 6B:
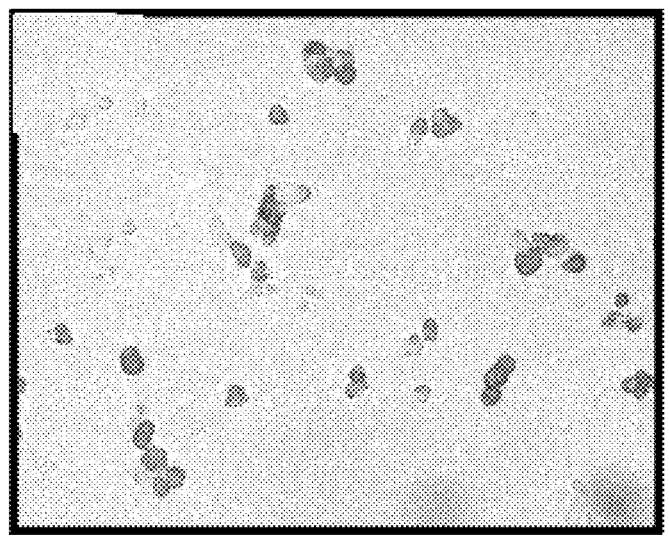

Cells stained bluish purple were observed among the cells subjected to induction of osteogenic differentiation, indicating that the cells differentiated into osteoblast cells (FIG. 6A). Meanwhile, adipocytes containing oil drops stained red were observed among the cells subjected to induction of adipogenic differentiation, indicating the cells differentiated into adipocytes (FIG. 6B).

Discussion

Bone-marrow PDGFRα-positive cells are expected to at least contain bone marrow mesenchymal stem cells capable of osteogenic and adipogenic differentiation.

Example 4—Assessment of Synthetic Peptides for Migration-Promoting Activity

The peptides listed below were custom synthesized using the solid phase method by Medical & Biological Laboratories (MBL). The peptides were synthesized based on the mouse HMGB1 sequence (SEQ ID NO: 3). Synthetic peptides described in subsequent Examples were also prepared based on the mouse HMGB1 sequence.

A synthetic peptide consisting of the amino acid sequence from positions 1 to 10 of HMGB1 (1-10);

a synthetic peptide consisting of the amino acid sequence from positions 1 to 34 of HMGB1 (1-34);

a synthetic peptide consisting of the amino acid sequence from positions 37 to 62 of HMGB1 (37-62);

a synthetic peptide consisting of the amino acid sequence from positions 27 to 62 of HMGB1 (27-62);
a synthetic peptide consisting of the amino acid sequence from positions 56 to 72 of HMGB1 (56-72);
a synthetic peptide consisting of the amino acid sequence from positions 11 to 20 of HMGB1 (11-20);
a synthetic peptide consisting of the amino acid sequence from positions 11 to 25 of HMGB1 (11-25);
a synthetic peptide consisting of the amino acid sequence from positions 11 to 30 of HMGB1 (11-30);
a synthetic peptide consisting of the amino acid sequence from positions 11 to 34 of HMGB1 (11-34);
a synthetic peptide consisting of the amino acid sequence from positions 11 to 44 of HMGB1 (11-44);
a synthetic peptide consisting of the amino acid sequence from positions 17 to 44 of HMGB1 (17-44);
a synthetic peptide consisting of the amino acid sequence from positions 1 to 25 of HMGB1 (1-25); and
the whole mouse HMGB1 produced in HEK293 (1-215 (HEK)) as a positive control were adjusted to 100 µg/ml and placed in the lower layer of a chemotaxis chamber to assess the migration-promoting activity on bone marrow mesenchymal stem cell line (MSC-1).

Results

Figure 7:
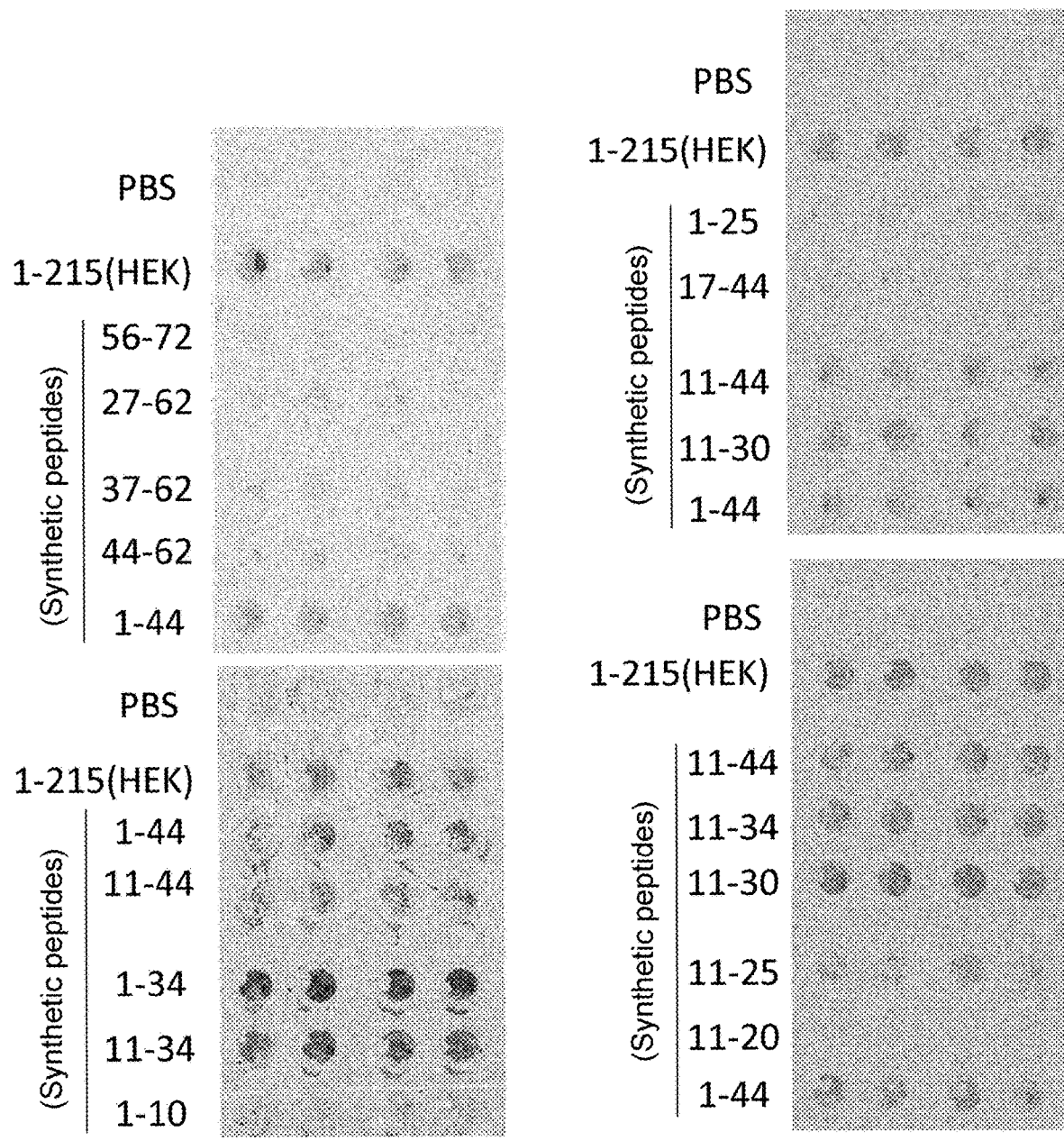
FIG. 7 is a set of photographs showing migration activity of an established PDGFRα-positive bone marrow mesenchymal stem cell line towards various synthetic peptides.

At least synthetic peptides (11-34), (1-34), (11-44), (1-44), and (11-30) were found to have the activity comparable to or higher than that of the positive control (FIG. 7). Furthermore, synthetic peptides (11-25) and (1-25) were also found to have the activity (FIG. 7).

Discussion

It is predicted from the results of Example 1 that the amino acid sequences of positions 1 to 44 and positions 45 to 84 each contain at least one region having the migration-promoting activity. From the results of the present experiment of Example 4, it is predicted that synthetic peptide (11-34) has strong migration-promoting activity and an active center exists at least in the amino acid sequence from positions 11 to 34. Furthermore, synthetic peptide (11-25) was also found to have the activity although it was slightly weaker. It is expected that there is an active center region within the amino acid sequence from positions 11 to 25, and the amino acid sequences located before and after the center enhance the activity.

Example 5

Methods

In order to narrow down the location of the active center, the shorter peptides listed below were synthesized.
A synthetic peptide consisting of the amino acid sequence from positions 11 to 27 of HMGB1 (11-27),
a synthetic peptide consisting of the amino acid sequence from positions 11 to 28 of HMGB1 (11-28),
a synthetic peptide consisting of the amino acid sequence from positions 11 to 29 of HMGB1 (11-29),
a synthetic peptide consisting of the amino acid sequence from positions 12 to 30 of HMGB1 (12-30),
a synthetic peptide consisting of the amino acid sequence from positions 13 to 30 of HMGB1 (13-30),
a synthetic peptide consisting of the amino acid sequence from positions 14 to 30 of HMGB1 (14-30),
a synthetic peptide consisting of the amino acid sequence from positions 15 to 30 of HMGB1 (15-30),
a synthetic peptide consisting of the amino acid sequence from positions 16 to 30 of HMGB1 (16-30),
a synthetic peptide consisting of the amino acid sequence from positions 17 to 30 of HMGB1 (17-30),
a synthetic peptide consisting of the amino acid sequence from positions 18 to 30 of HMGB1 (18-30),
a synthetic peptide consisting of the amino acid sequence from positions 19 to 30 of HMGB1 (19-30),
a synthetic peptide consisting of the amino acid sequence from positions 20 to 30 of HMGB1 (20-30),
a synthetic peptide consisting of the amino acid sequence from positions 21 to 30 of HMGB1 (21-30),
a synthetic peptide consisting of the amino acid sequence from positions 10 to 25 of HMGB1 (10-25),
a synthetic peptide consisting of the amino acid sequence from positions 11 to 25 of HMGB1 (11-25),
a synthetic peptide consisting of the amino acid sequence from positions 12 to 25 of HMGB1 (12-25),
a synthetic peptide consisting of the amino acid sequence from positions 13 to 25 of HMGB1 (13-25),
a synthetic peptide consisting of the amino acid sequence from positions 14 to 25 of HMGB1 (14-25),
a synthetic peptide consisting of the amino acid sequence from positions 15 to 25 of HMGB1 (15-25),
a synthetic peptide consisting of the amino acid sequence from positions 16 to 25 of HMGB1 (16-25),
a synthetic peptide consisting of the amino acid sequence from positions 17 to 25 of HMGB1 (17-25), and
a synthetic peptide consisting of the amino acid sequence from positions 186 to 215 of HMGB1 (186-215).

As positive controls, centrifuged supernatant of the skin of a one-day-old mouse (one individual) incubated in PBS at 4° C. for 12 hours, and the whole mouse HMGB1 (HMGB1 (HEK_1-215)) produced in HEK293 were used. Cells of a bone marrow mesenchymal stem cell line (MSC-1) were placed in the upper layer of a chemotaxis chamber, and the protein and synthetic peptides were added at a concentration of 5 µM or 10 µM to the lower layer of the chemotaxis chamber. The migration assay was carried out by the same method as described in Example 1.

Results

Figure 8A:
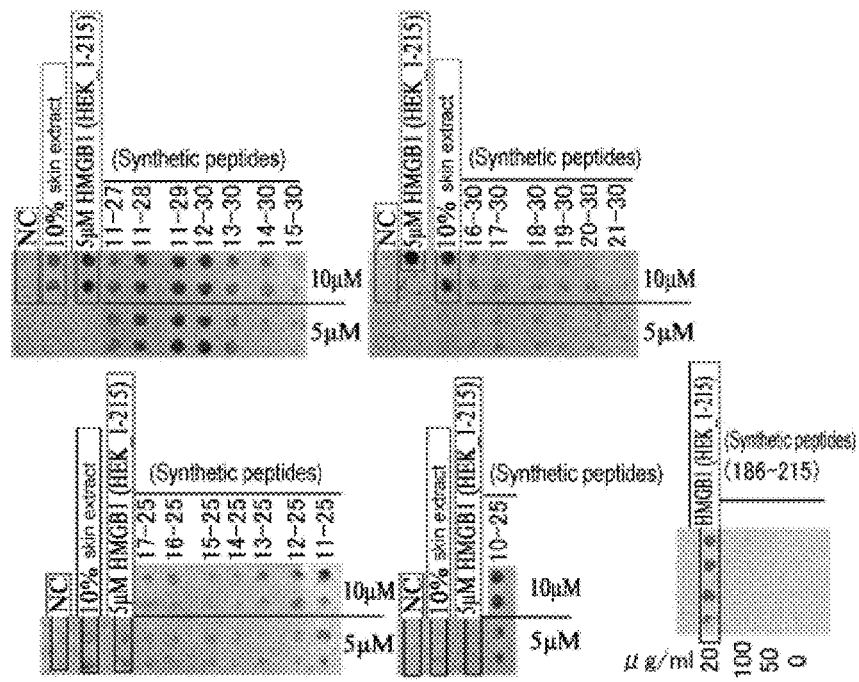
FIG. 8A is a set of photographs showing migration activity of an established PDGFRα-positive bone marrow mesenchymal stem cell line towards various synthetic peptides.
Figure 8B:
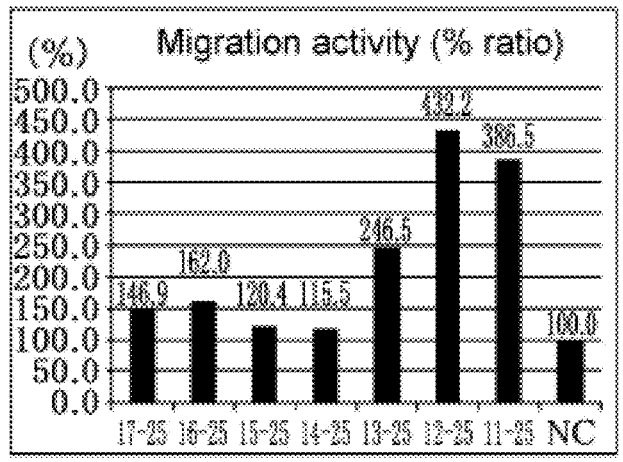
FIG. 8B is a graph showing the quantified migration activity in the left lower photograph in FIG. 8A. The number of cells that migrated towards each of the synthetic peptides and the negative control was measured under the microscope. The values were each graphed with the average value of the negative control set to 100.

At least synthetic peptides (11-27), (11-28), (11-29), (12-30), (13-30), (14-30), and (10-25) exhibited strong migration-promoting activity at 5 µM. Meanwhile, synthetic peptides (11-25), (12-25), (13-25), (14-25), (15-25), (15-30), (16-25), (16-30), (17-25), and (17-30) showed weak activity (FIGS. 8A and 8B).

Discussion

It is predicted from the results of Example 4 that a domain having migration-promoting activity is located within the amino acid sequence from positions 11 to 25. Thus, one of the domains having migration-promoting activity is expected to be present in the amino acids from positions 17 to 25 (9 amino acids).

Comparison of HMGB1 fragments for migration-promoting activity on bone marrow mesenchymal stem cells Methods Each of synthetic peptides 15-30, 16-30, 17-30, 17-44, 45-74, and 55-84, which consists of an HMGB1 fragment, was compared to a negative control (PBS) for the level of the migration-promoting activity on bone marrow mesenchymal stem cells (MSC-1). The Boyden chamber method was used in the same manner as described above. Each peptide was added at 10 to the lower layer of the chamber. $1.5 \times 10^6$ cells dispersed in 1 ml of DMEM containing 10% FBS were placed in the upper layer of the chamber. A polycarbonate membrane having pores with a diameter of 8 µm was inserted between the upper and lower layers. After four hours of incubation in an incubator under 5% $CO_2$ at 37° C., the membrane was removed and treated with Diff-Quik Stain™ to stain only cells that migrated to the lower layer.

Figure 8C:
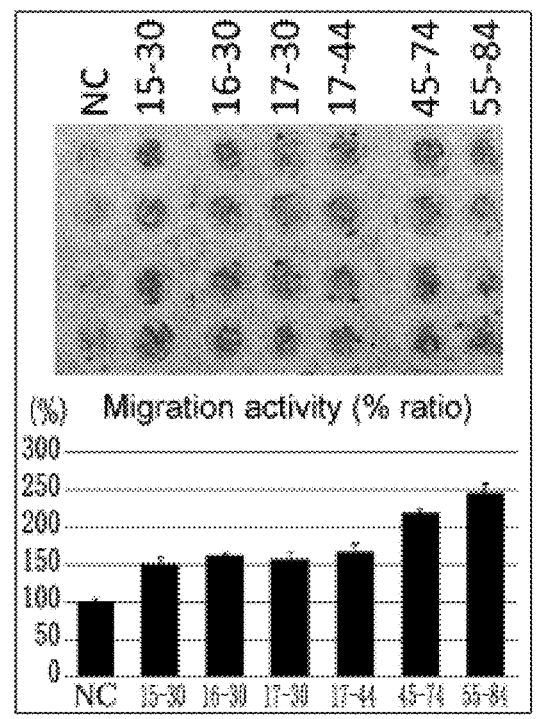
FIG. 8C is a photograph showing migration-promoting activity of each peptide on bone marrow mesenchymal stem cells (MSC-1). The graph shows the ratio of average number of cells measured for each spot in the photograph relative to the negative control.

After staining, the cells were air-dried, and cells that migrated to the lower layer were counted under a microscope. The average number was calculated.
Results All the peptides exhibited stronger migration-promoting activity than that of the negative control.
Discussion Peptide synthesis is a highly excellent production method for pharmaceutical production, because, as compared to production methods using HEK293 or bacteria such as *E. coli*, it can ensure a consistent production amount at low costs and prevent contamination with biologically-derived toxins and such. On the other hand, unlike the production in organisms, post-translational modification and folding do not occur properly, and therefore low molecular weight peptides containing highly hydrophobic amino acids often become very insoluble in aqueous solutions. In the present Example, since the migration-promoting activity of peptides was relatively weak, the activity strength as compared to the negative control was measured correctly using a microscope. A strong migration-promoting activity as compared to the negative control was detected for all the peptides (FIG. 8C).

Example 6—Assessment of Synthetic Peptides for Migration-Promoting Activity

Figure 9:
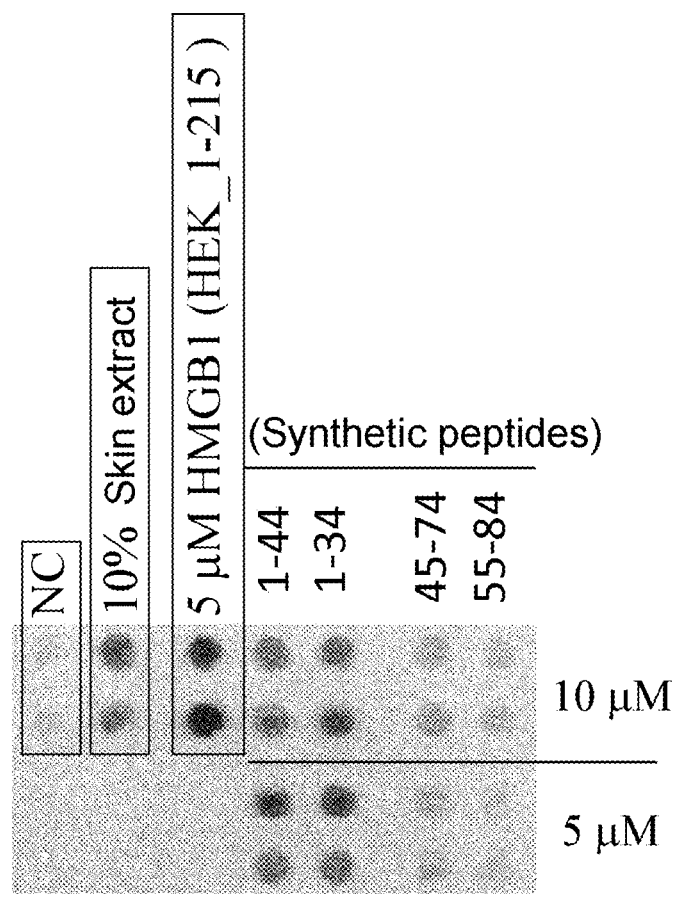
FIG. 9 is a photograph showing migration activity of an established PDGFRα-positive bone marrow mesenchymal stem cell line towards various synthetic peptides.

Synthetic peptides (1-44) and (1-34) used in Example 4, peptide (45-74) consisting of the amino acids of positions 45 to 74, and peptide (55-84) consisting of the amino acids of positions 55 to 84 were tested by migration assay using a chemotaxis chamber in the same manner as described in Example 5. The assay was carried out simultaneously at two concentrations of 10 µM and 5 µM.
Results Both synthetic peptides (45-74) and (55-84) exhibited migration-promoting activity which was however weaker as compared to synthetic peptides (1-44) and (1-34) (FIG. 9).
Discussion The results of Example 1 showed that peptides (1-84), (1-44), and (45-84) produced in HEK293 had strong migration-promoting activity on PDGFRα-positive mesenchymal stem cells. The results of Example 4 showed that synthetic peptides (1-44) and (1-34) retained the strong activity. Meanwhile, the results of Example 6 here revealed that synthetic peptides (45-74) and (55-84) also exhibited migration-promoting activity although it was slightly weaker.

It is known that peptides and proteins are subjected to modification such as glycosylation when synthesized in eukaryotic cells such as HEK293. On the other hand, synthetic peptides do not undergo modification. The fact that the migration-promoting activity of peptide (45-84) produced in HEK293 was greater as compared to synthetic peptides "(45-74) and (55-84)" consisting of the amino acid sequence of positions 45 to 84 suggests that the peptide was subjected to certain modification.

Meanwhile, a past experiment using mesoangioblasts (Palumbo et al., J. Cell Biol., 164: 441-449, 2004) has shown that the sequence consisting of the amino acids of positions 1 to 187 resulting from cleavage at the C terminal end retains the cell migration-promoting activity of HMGB1 (215 amino acids in entire length) while the sequence consisting of the amino acids of positions 1 to 89, the sequence consisting of the amino acids of positions 90 to 176, and the sequence consisting of the amino acids of positions 1 to 176 have almost no activity. On the other hand, the portion predicted to be a ligand for RAGE, which is one of known HMGB1 receptors, corresponds to the sequence consisting of the amino acids of positions 150 to 181. The document described above also shows that the migration-promoting activity is suppressed by a dominant negative of RAGE. Moreover, another report (Yang et al., J Leukoc Biol. January; 81(1): 59-66, 2007) shows that the RAGE receptor is also utilized when HMGB1 promotes migration of dendritic cells. Thus, for the migration-promoting activity of HMGB1, attention has previously been drawn to the C-terminal peptide of HMGB1, which is a ligand portion for RAGE.

The present Examples succeeded in identifying two regions having cell migration-promoting activity within the N-terminal peptide, which had been believed not to have the cell migration-promoting activity. Excessive inflammation is known to be an inhibitory factor in tissue regeneration. Since the active regions discovered in the present Examples are completely different from the ligand for RAGE, it is expected that they will enable recruitment of PDGERα-positive stem cells while avoiding recruitment of inflammatory cells such as dendritic cells, and therefore development of pharmaceuticals with much less side effects will be possible.

Example 7—Quantitative Comparison of Peptide (1-44) and the Whole HMGB1 for Migration-Promoting Activity HEK293 cells were transfected with the expression vector for mouse HMGB1 (1-44) using polyethyleneimine, and HMGB1 secreted into cell supernatant was collected and purified (HEK293 transient) in the same manner as described in Example 1. Also, after transfection by the same procedure, 2 µg/ml puromycin was added to the culture medium, and cells constantly secreting HMGB1 (1-44) were selected by the drug. HMGB1 secreted to this cell supernatant was purified (HMGB1-stable).
Production of HMGB1-derived peptides using *E. coli*

In order to produce the peptide of amino acids 1-44 using *E. coli*, a cDNA for expression of a chimeric peptide to be added to the N terminal side of cDNA encoding the amino acids of positions 1 to 44 of mouse HMGB1 to be cleaved off by HRV3C was inserted into pENTR vector (Invitrogen). LR reaction was carried out for transfer into pDEST17 vector. The expression vector has a T7 promoter and is capable of protein expression in *E. coli*. Furthermore, it adds 6×His tag to the N terminal end. As a result of HRV3C cleavage, the 6×His tag is removed and a peptide fragment of Gly Pro Gly Thy Gln (SEQ ID NO: 7) is added to the N terminal end of the peptide.

*E. coli* BL21 (DE3) was transformed with the above-described expression vector by electroporation. After adding SOC medium, the *E. coli* was cultured in a shaker at 37° C. for 60 minutes. The cells were plated on an LB agar plate containing carbenicillin, and incubated at 37° C. for 18 hours. Single colonies were collected and combined with LB containing carbenicillin, and cultured in a shaker at 37° C. When the O.D. 600 reached 0.4-0.5, IPTG was added at a final concentration of 0.1 mM, and shaken at 30° C. After 6 hours, the *E. coli* was harvested, and centrifuged at 3500 rpm for 30 minutes. The precipitated *E. coli* was collected, and 50 mM Tris-HCl (pH 8.0) containing 50 mM NaCl and 6M urea was added thereto. The *E. coli* was lysed by pipetting and loaded onto 5 ml HisTrap FF(GE) equilibrated with 50 mM Tris-HCl (pH 8.0) containing 50 mM NaCl and 6 M urea. Then, the adsorbed material was washed with 50 mM Tris HCl (pH 8.0) containing 50 mM NaCl, 6 M urea, and 10 mM imidazole to remove non-specifically adsorbed components. The specifically adsorbed material was eluted from the column with 50 mM Tris HCl (pH 8.0) containing 50 mM NaCl, 6 M urea, and 300 mM imidazole. The adsorbed material was fractionated into 500 µl fractions in silicone-coated plastic tubes, and protein-containing fractions were combined together. Then, imidazole was removed using desalting column PD10 (GE) and elution was carried out using 50 mM Tris-HCl (pH 7.5) containing 150 mM NaCl. HRV3C (Novagen) was added to the eluted sample and allowed to react at 4° C. for 8 hours. After tag cleavage, the sample was loaded onto a 1-ml HisTrap FF column equilibrated with 50 mM Tris HCl (pH 7.5) containing 150 mM NaCl and the peptide was collected as an unbound fraction.

The synthetic peptide (1-44) was prepared in the same manner as described above. The peptides and protein were used at a concentration of 2 µM for migration assay using a bone marrow mesenchymal stem cell line (MSC-1). The pore area of the chemotaxis chamber and the area of migrated cells were measured using image analysis software.

Results

Figure 10:
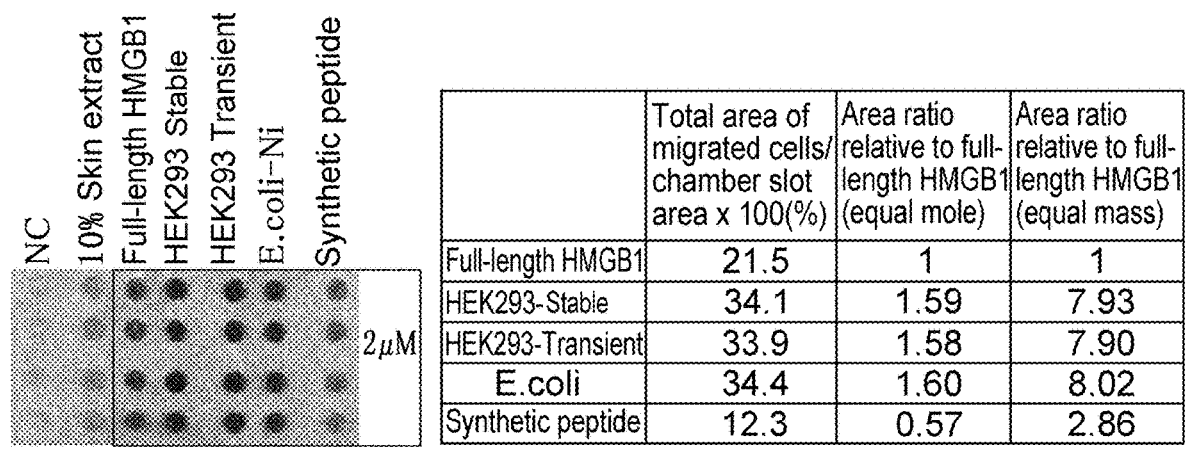
FIG. 10 is a photograph and diagram showing migration activity of an established PDGFRα-positive bone marrow mesenchymal stem cell line towards various peptides. The HMGB1_1-44 peptide (1-44) produced by HEK293 cells with constant peptide secretion, HEK293 cells with peptide secretion through transient plasmid transfection, E. coli, and peptide synthesis, were compared with the positive control full-length HMGB1.

When compared per equal mole, peptide (1-44) produced in HEK293 and peptide (1-44) produced in E. coli both exhibited migration-promoting activity about 1.6 times greater than the full-length HMGB1. When compared per equal mass, peptide (1-44) produced in HEK293 and peptide (1-44) produced in E. coli both exhibited migration-promoting activity about 8 times greater than the full-length HMGB1. Meanwhile, the migration-promoting activity of synthetic peptide (1-44) was 0.57 times greater and 2.86 times greater than the full-length HMGB1 when compared per equal mole and per equal mass, respectively (FIG. 10).

Discussion

The results of Examples 1 and 6 and others suggest that there are at least one or more active center sites for the migration-promoting activity in each of the amino acid sequence of 1 to 44 and the amino acid sequence of positions 45 to 84, and thus there are a total of two or more active center sites. Furthermore, the results of the present Example 7 demonstrated that peptide (1-44) produced in HEK293 had migration-promoting activity nearly 8 times that of the full-length HMGB1 when compared per equal mass (about 1.6 times when compared per equal number of moles). In addition, peptide (45-84) produced in HEK293 also has comparable migration-promoting activity (FIG. 2A). The findings described above demonstrate that HMGB1 has at least two regions that have greater migration-promoting activity than the same number of moles of the full-length HMGB1, which are located within the amino acid sequence of positions 1 to 44 and the amino acid sequence of positions 45 to 84, and the activity of the full-length HMGB1 is significantly lower than the sum of the activity of the two regions. Since the peptide of positions 1 to 44 and the peptide of positions 45 to 84 were adjacent to each other according to the result of crystallographic analysis of the full length HMGB1, it is predicted that these regions inhibit the activity of each other. It is suggested that the separation into peptides resulted in elimination of the inhibition and an increase in the activity of each.

Example 8—FACS Analysis of Bone Marrow Mesenchymal Stem Cell Line (MSC-1) for Expression of PDGFRα, Lineage Marker, and CD44

Cells of mouse-derived bone marrow mesenchymal stem cell line MSC-1 were plated in a culture dish with a diameter of 10 cm and cultured in an incubator under 5% $CO_2$ at 37° C. using D-MEM containing 10% FBS supplemented with 1× streptomycin-penicillin. After the cells were grown to 80-90% confluency, the medium was discarded and the cells were washed twice by adding 10 ml of PBS, Then, 5 ml of 0.25% trypsin was added and incubated at 37° C. for 10 minutes. The cells detached from the culture dish were harvested and DMEM containing 10% FBS was added to stop the reaction of trypsin. The cells were centrifuged at 1200 rpm for 3 minutes. The precipitated cells were collected, and suspended at $1\times10^6$ cells/100 µl of PBS containing 2% FBS. The cells were dispensed into each well of a round-bottomed 96-well plate. APC-mouse Lineage antibody cocktail (BD Phamingen; Cat. 558074) as a primary antibody was added in 10 µl/well. 1 µl each of PE-mouse CD140a (PDGFRα) (BD Bioscience; Cat. 12-1401-81) and FITC-mouse CD44 (BD Bioscience; Cat. 553-133) were added to each well. The cells were incubated at 4° C. in the dark for 20 minutes. A 200-µl aliquot of PBS containing 2% FBS was added to each well. The cells were centrifuged at 1500 rpm for 10 minutes. The resulting supernatant was discarded. Then, the cells were washed twice in the same manner. The cells were suspended in 100 µl of PBS and analyzed with BD FACSCantTMII.

Results

Figure 11:
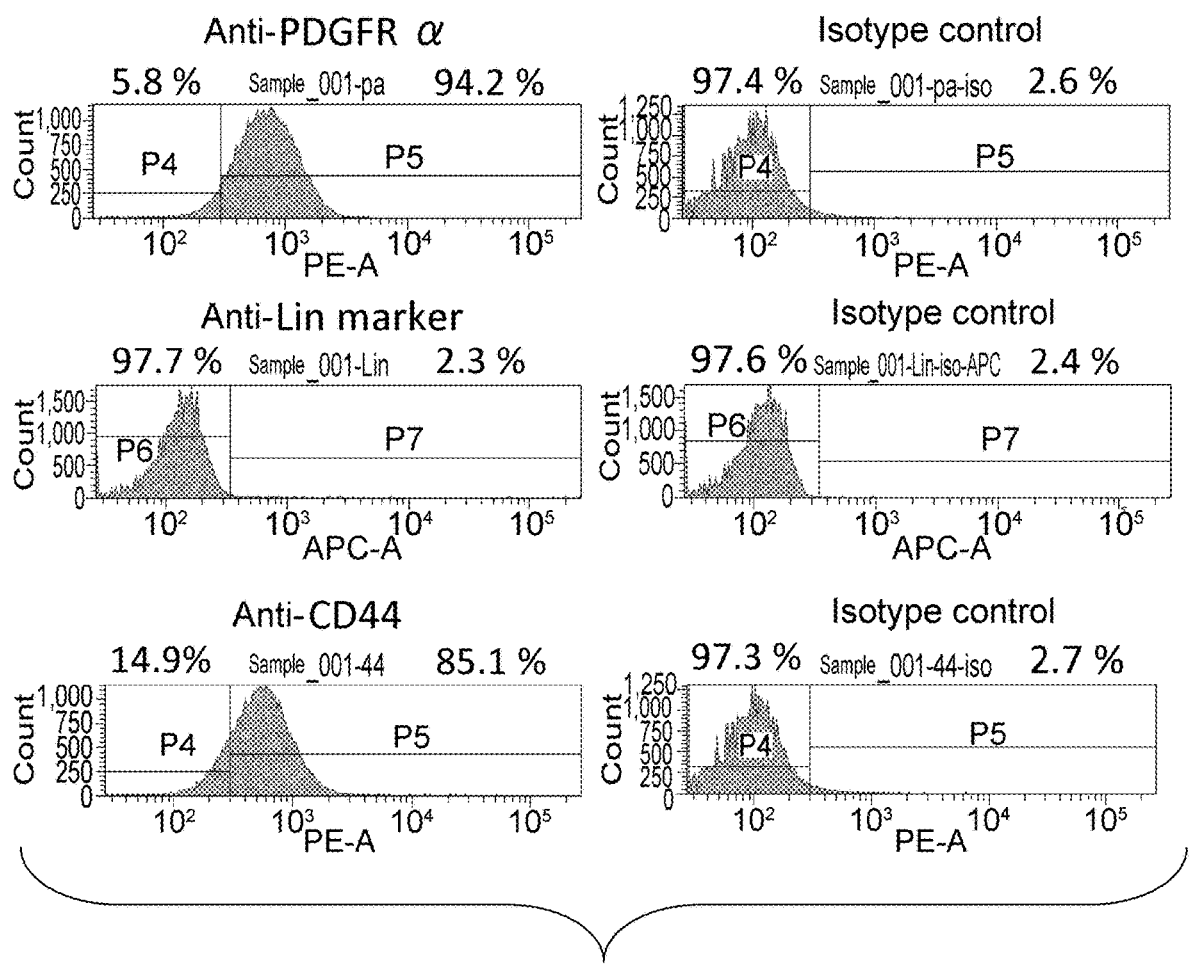
FIG. 11 shows FACS analysis of PDGFRα, lineage marker, and CD44 in an established PDGFRα-positive bone marrow mesenchymal stem cells.

Bone marrow mesenchymal stem cells (MSC-1) were PDGFRα-positive, Lineage-negative, and CD44-positive (FIG. 11).

Discussion

The cells used for the migration-promoting activity retain the properties of PDGFRα-positive bone marrow mesenchymal stem cells.

Example 9—Migration-Promoting Activity of Synthetic Peptide (1-34) on Mouse Keratinocytes Newborn C57/B16 mice were euthanized using isoflurane and carbon dioxide inhalation. Then, the mice were washed thoroughly with EtOH and PBS. The skin together with dermis was exfoliated and the blood was washed off with PBS. The exfoliated skin was placed in Dispase I (Sanko Junyaku Co., Cat: GD81060) at 4° C. for 16 hours. The epidermis and dermis were detached with forceps, and the epidermis was placed in trypsin (Nacalai tesque, Cat: 3554-64) at 37° C. for 10 minutes. When white turbidity began to appear, the reaction was stopped with S-MEM (GIBCO, Cat: 11380)/15% FBS(Ca-)P/S. The resulting cells were centrifuged at 160×G for 5 minutes, and suspended in CnT-07 medium (CELLnTEC, Cat: CnT-07 BM) and plated in a 10-cm dish. The cells were cultured under 5% $CO_2$ at 37° C. and the medium was changed every three days. The cells were passaged when they reached 80% to 90% confluency. The cells were harvested from the dish using trypsin. After inactivation of trypsin with DMEM containing 10% FBS, a synthetic peptide consisting of the amino acid sequence of positions 1 to 34 (1-34) was examined for migration-promoting activity according to the migration assay method described above.

PDGFRα Expression in Mouse Keratinocytes

Figure 12A:
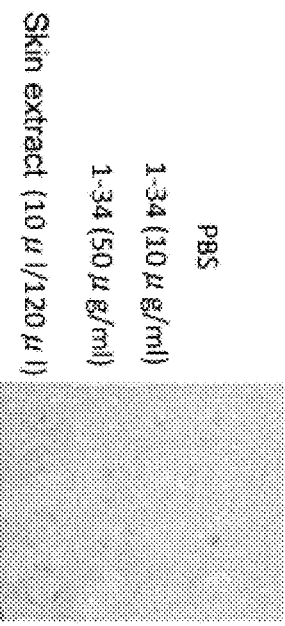
FIG. 12A is a photograph showing migration activity of mouse keratinocytes towards the HMGB1_1-34 peptide.
Figure 12B:
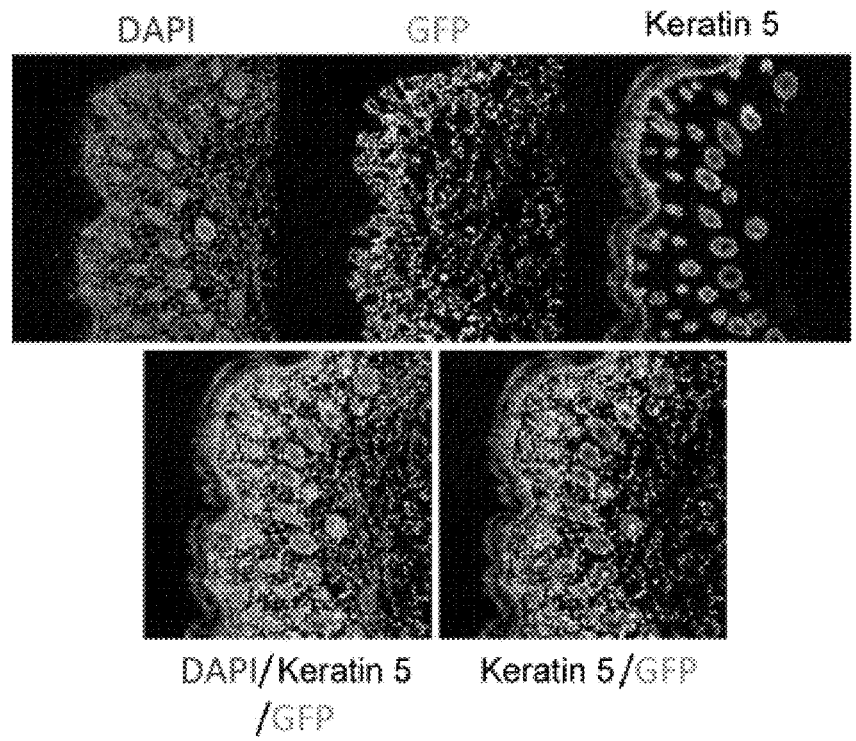
FIG. 12B is a set of photographs of immunohistochemistry of keratin 5 in PDGFRα-GFP mouse skin. Keratinocytes which are keratin 5-positive cells did not express PDGFRα.

Newborn B6.129S4-Pdgfratm11(EGFP)Sor/J mice were fixed by perfusion with 4% PFA. A 1.0×1.0 $cm^2$ area of the newborn skin was excised, and further fixed by immersion with 4% PFA for 12 hours and then with 30% sucrose for 12 hours at 4° C. After washing with PBS(-), the skin was cryoembedded in OTC compound and sliced into 8-µm cryosections in a cryostat. The sections were washed twice with PBS to wash out the compound, and blocked with 10% goat serum in PBS at room temperature for 1 hour. The primary antibody used was rabbit anti-keratin 5 (Covance, Cat: PRB-160P) or rabbit anti-vimentin (Abcam, Cat: ab7783-500) diluted 500 times with PBS containing 10% goat serum. After five hours of incubation with the primary antibody at 4° C., the sections were washed twice with PBS. The secondary antibody used was Alexa Fluor 546 goat anti-rabbit IgG(H+L) (Invitrogen, Cat: A11035) diluted 500 times with PBS containing 10% goat serum. After 45 minutes of incubation with the secondary antibody at room temperature, the sections were washed twice with PBS, and incubated with 2 µg/ml DAPI (4',6-diamino-2-phenylindole) at room temperature for 3 minutes. Then, after washing twice with PBS, the sections were mounted with a mounting medium containing a fluorescence antifade.
Results
Synthetic peptide (1-34) did not show migration-promoting activity on mouse keratinocytes (FIG. 12A). Furthermore, GFP fluorescence was not observed on cells positive for keratin 5, which is a mouse keratinocyte marker (FIG. 12B).
Discussion
Keratinocytes did not express PDGFRα. Furthermore, synthetic peptide (1-34) did not have migration-promoting activity on keratinocytes.

Figure 13A:
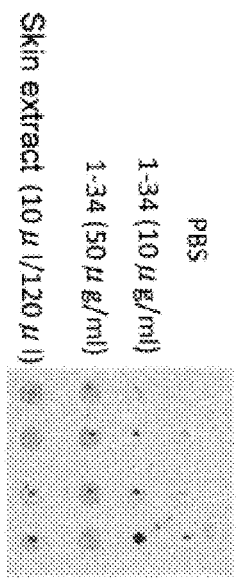
FIG. 13A is a photograph showing migration activity of mouse dermal fibroblasts towards the HMGB1_1-34 peptide (1-34).
Figure 13B:
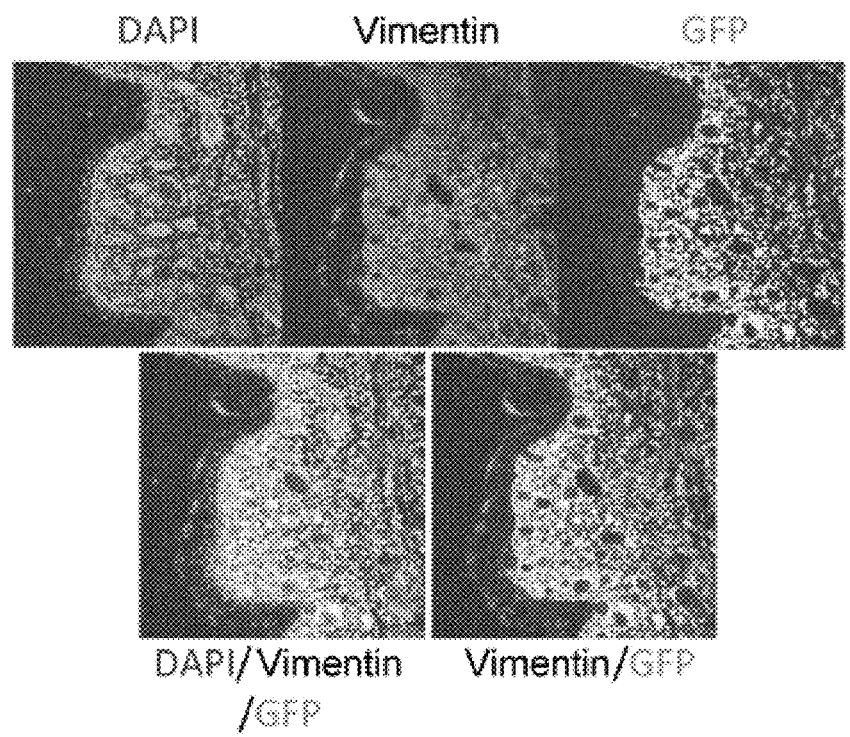
FIG. 13B is a set of immunohistochemistry photographs of vimentin in PDGFRα-GFP mouse skin. Some of the dermal fibroblasts, which are vimentin-positive, expressed PDGFRα.

Example 10—Migration-Promoting Activity of Synthetic Peptide (1-34) on Mouse Skin Fibroblasts Newborn C57/B16 mice were euthanized using isoflurane and carbon dioxide inhalation. Then, the mice were washed thoroughly with EtOH and PBS. The skin together with dermis was exfoliated and the blood was washed off with PBS. The exfoliated skin was cut into fine pieces with scissors. The skin pieces were placed in DMEM (Nacalai tesque, Cat: 08458-45) containing 0.2% collagenase (Roche, REF: 10103586001) and shaken at 37° C. for 30 minutes. The reaction was stopped with DMEM/30% FBS/P/S. The resulting cells were centrifuged at 160×G for 5 minutes and plated in a 10-cm dish. The cells were cultured under 5% $CO_2$ at 37° C. and the medium was changed every three days. The cells were passaged when they reached 80% to 90% confluency. The cells were harvested from the dish using trypsin. After inactivation of trypsin with D-MEM containing 10% FBS, a synthetic peptide consisting of the amino acid sequence of positions 1 to 34 (1-34) was assessed for migration-promoting activity according to the migration assay method described above.
Newborn B6.129S4-Pdgfratm11(EGFP)Sor/J mice were fixed by perfusion using 4% PFA. A 1.0×1.0 cm² area of the newborn skin was excised, and further fixed by immersion with 4% PFA for 12 hours and then with 30% sucrose at 4° C. After washing with PBS(-), the skin was cryoembedded in OTC compound and sliced into 8-µm cryosections in a cryostat. The sections were washed twice with PBS to wash out the compound, and blocked with 10% goat serum in PBS at room temperature for 1 hour. The primary antibody used was rabbit anti-vimentin (Abcam; Cat. ab7783-500) diluted 500 times with PBS containing 10% goat serum. After five hours of incubation with the primary antibody at 4° C., the sections were washed twice with PBS. The secondary antibody used was Alexa Fluor 546 goat anti-rabbit IgG(H+L) (Invitrogen; Cat. A11035) diluted 500 times with PBS containing 10% goat serum. After 45 minutes of incubation with the secondary antibody at room temperature, the sections were washed twice with PBS, and incubated with 2 µg/ml DAPI (4',6-diamino-2-phenylindole) at room temperature for 3 minutes. Then, after washing twice with PBS, the sections were mounted with a mounting medium containing a fluorescence antifade.
Results
Synthetic peptide (1-34) exhibited migration-promoting activity on skin fibroblasts (FIG. 13A). Furthermore, GFP fluorescence-positive cells were observed among cells positive for vimentin, which is a fibroblast marker (FIG. 13B).
Discussion
Skin fibroblasts expressed PDGFRα. Synthetic peptide (1-34) had migration-promoting activity on skin fibroblasts. Both bone marrow mesenchymal stem cells and newborn skin fibroblasts are positive for PDGFRα. Peptide (1-34) showed migration-promoting activity on both cells but not on keratinocytes, which are PDGFRα-negative cells. PDGFRα is expected to be useful as a marker for cells on which amino acid sequences comprising peptide (1-34) exhibit migration-promoting activity.

Example 11—Assessment of PDGFRα Expression in Mouse Skin Fibroblasts Using FACS

Figure 14:
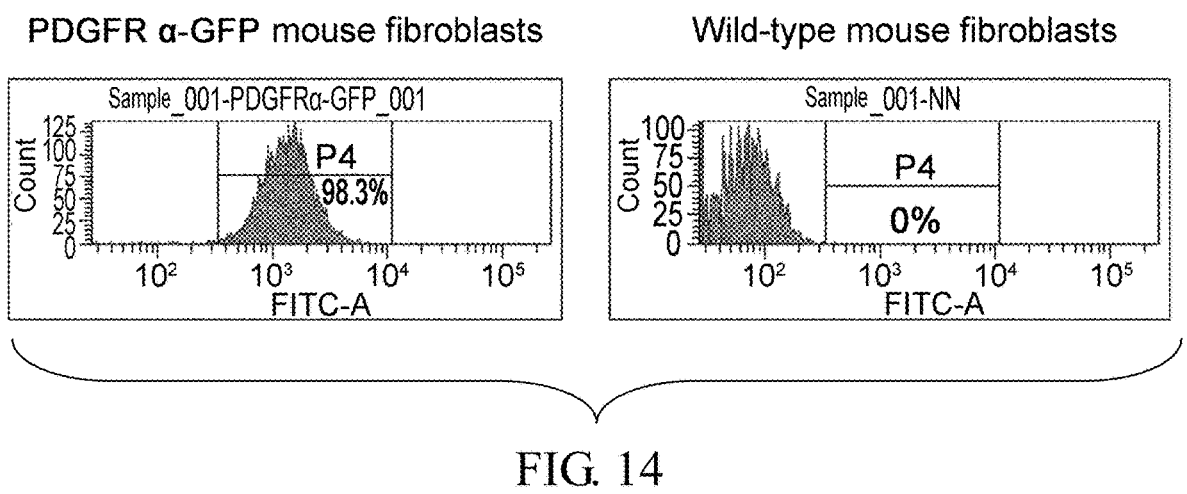
FIG. 14 shows FACS analysis of the PDGFRα-GFP mouse dermal fibroblasts and the wild-type mouse (C57/B16 mouse) dermal fibroblasts. Nearly 98% and more of the mouse dermal fibroblasts expressed PDGFRα.

Newborn B6.129S4-Pdgfratm11(EGFP)Sor/J mice were washed thoroughly with EtOH and PBS. The skin was detached from muscles and cut into small pieces with a width of 3 mm. The skin pieces were transferred into DMEM/5% FBS containing 500 unit/ml dispase and incubated at 4° C. for 18 hours. The dermis was exfoliated from the epidermis and cut into fine pieces with scissors. The fine pieces of dermis were placed in DMEM containing 0.2% collagenase and shaken at 37° C. for 30 minutes. After adding DMEM containing 30% FBS, the resulting cells were centrifuged at 160×G for 5 minutes. The precipitated cells were plated in a 10-cm dish, and cultured under 5% $CO_2$ at 37° C. The medium was changed every three days and the cells were passaged when they reached 80% to 90% confluency. The cells were harvested from the dish using trypsin, and after adding D-MEM containing 10% FBS the cells were collected by centrifugation. GFP fluorescence of cells was detected and analyzed with BD FACSCantTMII. Results 98% or more of fibroblasts in newborn mouse skin were positive for PDGFRα (FIG. 14).
Discussion
PDGFRα-positive cells were quantified using FACS. Almost all fibroblasts were shown to be PDGFRα-positive cells, as in the result of immunohistochemistry.

Example 12

Methods
10 µg of synthetic peptide (amino acids of positions 1 to 44) was dissolved in 200 µl of PBS and administered to C57B16 mice (female, 8 weeks old) via the caudal vein using a syringe with 30-gauge needle. An equal volume of PBS was administered as a negative control. After 12 hours, peripheral blood was collected from the left ventricle of the heart under systemic anesthesia with isoflurane. After adding 3 ml of PBS (Nacalai tesque; Cat. 14249-95), 3 ml of Ficoll-Paque Plus (GE Healthcare; Cat. 17-1440-02) was overlaid onto the blood. The blood was centrifuged in a centrifuge at 400 G and 25° C. for 45 minutes. The upper serum layer was discarded, and only the cells seen as a white band in the intermediate layer were collected. Then, 45 ml of PBS was added to the collected cells, and centrifuged in a centrifuge at 800 G and 25° C. for 20 minutes. After the supernatant was discarded, 10 ml of PBS was added and centrifuged at 1500 rpm and 25° C. for 10 minutes. The supernatant was discarded and 1 ml of hemolysis buffer (HLB; Immuno-Biological Laboratories) was added to the cells. After pipetting, the cells were allowed to stand for 5 minutes. Then, 10 ml of PBS was added to the cells and centrifuged at 1500 rpm and 25° C. for 10 minutes. The precipitated mononuclear cells were collected and adjusted to 1×10$^6$ cells/100 μl (PBS containing 2% FBS) in a round-bottomed 96-well plate. 1 μl each of PE-mouse CD140a (PDGFRα) (BD Bioscience; Cat. 12-1401-81) or FITC-mouse CD44 (BD Bioscience, Cat.553-133) was added to each well containing mononuclear cells. The cells were incubated at 4° C. in the dark for 20 minutes. 200 μl of PBS was added to each well, and centrifuged at 1500 rpm and 4° C. for 10 minutes. The supernatant was discarded and again 200 μl of PBS was added to each well. The cells were centrifuged at 1500 rpm and 4° C. for 10 minutes. The cells were suspended in 100 μl of PBS, and 300 μl of 1% paraformaldehyde was added thereto. A control was prepared using an isotype control antibody in the same manner as described above. The cells prepared as described above were analyzed using FACSCant™ II.

Results

Figure 15:
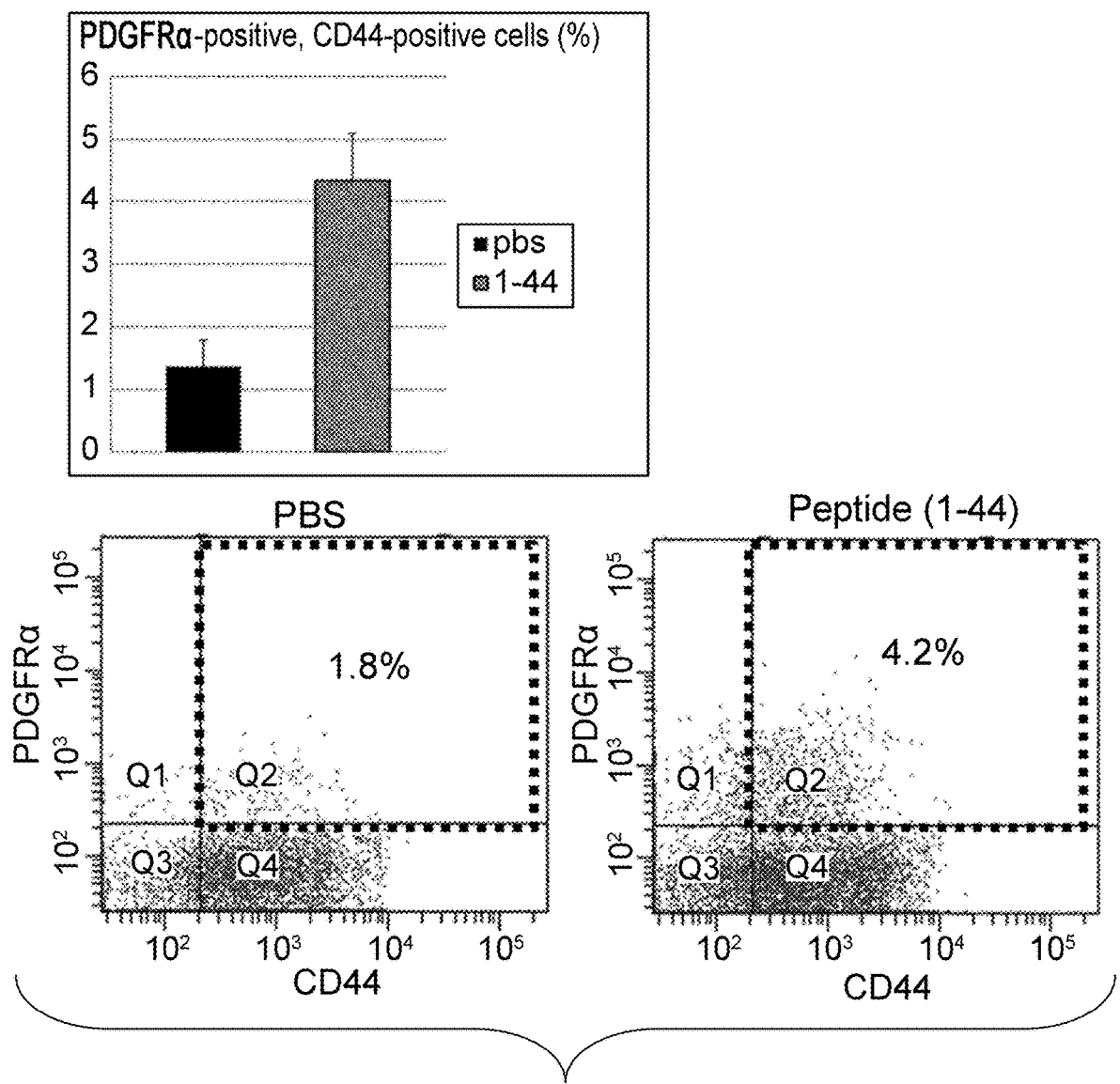
FIG. 15 shows mobilization of PDGFRα-positive CD44-positive cells into blood by a synthetic peptide (1-44) demonstrated by FACS.

In the negative control group (PBS administration group), the proportion of PDGFRα-positive, CD44-positive cells in the peripheral blood was 1.33% on average. Meanwhile, in the peptide (1-44) administration group, the proportion was increased to 4.33% on average (FIG. 15)

Discussion

When a peptide of amino acid positions 1 to 44 of HMGB1 was synthesized and administered to mice, PDGFRα-positive, CD44-positive cells were increased after 12 hours. In Example 8, the peptide exhibited in vitro migration-promoting activity on PDGFRα-positive, CD44-positive bone marrow mesenchymal stem cells. The present Example demonstrates that the peptide also recruits PDGFRα-positive, CD44-positive cells to the peripheral blood in vivo. Both PDGFRα positivity and CD44 positivity are markers for bone marrow mesenchymal stem cells. Bone marrow mesenchymal stem cells are known to be useful in regenerative medicine. Thus, intravenous administration of the peptide is expected to be effective to treat damaged tissues.

Example 13—Creation of Middle Cerebral Artery Thread Occlusion Model

Eight- to ten-week-old male Wister rats were used. Rats were anesthetized by isoflurane inhalation while warming on a keep-warm mat with a body temperature monitor. After confirming that the anesthetic effect was sufficient, cervical hair was removed to expose the skin. The surgical site was sterilized with alcohol. Along the cervical median line, the skin was incised with a scalpel. After the right external carotid artery was ligated and the right common carotid artery was pressurized to temporarily block the blood flow, an occlusion thread made of #4 monofilament nylon with siliconized tip was inserted into the right external carotid artery toward the right internal carotid artery. While releasing the pressure on the common carotid artery, the occlusion thread was advanced along with the blood stream from the internal carotid artery up to the bifurcation to the middle cerebral artery so that the blood flow was blocked. Furthermore, the thread around the right common carotid artery was ligated to completely block the blood flow for 50 minutes. After removing the occlusion thread and loosening the ligature at the common carotid artery, the skin was sutured to complete the surgery.

Administration of Therapeutic Agents

50 μg of synthetic peptide (1-44) was administered at the caudal vein. The first administration was carried out 6 hours after the production of cerebral infarction. Then, the peptide was administered five times at 24-hour intervals (five days in total).

Determination of Size of Cerebral Infarction

After 14 days of the final drug administration, the rats were given sufficiently deep anesthesia, and placed in a container filled with carbon dioxide. The complete arrest of heartbeat and breathing was confirmed. Brains were excised and immediately fixed by immersion in buffered 10% formalin. After paraffin embedding, thin sections were prepared and stained with hematoxylin-eosin. Four sections were prepared from each brain at 1.92 mm anterior to bregma (1.92), 0.60 mm anterior to bregma (0.60), 1.56 mm posterior to bregma (−1.56), and 3.24 mm posterior to bregma (−3.24), and the areas were compared.

Results

Figure 16:
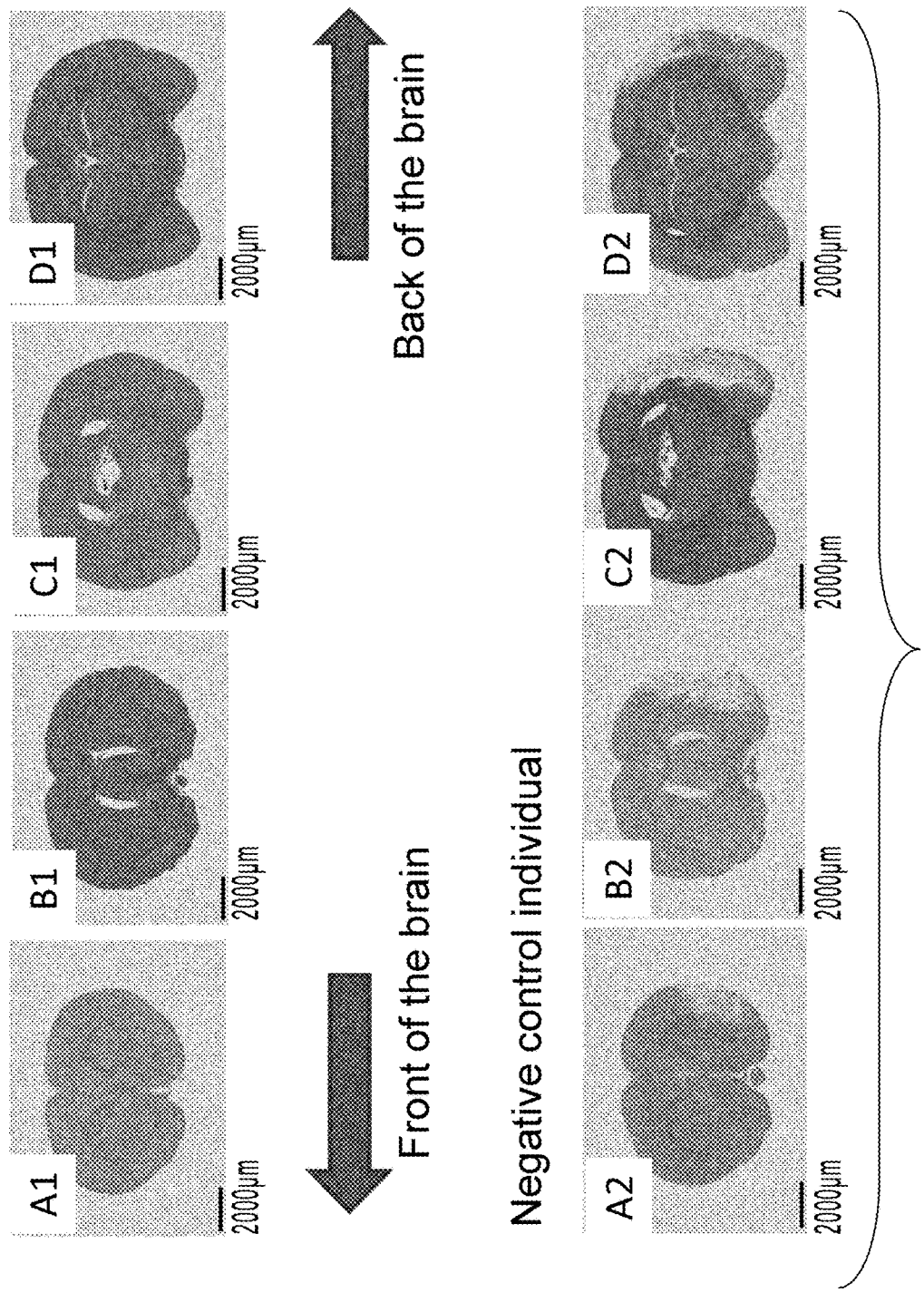
FIG. 16 is a cross-sectional photograph of the rat cerebral infarction model administered with a synthetic peptide (1-44) or a negative control, PBS. Reduction of the cerebral infarct size by the synthetic peptide (1-44) was observed.
Figure 17:
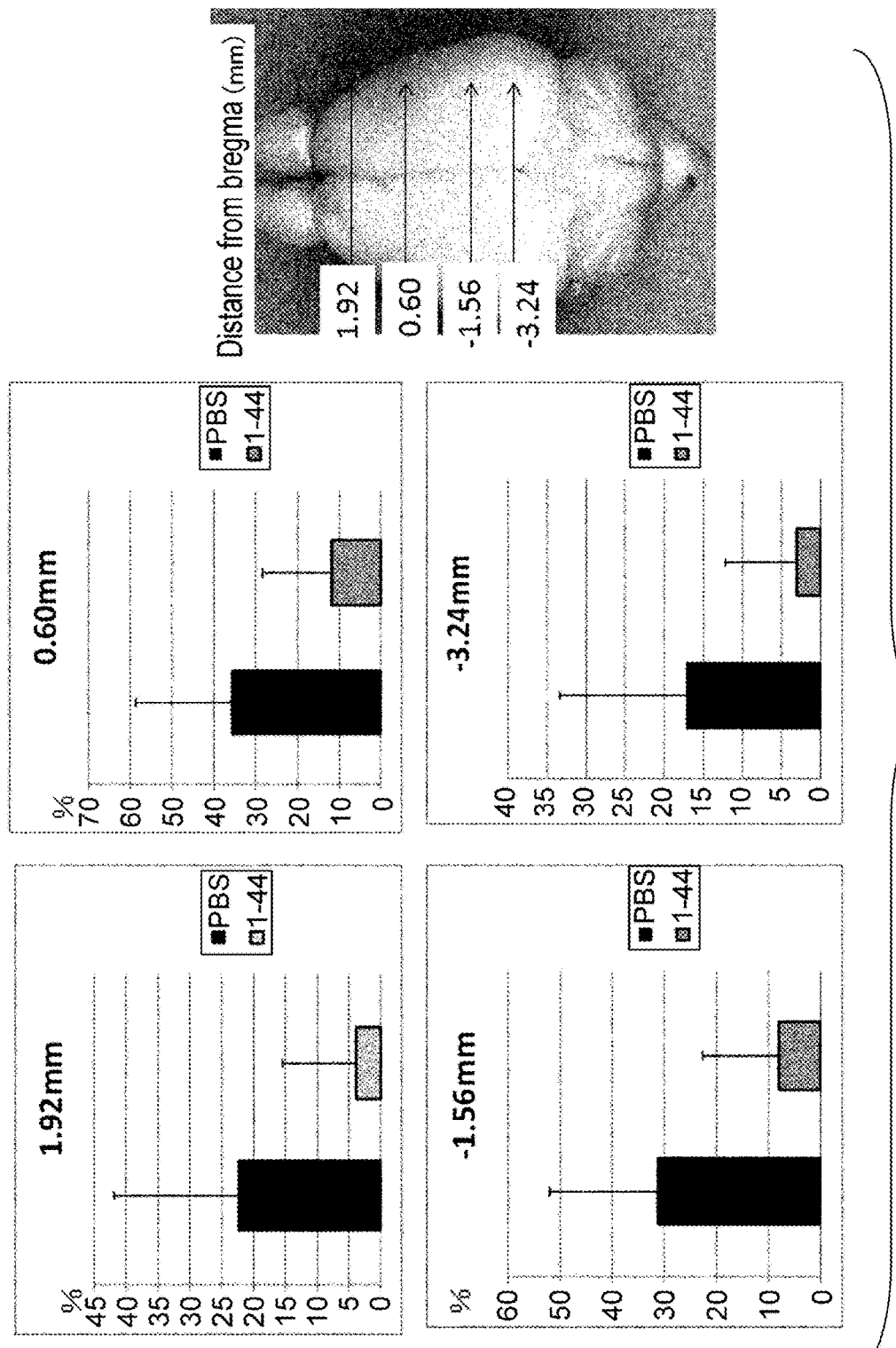
FIG. 17 is a set of diagrams and a photograph showing the ratio of cerebral infarct lesion area relative to the right brain area of the rat cerebral infarct model administered with a synthetic peptide (1-44) or a negative control, PBS. Four cross sections were produced from the same brain, and their respective areas were measured.

In the synthetic peptide (1-44) administration group (N=10), only one mouse showed expansion of the infarction to the cortex, while in the remaining 9 mice the infarction was limited in the basal nucleus (FIG. 16 A1; (1.92 mm anterior to bregma), B1 (0.60 mm anterior to bregma), C1 (1.56 mm posterior to bregma), and D1 (3.24 mm posterior to bregma)). Meanwhile, in the negative control group (N=11), 8 mice showed expansion of the infarction from the basal nucleus up to the cortex (FIG. 16 A2; (1.92 mm anterior to bregma), B2 (0.60 mm anterior to bregma), C2 (1.56 mm posterior to bregma), and D2 (3.24 mm posterior to bregma)). Furthermore, on each of the four prepared sections, the area of cerebral infarction in the right brain was measured to determine the % ratio to normal brain area in the right brain. In all sections, the infarction area in the synthetic peptide administration group was significantly reduced as compared to the negative control group (FIG. 17).

Discussion

It has recently been reported that the prognosis of patients with cerebral infarction is improved by intravenous administration of bone marrow mesenchymal stem cells of themselves. Thus, the therapeutic effect of intramedullary cells on cerebral infarction has been becoming clear. Further, while it is known from rodent experiments that bone marrow mesenchymal stem cells differentiate into osteoblasts, chondrocytes, adipocytes, and such, they have also been revealed to differentiate into various cells such as epithelial cells and neurons. Moreover, since bone marrow cells secrete a variety of growth factors and cellular growth factors, substances secreted by bone marrow cells that migrated to infarction sites can be expected to produce neuroprotective effects.

In the case of rats, it is known that by 48 hours after ischemia, cerebral infarction is almost established in 80% to 90% of its size, and then gradually expanded over subsequent 7 days. Furthermore, it is known that there is an area called "core", which, once ischemia occurs, inevitably becomes necrotized irrespective of treatment, and an area called "penumbra", of which necrosis could be avoided by treatment. Thus, preventing the necrosis of penumbra before infarct expansion is an aim of cerebral infarction therapy.

The cerebrum is primarily divided into basal nucleus and cerebral cortex. In particular, the basal nucleus is more vulnerable to hypoxia than the cerebral cortex, and is more easily damaged by cerebral infarction. The result of the present Example also demonstrates that the reduction of infarction by synthetic peptide (1-44) was primarily observed in the cortex while the basal nucleus necrotized in most cases. Since the cerebral cortex is the center of sensation and movement, improvement of these functions is very important for rehabilitation into society after treatment of cerebral infarction. In light of the existing circumstances where only a small number of effective therapeutic agents are available for cerebral infarction, the need for the peptides of the present invention as pharmaceutical agents is expected to be high.

In the experiment of the present Example, when the peptide was administered 6 hours after production of cerebral infarction, the effect of reducing the cerebral infarction size was seen after 19 days. The therapeutic effect is presumed to be due to the neuroprotective action of bone marrow cells and tissue regeneration caused by differentiation of the cells into neural tissues and such. It was strongly suggested that peptides consisting of a portion of HMGB1 could recruit cells to a damaged site not only when administered at or near the damaged site but also when administered into a vein which is a site different and distal to the damaged site. Meanwhile, the peptides described in Examples 4, 5, and 6 include some peptides whose migration-promoting activity seems too weak to be detected. It is considered that some of these peptides have activity that is below the detection limit of the assay method. The activity might be detected by optimizing the medium to dissolve the peptides, the measurement time for the migration-promoting activity, and the number of cells placed in the upper layer of the chamber. Regarding tPA, which is a pharmaceutical currently used for treating cerebral infarction, there are strict administration criteria to ensure prevention of side effects such as post-infarction hemorrhage: for example, it has to be administered within four hours after the onset of cerebral infarction, and diagnostic imaging is required. Since cerebral infarction occurs suddenly, it is difficult to predict the onset in advance. For this reason, most people who have developed cerebral infarction often become no longer suitable for tPA when they are seen in medical institutions because of expiry of the time limit. On the other hand, in the present Example, the therapeutic effect was obtained by administering the peptide 6 hours after production of cerebral infarction. Since the present peptide is considered to have no anticoagulant activity, it can be administered even later than 6 hours. Thus, the peptide is expected to be used for many people with cerebral infarction. Meanwhile, in this Example, the peptide was administered to rats (about 250 g/head) at 50 µg/head/administration. This corresponds to 200 µg/kg weight, and is considered appropriate as a dose of transveous administration to patients with cerebral infarction.

Figure 18A:
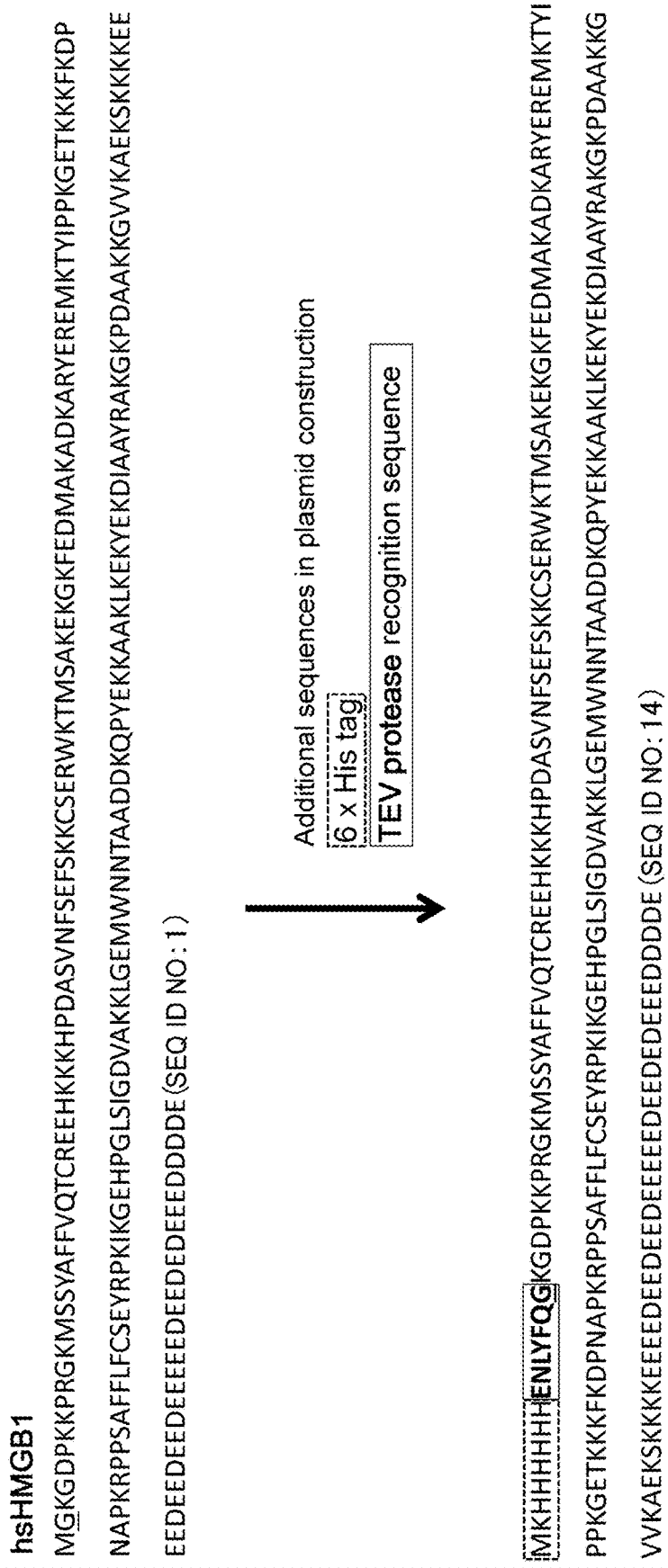
FIG. 18A shows addition of a 6×His tag and a TEV protease cleavage sequence to the N terminus of human HMGB1. A cDNA expressing this protein was newly made and inserted into an E. coli expression vector.

Example 14—Construction of Expression Vectors for HMGB1 Fragments, Protein and Peptide Expression, and Bone Marrow Mesenchymal Stem Cell Migration Assay Method The N terminal methionine (M) of human HMGB1 was deleted, and MKHHHHHHENLYFQ (SEQ ID NO: 11) was added instead. HHHHHH (SEQ ID NO: 12) is a tag (6×His tag) for use in purification of an expressed protein or peptide using a nickel column. ENLYFQG (SEQ ID NO: 13) is a sequence that is recognized by TEV protease (FIG. 18A). Furthermore, vectors were constructed in which a cDNA encoding a protein or peptide of interest (2-215, 2-84, 2-44, 45-84, 2-62, 2-70, 2-81, 2-170, 93-215, or 85-169) were inserted downstream of the T7 promoter and lac operator, the drug resistance gene was a kanamycin resistance gene, and the replication origins were pBR322 ori and f1 ori. A human HMGB1 protein or peptide that starts from the second amino acid can be prepared by cleaving with TEV protease a protein or peptide obtained using the above-described expression vector. BL-21(DE3) was transformed with the constructed plasmids. The bacteria were cultured in LB containing kanamycin while shaking at 37° C. overnight, and 5 ml of bacterial suspension was transferred into 100 ml of LB. The bacteria were cultured while shaking at 140 rpm and 37° C. The turbidity was measured with a turbidimeter, and, when OD reached 0.5 to 0.7, isopropyl-β-D-thiogalactopyranoside (IPTG) was added at a final concentration of 1 mM. After five hours of shaking culture at 37° C. for 2-215, 2-84, 2-70, 2-81, 2-170, 93-215, and 85-169, or after overnight shaking culture at 15° C. for 2-44, 45-84, and 2-62, the resulting bacteria were collected. The expressed protein and peptides were assessed by SDS-PAGE followed by protein staining and Western blotting with an antibody against the tag or anti-HMGB1 antibody.

Purification of respective HMGB1 fragments (2-215, 2-84, 2-44, 45-84, 2-62, 2-70, 2-81, 2-170, and 93-215)

3 ml of equilibration buffer (PBS (137 mM NaCl, 8.1 mM $Na_2HPO_4$, 2.68 mM KCl, 1.47 mM $KH_2PO_4$), 10 mM imidazole; pH 7.4) was added to collected bacterial cells. The bacterial cells were sonicated, and centrifuged at 15,000 rpm and 4° C. for 10 minutes. The supernatant was collected. 1 ml of His-Pur™ Ni-NTA Resin (Thermo Scientific) was loaded in Micro Bio-Spin column (Bio-Rad) and equilibrated with the equilibration buffer. A protein solution was loaded onto the column. After two minutes of centrifugation at 2000 rpm, the resin was washed with washing buffer (PBS, 25 mM imidazole; pH 7.4). The column was eluted with elution buffer (PBS, 250 mM or 500 mM imidazole) in a stepwise manner. Each fraction was subjected to SDS-PAGE (15% e-PAGEL® (ATTO)) to confirm the eluted protein. After affinity purification with a nickel column, ion-exchange chromatography was performed using Q Sepharose™ Fast Flow (GE Healthcare) for 2-215; using Q Sepharose™ Fast Flow (GE Healthcare) and SP Sepharose™ Fast Flow (GE Healthcare) for 93-215; or using SP Sepharose™ Fast Flow (GE Healthcare) for the remaining peptides.

Human HMGB1 fragments (2-215, 2-84, 2-44, 45-84, 2-62, 2-70, 2-81, and 2-170)

1 ml of each sepharose was loaded in Micro Bio-Spin column (Bio-Rad) and was equilibrated with PBS. After loading a solution of affinity purified protein, the column was washed with PBS, and eluted with elution buffer (20 mM HEPES, 1 M NaCl; pH 7.5). Each fraction was examined by SDS-PAGE.

Human HMGB1 fragment (93-215)

A solution of affinity purified protein was subjected to anion and cation exchange using Q and SP sepharose, respectively. Then, the flowthrough fraction from SP Sepharose™ Fast Flow was loaded onto Q Sepharose™ Fast Flow to perform anion exchange.

Each fraction was examined by SDS-PAGE.

Human HMGB1 fragment (85-169)

One ml of buffer (PBS, 10 mM imidazole; pH 7.4) was added to 0.1 g each of the collected bacterial cells. The bacterial cells were sonicated and centrifuged at 20,000 rpm and 4° C. for one hour. The supernatant was collected and purified by column chromatography using BioLogic Duo-Flow (Bio-Rad). First, affinity purification was carried out with 5 ml of HisTrap™ FF (GE Healthcare) using a bacterial lysis buffer (PBS, 10 mM imidazole (pH 7.4)) as Buffer A and PBS (pH 74) containing 500 mM imidazole as Buffer B. After the column was equilibrated with Buffer A, a protein solution was loaded onto it. Washing and purification were performed with the program described below. The program used is as follows:

Isocratic Flow (Buffer A: 97%, Buffer B: 3%, 20 ml)→Linear Gradient (Buffer A: 97%→0%, Buffer B: 3%→100%, 20 ml)→Isocratic Flow (Buffer B: 100%, 20 ml)→Fraction Collection (2 ml each; 20 to 40 ml)

Each fraction was examined by SDS-PAGE.

Then, ion-exchange purification was performed using 5 ml column of HiTrap™ SP HP (GE Healthcare) for 85-169, and PBS (pH 7.4) as Buffer A, and 20 mM HEPES buffer (pH 7.5) containing 1 M NaCl as Buffer B. After the column was equilibrated with an appropriate amount of Buffer A, a solution of affinity purified protein was loaded onto it. Washing and purification were performed with the program described below. The program used is as follows:

Isocratic Flow (Buffer A: 100%, Buffer B: 0%, 10 ml)→Isocratic Flow (Buffer A: 50%, Buffer B: 50%, 2 ml)→Isocratic Flow (Buffer A: 0%, Buffer B: 100%, 20 ml)→Fraction Collection (1 ml each; 10 to 32 ml)

Each fraction was examined by SDS-PAGE.

Concentration Determination

The concentration of each fragment was determined in BSA equivalents using Bradford method (Bio-Rad Protein Assay).

Migration Assay

Each of the above-described peptides was assessed for migration-promoting activity on bone marrow mesenchymal stem cell line MSC-1. Each fragment in phosphate buffer containing 500 mM NaCl was diluted at a final concentration of 2 µM with two volumes of DMEM, and added to the lower layer of a chamber, while MSC-1 suspended in DMEM containing 10% FBS was placed in the upper layer. Polycarbonate membrane with 8-µm pores was inserted between both layers. After four hours of incubation in an incubator under 5% $CO_2$ at 37° C., cells that migrated from the upper layer to the lower layer were detected by using Diff-Quik Stain™.

Results

All of 2-215, 2-84, 2-44, 45-84, 2-62, 2-70, 2-81, 2-170, and 93-215 showed migration-promoting activity on bone marrow mesenchymal stem cells (FIG. 18B). When the migration-promoting activity of 2-215 is taken as 1, the activities of 2-84, 2-44, and 45-84 per molar concentration were 2.37, 1.82, and 2.04 times, respectively, and those per equal mass were 5.5, 7.1, and 8.1 times, respectively (FIGS. 18C and 18D).

Discussion

Fragmentation of the N-terminal of human HMGB1 (2-215) produced in *E. coli* resulted in an increase in the migration-promoting activity. Furthermore, at least two regions on the N terminal side, 2-44 and 45-84, exhibited migration-promoting activity. This is consistent with the result for the HMGB1 fragments produced by eukaryotic cell culture (HEK293 cells). It is presumed that the fragmentation results in exposure of epitopes to the receptor on MSC-1, and thereby facilitates the receptor binding. Although some proteins lose their activity by fragmentation, the present protein showed rather increased activity as a result of fragmentation. It is known that proteins expressed in eukaryotic cells such as HEK293 undergo post-translational modification such as glycosylation. The presence of such modification may affect the activity of receptor ligands. Thus, the fact that not only the protein produced in *E. coli*, which does not perform the same post-translational modification as eukaryotic cells, but also the fragments produced in *E. coli* retain the activity suggests that post-translational modification is not essential for the activity of the fragments. The findings described above demonstrate that fragmentation of HMGB1 enables development of highly active agents for recruiting bone marrow mesenchymal stem cells. Furthermore, since post-translational modification is not essential, production methods using *E. coli* or chemical synthesis are possible, enabling production of preparations more stable in quality at lower costs. Moreover, comparison between the peptides described in this Example and those described in other Examples (for example, comparison between 1-44 and 2-44 or between 1-84 and 2-84) revealed that the migration-promoting activity was not affected by the presence of the first methionine in the HMGB1 protein. Hence, when a peptide has migration-promoting activity, a peptide in which the first methionine is removed from the peptide is also considered to have migration-promoting activity. Alternatively, when a peptide lacking the first methionine has migration-promoting activity, a peptide to which the first methionine is added is also considered to have migration-promoting activity.

Example 15

Methods

The N terminal methionine (M) was deleted from human HMGB1, and instead MKHHHHHHENLYFQ (SEQ ID NO: 11) was added to the N terminus. HHHHHH (SEQ ID NO: 12) is a tag (6×His tag) for use in purification of an expressed protein or peptide using a nickel column. ENLYFQG (SEQ ID NO: 13) is a sequence that is recognized by TEV protease (FIG. 18A). Furthermore, vectors were constructed in which a cDNA encoding a protein or peptide of interest (89-215, 89-205, 89-195, or 89-185) was inserted downstream of T7 promoter and lac operator, and the drug resistance gene was a kanamycin resistance gene, and the replication origins were pBR322 ori and fl ori. A human HMGB1 protein or peptide that starts from the second amino acid can be prepared by cleaving with TEV protease a protein or peptide obtained using the above-described expression vector.

BL-21(DE3) was transformed with the constructed plasmids. The bacteria were cultured in LB containing kanamycin while shaking at 37° C. overnight, and 5 ml of bacterial suspensions were transferred into 100 ml of LB, The bacteria were cultured while shaking at 140 rpm and 37° C. The turbidity was measured with a turbidimeter, and, when OD reached 0.5 to 0.7, isopropyl-β-D-thiogalactopyranoside (IPTG) was added at a final concentration of 1 mM. After overnight shaking culture at 15° C., the bacterial cells for human HMGB1 fragments (89-215, 89-205, 89-195, and 89-185) were harvested. The expressed protein and peptides were examined by SDS-PAGE followed by protein staining and Western blotting with an antibody against the tag or anti-HMGB1 antibody.

Purification of Respective HMGB1 Fragments (89-215, 89-205, 89-195, and 89-185)

Two ml of buffer (PBS, 10 mM imidazole; pH 7.4) was added to 0.1 g each of the collected bacterial cells. The bacterial cells were sonicated and centrifuged at 20,000 rpm and 4° C. for one hour. The supernatant was collected and purified by column chromatography using BioLogic DuoFlow (Bio-Rad).

Human HMGB1 Fragment (89-215)

One ml of buffer (PBS, 10 mM imidazole; pH 7.4) was added to 0.1 g each of the collected bacterial cells. The bacterial cells were sonicated and centrifuged at 20,000 rpm and 4° C. for one hour. The supernatant was collected and purified by column chromatography using BioLogic Duo-Flow (Bio-Rad). First, affinity purification was carried out with 5 ml of HisTrap™ FF (GE Healthcare) using a bacterial lysis buffer (PBS, 10 mM imidazole (pH7.4)) as Buffer A and PBS (pH 7.4) containing 500 mM imidazole as Buffer B. After the column was equilibrated with Buffer A, a protein solution was loaded onto it. Washing and purification were performed with the program described below. The program used is as follows:

Isocratic Flow (Buffer A: 97%, Buffer B: 3%, 20 ml)→Linear Gradient (Buffer A: 97%→0%, Buffer B: 3%→100%, 20 ml)→Isocratic Flow (Buffer B: 100%, 20 ml)→Fraction Collection (2 ml each; 20 to 40 ml)

Each fraction was examined by SDS-PAGE.

Then, ion-exchange purification was performed using 5 ml of HiTrap™ Q HP (GE Healthcare) for 89-215, and PBS (pH 7.4) as Buffer A, and 20 mM HEPES buffer (pH 7.5) containing 1 M NaCl as Buffer B. After the column was equilibrated with an appropriate amount of Buffer A, a solution of affinity purified protein was loaded onto it. Washing and purification were performed with the program described below. The program used is as follows:

Isocratic Flow (Buffer A: 100%, Buffer B: 0%, 10 ml)→Isocratic Flow (Buffer A: 50%, Buffer B: 50%, 2 ml)→Isocratic Flow (Buffer A: 0%, Buffer B: 100%, 20 ml)→Fraction Collection (1 ml each; 10 to 32 ml)

Each fraction was examined by SDS-PAGE.

Human HMGB1 Fragments (89-205, 89-195, and 89-185)

Solutions of soluble proteins were prepared in the same manner as human HMGB1 fragment (89-215). Then, the following gradient elution was performed by each column chromatography.

First, affinity purification was carried out using 5 ml of HisTrap™ FF, Buffer A (PBS (pH7.4) containing 10 mM imidazole), and Buffer B (PBS (pH 7.4) containing 500 mM imidazole). After the column was equilibrated with Buffer A, a protein solution was loaded onto it. Washing and purification were performed with the program described below. The program used is as follows: →Isocratic Flow (Buffer A: 97%, Buffer B: 3%, 50 ml)→Linear Gradient (Buffer A: 97%→0%, Buffer B: 3%→100%, 120 ml)→Fraction Collection (5 ml each; 50 to 170 ml)

Each fraction was examined by SDS-PAGE.

Then, ion-exchange purification was performed using 5 ml column of HiTrap™ Q HP for human HMGB1 fragments (89-215) and (89-205), and 5 ml column of HiTrap™ Q HP for the other fragments. PBS (pH 7.4) was used as Buffer A, while 7×PBS (pH 7.4) was used as Buffer B. After the column was equilibrated with an appropriate amount of Buffer A, a solution of affinity purified protein was loaded onto it. Washing and purification were performed with the program described below. The program used is as follows:

Isocratic Flow (Buffer A: 100%, Buffer B: 0%, 50 ml)→Linear Gradient (Buffer A: 100%→0%, Buffer B: 0%→100%, 50 ml)→Isocratic Flow (Buffer A: 0%, Buffer B: 100%, 5 ml)→Fraction Collection (3 ml each; 50 to 105 ml)

Each fraction was examined by SDS-PAGE.

Concentration Determination

The concentration of each fragment was determined in BSA equivalents using Bradford method (Bio-Rad Protein Assay).

Migration Assay

Each of the above-described peptides was examined for migration-promoting activity on bone marrow mesenchymal stem cell line MSC-1. Each fragment in phosphate buffer containing 500 mM NaCl was diluted at a final concentration of 2 µM with two volumes of DMEM, and added to the lower layer of a chamber, while MSC-1 dispersed in DMEM containing 10% FBS was placed in the upper layer. Polycarbonate membrane with 8-µm pores was inserted between the upper and lower layers. After four hours of incubation in an incubator under 5% $CO_2$ at 37° C., cells that migrated from the upper layer to lower layer were detected by using Diff-Quik Stain™.

Results

Figure 19A:
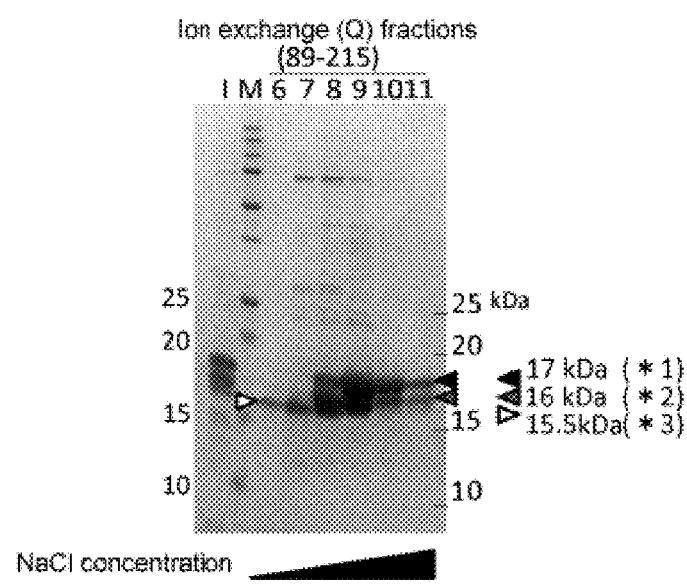
FIG. 19A is an SDS-PAGE photograph of fractions obtained by anion exchange column purification of an HMGB1 fragment consisting of amino acids of positions 89 to 215 that was produced using E. coli and subjected to nickel affinity purification (I: input). M is a molecular weight marker. A 15.5 kDa fragment (*3) was eluted under a low salt concentration; and a 16 kDa fragment (*2) and a 17 kDa fragment (*1) were eluted in order as the salt concentration increased. (*3) and (*2) are presumed to be degradation products of (*1).

After affinity purification of human HMGB1 fragment (89-215) with a nickel column, gradient elution with increasing salt concentration was performed using ion-exchange chromatography (Q column). A 15.5-kDa peptide was fractionated into fractions 6 and 7; 15.5-, 16-, and 17-kDa peptides were fractionated into fractions 8 and 9; and 16- and 17-kDa peptides were fractionated into fractions 10 and 11 (FIG. 19A).

Figure 19B:
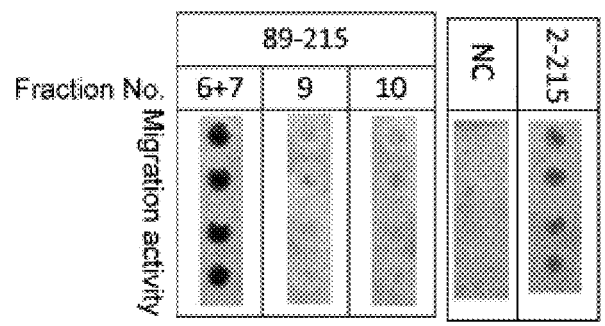
FIG. 19B is a photograph showing migration-promoting activity of the fractions obtained in Fig. A on an established PDGFRα-positive bone marrow mesenchymal stem cell line. NC is negative control, and 2-215 is positive control. The fragment with the lowest molecular weight (*3), which was considered to be a cleaved fragment, was found to have a stronger activity than longer fragments (*1) and (*2). The activity was greater than that of 2-215.

A mixed sample (6+7) of fractions 6 and 7, and fractions 9 and 10 were tested for migration-promoting activity on bone marrow mesenchymal stem cells (MSC-1). The activity of the mixed sample of fractions 6 and 7 (6+7) was strong, while those of fractions 9 and 10 were weak (FIG. 19B).

Figure 19C:
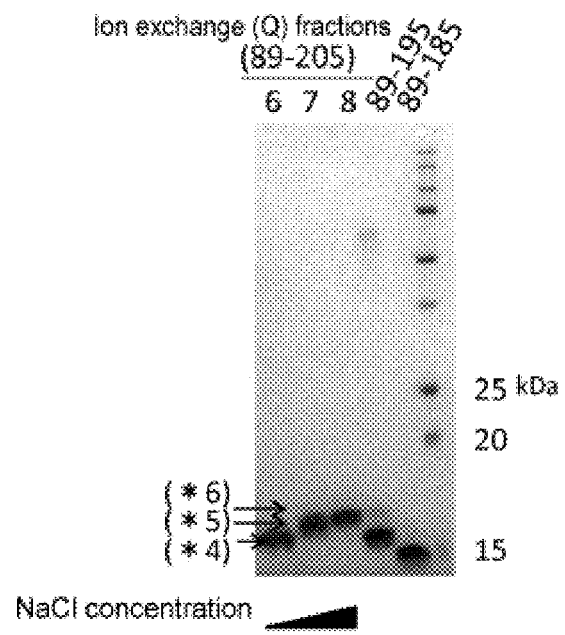
FIG. 19C is an SDS-PAGE photograph of fractions obtained by anion exchange column of an HMGB1 fragment consisting of amino acids of positions 89 to 205 that was produced using *E. coli* and subjected to nickel affinity purification (I: input). The shortest fragment (*4) was eluted under a low salt concentration; and as the salt concentration increased, longer fragments (*5) and (*6) were eluted. (*5) and (*6) are predicted to be degradation products of (*4). Also, purified HMGB1 fragments 89-195 and 89-185 were run on SDS-PAGE at the same time. M is a molecular weight marker.

After affinity purification of human HMGB1 fragment (89-205) with a nickel column, gradient elution with increasing salt concentration was carried out using ion-exchange chromatography (Q column). The shortest fragment (*4) was eluted first in fraction 6, and the next shortest fragment (*5) and then the longest fragment (*6) were eluted in fraction 7. Meanwhile, 89-195 and 89-185 were purified as a single fragment by affinity purification using a nickel column (FIG. 19C).

Figure 19D:
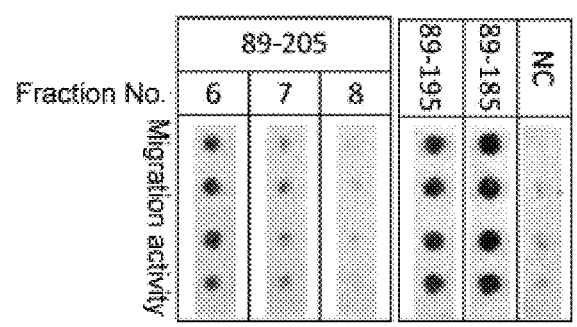
FIG. 19D is a photograph showing migration-promoting activity of the fractions obtained in Fig. C on an established PDGFRα-positive bone marrow mesenchymal stem cell line. NC is negative control. The fragment with the lowest molecular weight (*4), which was considered to be a cleaved fragment, was found to have a stronger activity than longer fragments (*5) and (*6). Meanwhile, HMGB1 fragments whose C terminus was further shortened in advance, i.e. 89-195 and 89-185, showed a much stronger activity.

Fractions 6, 7, and 8 were examined for migration-promoting activity on bone marrow mesenchymal stem cells (MSC-1). Fraction 6 showed strong activity, and the activity was decreased as the fraction number increased. Meanwhile, 89-195 and 89-185 showed stronger activity than any fragments between positions 89 and 215 (FIG. 19D)

Discussion

Human HMGB1 fragments (89-215, 89-205, 89-195, and 89-185) were prepared using *E. coli*. 89-215 and 89-205 exhibited weak migration-promoting activity on bone marrow mesenchymal stem cells. However, they underwent cleavage that seemed to be caused by protease derived from *E. coli* (FIGS. 19A and 19C), and short fragments exhibited strong activity (FIGS. 19B and 19D). Meanwhile, 89-195 and 89-185 showed strong migration-promoting activity on bone marrow mesenchymal stem cells (FIGS. 19C and 19D). The C-terminal amino acids of positions 186 to 215 of HMGB1 contain a repeat sequence of glutamine and aspartic acid. The sequence is said to contribute to protein stabilization. The present study for the first time demonstrated that this portion suppressed the migration-promoting activity of HMGB1 fragment (89-215) and thus the activity could be increased by removing this sequence. The C-terminal glutamic acid/aspartic acid repeat sequence (the amino acid sequence from positions 186 to 215) in HMGB1 is called "acidic tail", and has been reported to be essential for the binding to RAGE. Meanwhile, based on the fact that RAGE serves as the receptor responsible for HMGB1-mediated migration of dendritic cells and such, it was once predicted that the C-terminal portion and the RAGE ligand portion would be indispensable to exert the migration-promoting activity. Surprisingly, in fact, the lack of the C-terminal was found to be more advantageous for the migration-promoting activity on bone marrow mesenchymal stem cells. This was not known until it was discovered that, when the C-terminalcontaining HMGB1 fragment was produced in *E. coli*, degradation products that seemed to be produced by *E. coli*-derived protease exhibited stronger migration-promoting activity than the intact HMGB1 fragment and that when an HMGB1 fragment lacking the C terminus was produced, it exhibited stronger activity than the C-terminal-intact HMGB1 fragment. In general, a particular activity of protein is contributed by only a single region; however, surprisingly, HMGB1 had multiple regions that contribute to its migration-promoting activity on bone marrow mesenchymal stem cells, and more surprisingly, the activity of each region per equal number of molecules was about twice that of the full-length HMGB1. In addition, although biologically active peptides in general become more unstable and less active as their length becomes shorter, surprisingly, some shorter fragments had stronger activity than longer fragments.

Example 16

Methods

The N terminal methionine (M) was deleted from human HMGB1, and instead MKHHHHHHENLYFQ (SEQ ID NO: 11) was added to the N terminus. HHHHHH (SEQ ID NO: 12) is a tag (6×His tag) for use in purification of an expressed protein or peptide using a nickel column. ENLYFQG (SEQ ID NO: 13) is a sequence that is recognized by TEV protease (FIG. 18A), Furthermore, vectors were constructed in which a cDNA encoding a protein or peptide of interest (85-169, 2-215) was inserted downstream of T7 promoter and lac operator, the drug resistance gene was a kanamycin resistance gene, and the replication origins were pBR322 ori and fl ori. A human HMGB1 protein or peptide that starts from the second amino acid can be prepared by cleaving with TEV protease a protein or peptide obtained using the above-described expression vector.

BL-21(DE3) was transformed with the constructed plasmids. The bacteria were cultured in LB containing kanamycin while shaking at 37° C. overnight, and 5 ml of bacterial suspensions were transferred into 100 ml of LB. The bacteria were cultured while shaking at 140 rpm and 37° C. The turbidity was measured with a turbidimeter, and, when. OD reached 0.5 to 0.7, isopropyl-β-D-thiogalactopyranoside (IPTG) was added at a final concentration of 1 mM. After overnight shaking culture at 15° C., the bacterial cells for human HMGB1 fragment (85-169) were harvested. The expressed protein and peptides were examined by SDS-PAGE followed by protein staining and Western blotting with an antibody against the tag or anti-HMGB1 antibody.

One ml of buffer (PBS, 10 mM imidazole; pH 7.4) was added to 0.1 g each of the collected bacterial cells. The bacterial cells were sonicated and centrifuged at 20,000 rpm and 4° C. for one hour. The supernatant was collected and purified by column chromatography using BioLogic Duo-Flow (Bio-Rad). First, affinity purification was carried out with 5 ml of HisTrap™ FF (GE Healthcare) using a bacterial lysis buffer (PBS, 10 mM imidazole (pH7.4)) as Buffer A and PBS (pH 7.4) containing 500 mM imidazole as Buffer B. After the column was equilibrated with Buffer A, a protein solution was loaded onto it. Washing and purification were performed with the program described below. The program used is as follows:
Isocratic Flow (Buffer A: 97%, Buffer B: 3%, 20 ml) Linear Gradient (Buffer A: 97%→0%, Buffer B: 3%→100%, 20 ml)→Isocratic Flow (Buffer B: 100%, 20 ml)→Fraction Collection (2 ml each; 20 to 40 ml)
Each fraction was examined by SDS-PAGE.

Concentration Determination

The concentration of each recombinant protein was determined in BSA equivalents using Bradford method (Bio-Rad Protein Assay).

Migration Assay

Each of the above-described peptides was examined for migration-promoting activity on bone marrow mesenchymal stem cell line MSC-1. Each fragment in phosphate buffer containing 500 mM NaCl was diluted at a final concentration of 2 µM with two volumes of DMEM, and added to the lower layer of a chamber, while MSC-1 dispersed in DMEM containing 10% FBS was placed in the upper layer. Polycarbonate membrane with 8-µm pores was inserted between the upper and lower layers. After four hours of incubation in an incubator under 5% $CO_2$ at 37° C., cells that migrated from the upper to lower layer were detected by using Diff-Quik Stain™.

Results

Figures 20A, 20B, 20C:
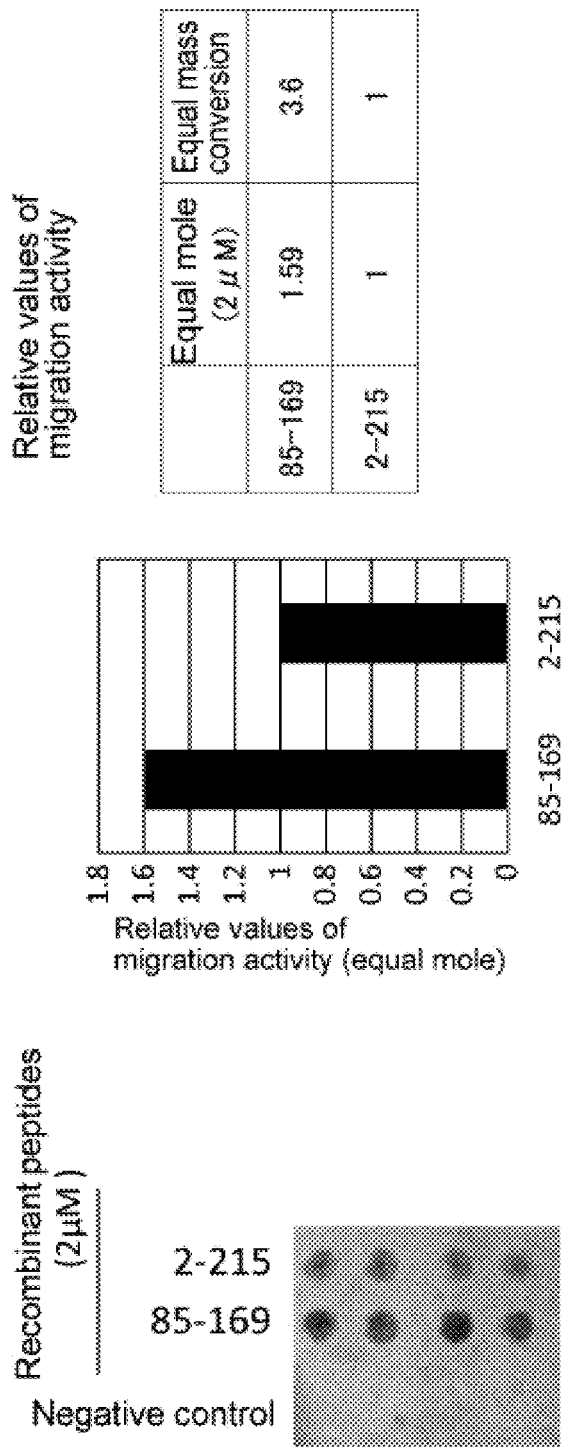
FIG. 20A is a photograph showing migration-promoting activity of the HMGB1 fragment 85-169. A stronger activity than that of the positive control, HMGB1 fragment 2-215, was observed.
FIG. 20B is a graph of average values of the quantified migration activities in FIG. 20A.
FIG. 20C is a table showing the average values in FIG. 20B.

Human HMGB1 fragment (85-169) exhibited stronger migration-promoting activity on bone marrow mesenchymal stem cells than human HMGB1 fragment (2-215) (FIG. 20A). When the migration-promoting activity is taken as 1, the activity per molar was 1.59 times, and the activity per equal mass was 3.6 times (FIGS. 20B and 20C).

Discussion

Like human HMGB1 fragments (89-195) and (89-185), human HMGB1 fragment (85-169) showed stronger migration-promoting activity on bone marrow mesenchymal stem cells than (2-215). From the above-described finding, it is presumed that at least one sequence with the activity of recruiting bone marrow mesenchymal stem cells is present within the amino acids of positions 85-185. In Example 1, HMGB1 fragment 85-169 produced in HEK293 did not show migration-promoting activity. In the present Example, however, HMGB1 fragment 85-169 produced in *E. coli* exhibited migration-promoting activity. This difference is presumably due to significant diminishment or loss of the migration-promoting activity depending on the production method. Since eukaryotes such as HEK293 and prokaryotes such as *E. coli* are different in post-translational modification, folding, and such, even the same proteins or peptides produced by them often have different properties.

The present study revealed that the amino acid sequence of HMGB1 has at least three sequences with the activity of recruiting bone marrow mesenchymal stem cells, and their activity was regulated through the suppression by the C-terminal glutamic acid/aspartic acid repeat sequence. By preparing HMGB1 fragments that lack the C-terminal suppressive sequence, it is possible to produce highly active preparations having the effect of recruiting bone-marrow stem cells.

Example 17—Mouse Mesenchymal Stem Cell Migration Activity (1)

Methods

Purification of HMGB1 Fragments

Inverse PCR was carried out using KOD-Plus-ver.2 (Toyobo). The above-described expression vector for HMGB1 fragment containing the amino acids of positions 2 to 215 of human HMGB1 was used as a template plasmid. cDNAs encoding the amino acids of positions 2 to 205, the amino acids of positions 2 to 195, the amino acids of positions 2 to 185 were amplified by PCR, together with the N-terminal histidine tag, TEV protease recognition sequence, and the plasmid backbone. The gene products prepared from the PCR products are proteins in which a histidine tag, a TEV protease recognition sequence, and a human HMGB1 fragment are aligned in tandem. The template plasmid was digested by adding restriction enzyme DpnI (Toyobo) to the PCR products. Then, the PCR products were phosphorylated using T4 Polynucleotide kinase (NEB), and self-ligated with ligase (2× Quick Ligase (NEB); or Ligation Convenience kit (Nippongene)). The products were used to transform *E. coli* JM109, and colonies were obtained via kanamycin selection, Plasmid extraction was carried out using GenElute Plasmid Miniprep kit (SIGMA-ALDRICH). After determining the nucleotide sequences by sequencing analysis, *E. coli* BL21 (DE3) was transformed with the plasmids to give colonies.

Induction of Expression

Each colony was cultured in a medium containing kanamycin at a final concentration of 50 mg/l while shaking at 37° C. overnight. 5 ml of the bacterial suspension was transferred into 100 ml of LB. The bacteria were cultured at 37° C. while shaking at 140 rpm. The turbidity was measured with a turbidimeter, and, when OD reached 0.5 to 0.7, isopropyl-β-D-thiogalactopyranoside (IPTG) was added at a final concentration of 1 mM. After overnight shaking culture at 15° C., the bacterial cells were collected.

Purification of Recombinant Proteins 12 ml (25-50 mg/ml) of equilibration buffer (PBS (137 mM NaCl, 8.1 mM $Na_2HPO_4$, 2.68 mM KCl, 1.47 mM $KH_2PO_4$), 10 mM imidazole; pH7.4) was added to the collected bacterial cells, and leupeptin hydrochloride was added at a final concentration of 5 µg/ml thereto. The bacterial cells were sonicated and centrifuged at 15,000 rpm and 4° C. for 60 minutes. The supernatant was collected and an aliquot thereof was examined by Western blotting using an anti-human HMGB1 antibody to confirm the expression of the protein of interest. The remaining supernatant was sterilized by filtering through a 0.45-µm filter. The protein of interest was purified by column chromatography using Bio-Logic DuoFlow (Bio-Rad).

First, affinity purification was performed with 5 ml of HisTrap™ FF using Buffer A (PBS, 10 mM imidazole (pH7.4)) and Buffer B (PBS, 500 mM imidazole (pH 7.4)). After the column was equilibrated with Buffer A, a protein solution was loaded onto it. Washing and purification were performed with the program described below.

Program:
Isocratic Flow (Buffer A: 97%, Buffer B: 3%, 50 ml)
Linear Gradient (Buffer A: 97%→0%, Buffer B: 3%→100%, 120 ml)
Fraction Collection (5 ml each; 50 to 170 ml)
Each fraction was examined by SDS-PAGE (5-20% e-PAGEL® (ATTO)).

Then, ion-exchange purification was performed using 5 ml column of HiTrap™ Q HP for GNX-E-022 only, and 5 ml of HiTrap™ SP HP for the others. PBS (pH 7.4) was used as Buffer A, while 7×PBS (pH 7.4) was used as Buffer B. After the column was equilibrated with an appropriate amount of Buffer A, a solution of affinity purified protein was loaded onto it. Washing and purification were performed with the program described below.

Program:
Isocratic Flow (Buffer A: 100%, Buffer B: 0%, 50 ml, 4 ml/min)
Linear Gradient (Buffer A: 100%→0%, Buffer B: 0%→100%, 50 ml, 4 ml/min)
Isocratic Flow (Buffer A: 0%, Buffer B: 100%, 5 ml, 4 ml/min)
Fraction Collection (3 ml each; 50 to 105 ml)

Each fraction was subjected to SDS-PAGE followed by protein staining to confirm purified proteins.

Concentration Determination

The concentration of recombinant proteins was determined in BSA equivalents using Bradford method (Bio-Rad Protein Assay).

Migration Assay

Each of the above-described peptides was examined for migration-promoting activity on bone marrow mesenchymal stem cell line MSC-1. Each fragment in phosphate buffer containing 500 mM NaCl was diluted at a final concentration of 2 µM with two volumes of DMEM, and added to the lower layer of a chamber, while MSC-1 dispersed in DMEM containing 10% FBS was placed in the upper layer. Polycarbonate membrane with 8-µm pores was inserted between the upper and lower layers. After four hours of incubation in an incubator under 5% $CO_2$ at 37° C., cells that migrated from the upper to lower layer were detected by using Diff-Quik Stain™.

Results

Figure 21A:
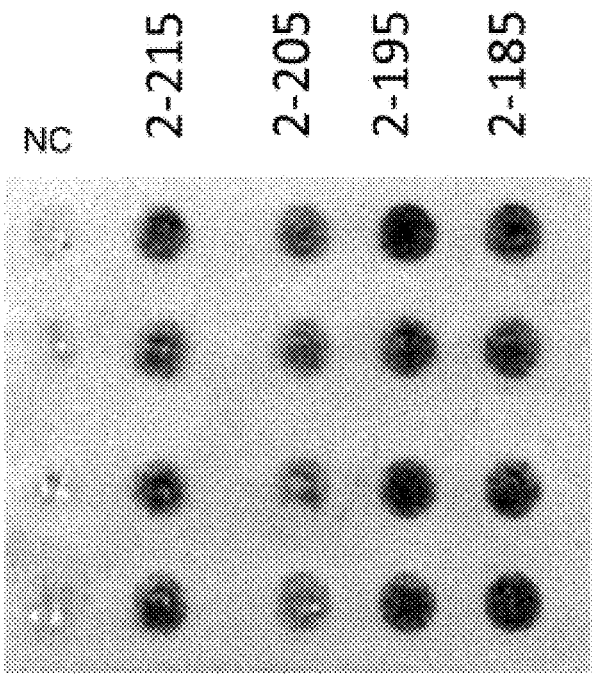
FIG. 21A shows migration activity of bone marrow mesenchymal stem cell line (MSC-1) towards HMGB1 fragments produced using *E. coli*: 2-215, 2-205, 2-195, and 2-185.

Fragments 2-195 and 2-185 showed stronger migration-promoting activity than fragments 2-215 and 2-205 (FIG. 21A).

Discussion

The fragment from positions 186 to 215 is an aspartic acid/glutamic acid repeat sequence of 30 amino acids in total, and is called "acidic tail". The data described above suggests that the migration-promoting activity of HMGB1 on bone marrow mesenchymal stem cells is strongly suppressed by the acidic tail, and in particular the C-terminal 20-amino acid sequence is involved in the suppression. Based on the data described earlier, several active domains for the migration-promoting effect of HMGB1 on bone marrow mesenchymal stem cells were identified. Further detailed experiments were needed to clarify whether the acidic tail suppresses the activity of all these domains.

Human Mesenchymal Stem Cell Migration Activity (2)

Methods

Human HMGB1 fragments (2-215, 2-84, 2-44, 45-84, 85-169, 89-185, 89-195, and 89-205) were produced in *E. coli* and purified using appropriate columns in the same manner as described in Examples 14, 15, and 16 above. However, 89-215 was purified by the same method as used for 89-205 in Example 15.

Concentration Determination

The concentration of each fragment was determined in BSA equivalents using Bradford method (Bio-Rad Protein Assay).

Migration Assay

Using human-derived bone marrow mesenchymal stem cells, each fragment was examined by the same migration assay performed on mouse-derived bone marrow mesenchymal stem cells (MSC-1) as described above. The fragments were used at a final concentration of 2 µM. The human-derived bone marrow mesenchymal stem cells used were hMSC (human Mesenchymal Stem Cell, Takara) at fourth passage. The growth medium used was a mesenchymal stem cell growth medium (MF medium, TOYOBO). The cells were cultured in an incubator under 5% $CO_2$ at 37° C. The medium was changed with a fresh medium every two to four days. The cells were passaged when they reached 80% confluency.

Results

Figure 21B:
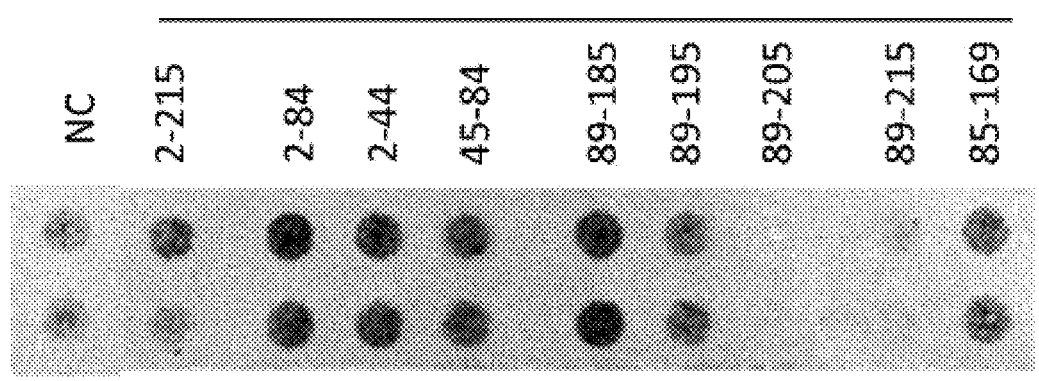
FIG. 21B is a photograph showing migration-promoting activity of HMGB1 fragments produced using *E. coli* on human bone marrow mesenchymal stem cells.

Regarding the human HMGB1 fragments (2-215, 2-84, 2-44, and 45-84), the activity of HMGB1 fragments (2-84, 2-44, and 45-84) was greater than human HMGB1 fragment (2-215) as with the case of Example 14. As to human HMGB1 fragments (89-185, 89-195, 89-205, and 89-215), active human HMGB1 fragments (89-185 and 89-195) with a shortened C-terminal acidic tail exhibited stronger activity as with the case of Example 15. Meanwhile, the activity of human HMGB1 fragment (85-169) was greater than that of human HMGB1 fragment (2-215) as with the case of Example 16 (FIG. 21B).

Discussion

All fragments showed migration-promoting activity on human-derived bone marrow mesenchymal stem cells as with the case of mouse-derived bone marrow mesenchymal stem cells. It was demonstrated that independent domains having migration-promoting activity on human bone marrow mesenchymal stem cells were located at least in human HMGB1 fragments (2-44, 45-84, and 85-169). Since typical proteins have only one site for particular activity, the existence of multiple active sites is surprising. Moreover, it is also surprising that the activity of each fragment is greater than that of the sequence (2-215), which consists of nearly the full length. Meanwhile, although the RAGE-binding domain is the amino acid sequence from positions 150 to 183, the amino acid sequence of positions 89 to 169 also has migration-promoting activity on human bone marrow mesenchymal stem cells, suggesting that the migration-promoting activity may not require RAGE. Regarding human HMGB1 fragments (89-185, 89-195, 89-205, and 89-215), the fragments lacking the C-terminal acidic tail showed stronger activity, as with the case of mouse-derived cells. This finding suggests that the C terminus also suppresses the migration-promoting activity on human bone marrow mesenchymal stem cells, and therefore more active HMGB1 fragments may be produced by shortening or eliminating the C-terminal acidic tail.

Altered migration-promoting activity of fusion fragments in which human HMGB1 acidic tail fragment 186-215, 186-205, or 186-195 is added to human HMGB1 fragment 2-84

Methods

Fusion cDNAs were constructed such that human HMGB1 fragment 186-215, 186-205, or 186-195 was added to the C terminus of human HMGB1 fragment 2-84. As described above, expression vectors were designed such that, in a fragment expressed in *E. coli*, the N terminal methionine (M) of human HMGB1 was deleted and instead MKHHHHHHENLYFQ (SEQ ID NO: 11) was added to its N terminus. HHHHHH (SEQ ID NO: 12) is a tag (6×His tag) for use in purification of an expressed protein or peptide using a nickel column. ENLYFQG (SEQ ID NO: 13) is a sequence that is recognized by TEV protease (FIG. 18A). Furthermore, vectors were constructed in which the cDNA described above was inserted downstream of T7 promoter and lac operator, the drug resistance gene was a kanamycin resistance gene, and the replication origins were pBR322 ori and f1 ori, A human HMGB1 protein or peptide that starts from the second amino acid can be prepared by cleaving with TEV protease a protein or peptide obtained using the above-described expression vector.

BL-21(DE3) was transformed with the constructed plasmids. The bacteria were cultured in LB containing kanamycin while shaking at 37° C. overnight, and 5 ml of bacterial suspensions were transferred into 100 ml of LB. The bacteria were cultured while shaking at 140 rpm and 37° C. The turbidity was measured with a turbidimeter, and, when OD reached 0.5 to 0.7, isopropyl-β-D-thiogalactopyranoside (IPTG) was added at a final concentration of 1 mM. After overnight shaking culture at 15° C., the bacterial cells were harvested.

Purification of Respective HMGB1 fragments (2+84+186-215, 2-84+186-205, and 2-84+186-195)

Equilibration buffer (PBS(137 mM NaCl, 8.1 mM $Na_2HPO_4$, 2.68 mM KCl, 1.47 mM $KH_2PO_4$), 10 mM imidazole; pH7.4) was added to the collected bacterial cells so that the final concentration was 5 μg/ml. The bacterial cells were sonicated and centrifuged at 15,000 rpm and 4° C. for 60 minutes. The supernatant was collected, and the remaining supernatant was sterilized by filtering through a 0.45-μm filter. The protein of interest was purified by column chromatography using BioLogic DuoFlow (Bio-Rad).

Then, ion-exchange purification was performed using 5 ml of HiTrap™ Q HP (GE Healthcare) for 2-84+186-215, 2-84+186-205, and 2-84+186-195. PBS (pH 7.4) was used as Buffer A, while 7×PBS (pH 7.4) was used as Buffer B. After the column was equilibrated with an appropriate amount of Buffer A, a solution of affinity purified protein was loaded onto it. Washing and purification were performed with the program described below. The program used is as follows:

Isocratic Flow (Buffer A: 100%, Buffer B: 0%, 50 ml, 4 ml/min)

Linear Gradient (Buffer A: 100%→0%, Buffer B: 0%→100%, 50 ml, 4 ml/min)

Isocratic Flow (Buffer A: 0%, Buffer B: 100%, 5 ml, 4 ml/min)

Fraction Collection (3 ml each; 50 to 105 ml)

Each fraction was examined by SDS-PAGE followed by protein staining of the gel to confirm purified proteins.

Each fragment was subjected to Western blotting using an antibody that recognizes human HMGB1 to confirm whether it is the fragment of interest.

Migration assay of HMGB1 fragment (2-84), and fusion HMGB1 fragments (2-84+186-215, 2-84+186-205, and 2-84+186-195) using MSC-1

Fragments prepared by the methods described above were used to perform migration assay using bone marrow mesenchymal stem cell line MSC-1. The migration assay was performed in the same manner as described above.

Results

Figure 21C:
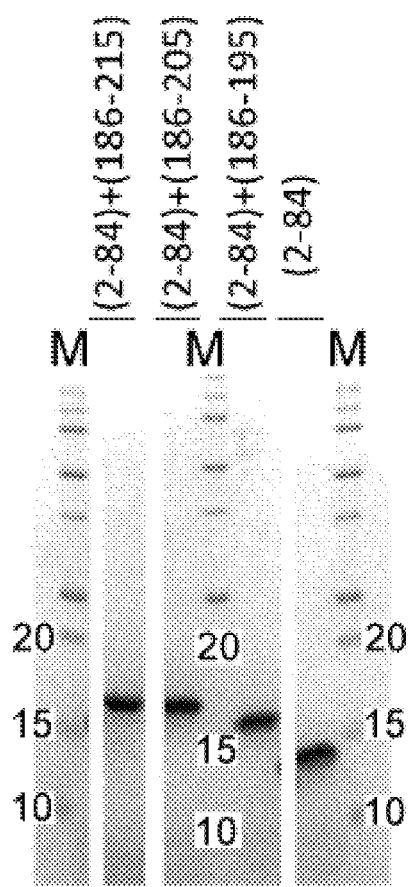
FIG. 21C shows a CBB protein staining of a gel on which fusion fragments (2-84)+(186-215), (2-84)+(186-205), and (2-84)+(186-195), which were obtained by adding to the purified human HMGB1 fragment (2-84) a fragment of the acidic tail of human HMGB1 ((186-215), (186-205), or (186-195)), were electrophoresed by SDS-PAGE. Each purified fragment was confirmed.
Figure 21D:
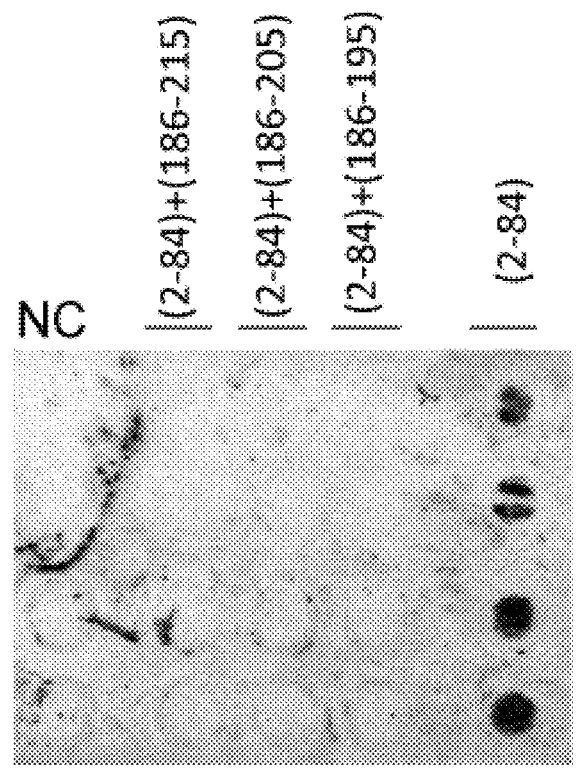
FIG. 21D is a diagram in which migration-promoting activity on MSC-1 was examined using the purified fragments. Migration-promoting activity was not shown for any of the fusion fragments obtained by adding an acidic tail sequence to the 2-84 fragment. Meanwhile, the 2-84 fragment itself showed migration-promoting activity.
Figure 22:
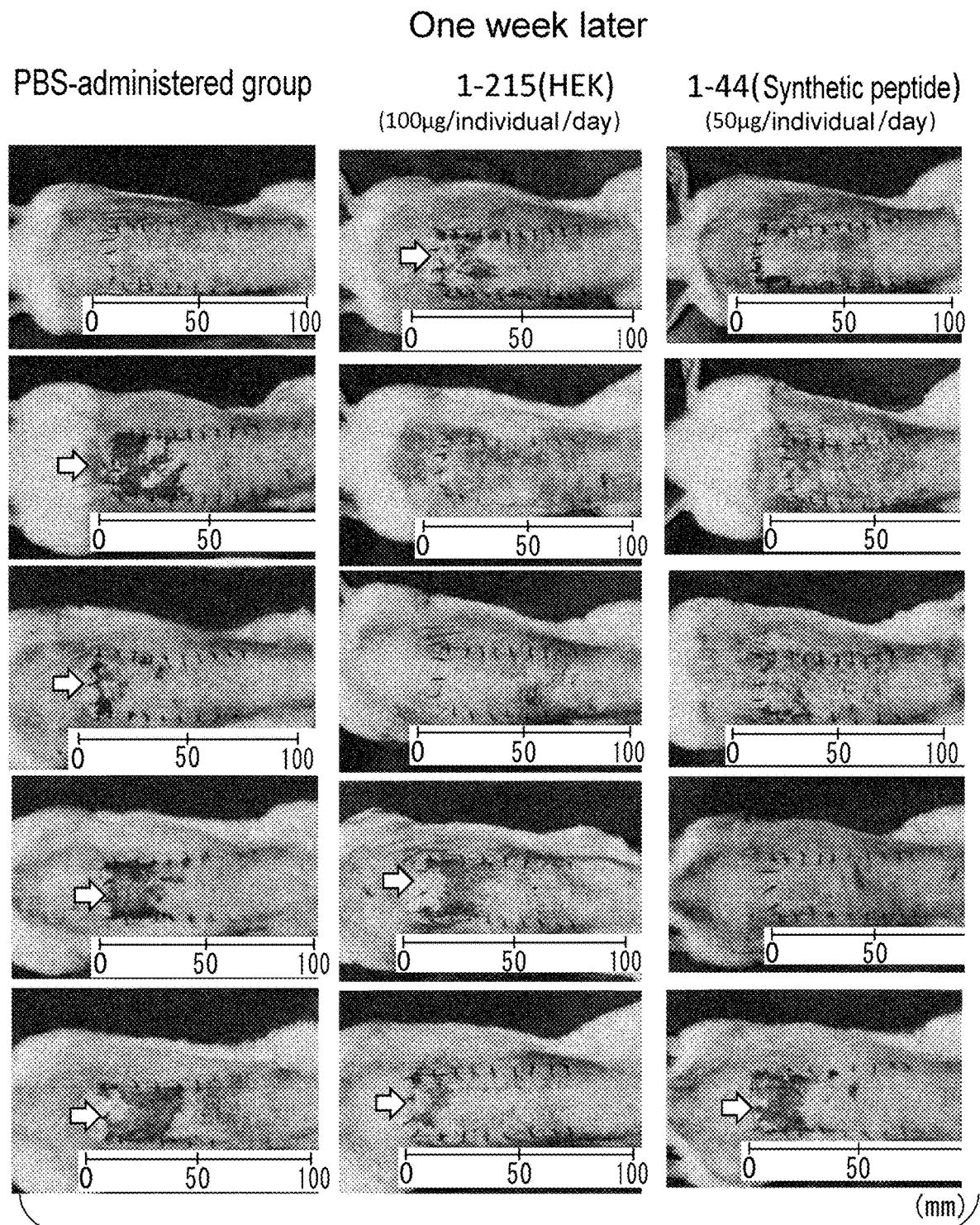
FIG. 22 is a set of photographs showing the skin flap made on the back of a rat, which were taken one week later. PBS is the negative control group. Groups administered with HMGB1 containing the full length produced by HEK293 cells (1-215 (HEK)) and administered with a synthetic peptide of amino acids of positions 1 to 44 (1-44 (synthetic peptide)) were compared. The arrows show necrosed skin tissue.
Figure 23:
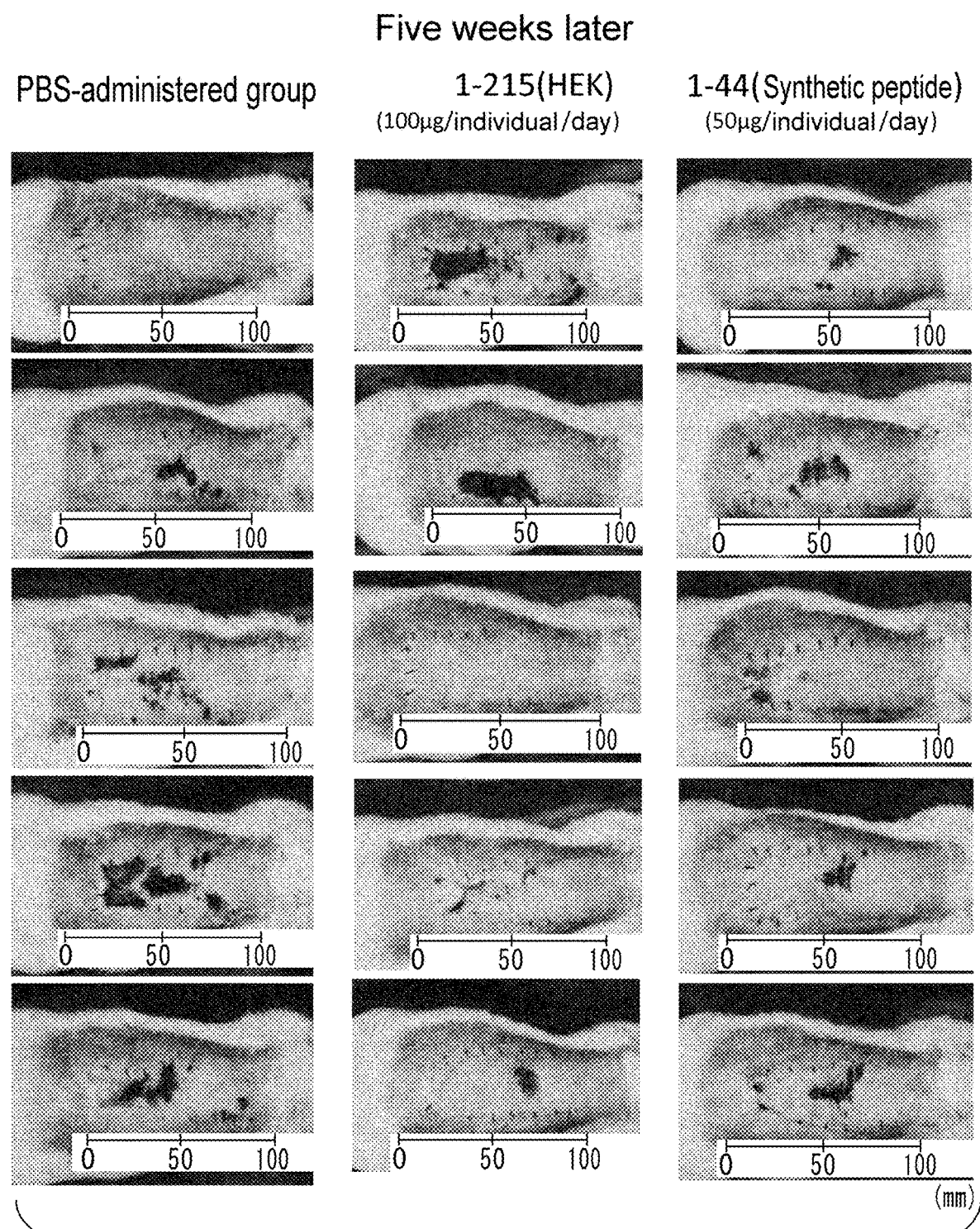
FIG. 23 is a set of photographs showing the skin flap made on the back of a rat, which were taken five weeks later. PBS is the negative control group. Groups administered with HMGB1 containing the full length produced in HEK293 cells (1-215 (HEK)) and administered with a synthetic peptide of amino acids of positions 1 to 44 (1-44 (synthetic peptide)) were compared. The red-colored sections are where skin ulcers were formed.

Fragment 2-84 exhibited migration-promoting activity, while none of the fusion human HMGB1 fragments with 10 amino acids, 20 amino acids, or 30 amino acids of the acidic tail sequence showed the activity (FIG. 21C).

Discussion

As shown in the above-mentioned Examples, human HMGB1 fragment 89-215 has only extremely weak migration-promoting activity on mesenchymal stem cells; however, successive truncation of the C-terminal acidic tail increases the migration-promoting activity. The findings described above and the present Example demonstrate that the acidic tail has the function to reduce the migration-promoting activity of fragments 2-84 and 89-185. Fragment 2-84 has multiple core regions with migration-promoting activity. Since fusion of fragment 2-84 with fragment 186-215 resulted in almost complete loss of the migration-promoting activity, it is presumed that the suppression acts on all the core regions in 2-84. It is a surprising discovery that a single molecule of HMGB1 contains at least three or more core sequences with migration-promoting activity on bone marrow mesenchymal stem cells. Another very surprising discovery is that the C-terminal acidic tail of only 30 amino acids almost completely suppresses the migration-promoting activity of at least two core sequences in the N-terminal fragment 2-84 of HMGB1 and suppresses the migration-promoting activity of the core sequence in fragment 85-185 as well, resulting in a decrease in the overall migration-promoting activity of HMGB1. HMGB1 fragment 1-85 is believed to have an anti-inflammatory effect against inflammation induced by LPS (lipopolysaccharide) and such. Wei Gong et al. have reported that a fragment of 1-85 fused with fragment 186-215 reduces the rate of death caused by LPS administration more than fragment 1-85 (Journal of Biomedicine and Biotechnology Volume 2010, Article ID 915234, doi: 10.1155/2010/915234). The article of Wei Gong et al. suggests that the acidic tail is required to increase the anti-inflammatory effect of 1-85. On the other hand, the present invention demonstrated that the acidic tail rather inhibited the migration of bone marrow mesenchymal stem cells. In view of the present invention, it is expected that shortening or complete elimination of the acidic tail can achieve more improvement of therapeutic effects on diseases on which administration of bone marrow mesenchymal stem cells has therapeutic effects.

Example 18

Methods

Experimental animals used were SD rats (male, eight weeks old). After sufficiently deep anesthesia by isoflurane inhalation, a rectangular skin incision of 3 cm width×7 cm length was made on the back. The cephalic side was left uncut, and the skin was thoroughly detached from the subcutaneous tissues. The three incised sides were sutured to the surrounding skin using #4 silk suture, and protected with Tegaderm (3M) to prevent bacterial infection.

The full-length mouse HMGB1 (100 μg/administration/day) produced in HEK293 and chemically synthesized HMGB1 peptide (amino acids 1 to 44; 50 μg/administration/day) were diluted to 200 μl with phosphate buffer and administered to rats via the caudal vein. The first administration was performed 6 hours after the surgery, and then the agents were administered every 24 hours a total of five times. Phosphate-buffered physiological saline was administered as a negative control. Tegaderm was removed after one week, and the wound region was observed weekly to measure the areas of necrosis and ulceration.

Results

Figure 24:
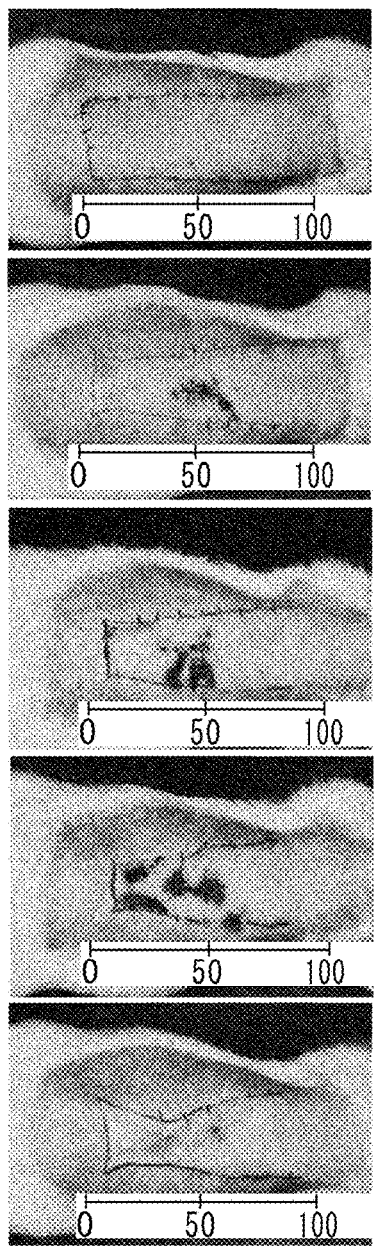
FIG. 24 is a set of photographs showing the skin flap made on the back of a rat, which were taken seven weeks later. PBS is the negative control group. Groups administered with HMGB1 containing the full length produced in HEK293 cells (1-215 (HEK)) and administered with a synthetic peptide of amino acids of positions 1 to 44 (1-44 (synthetic peptide)) were compared.
Figure 24:
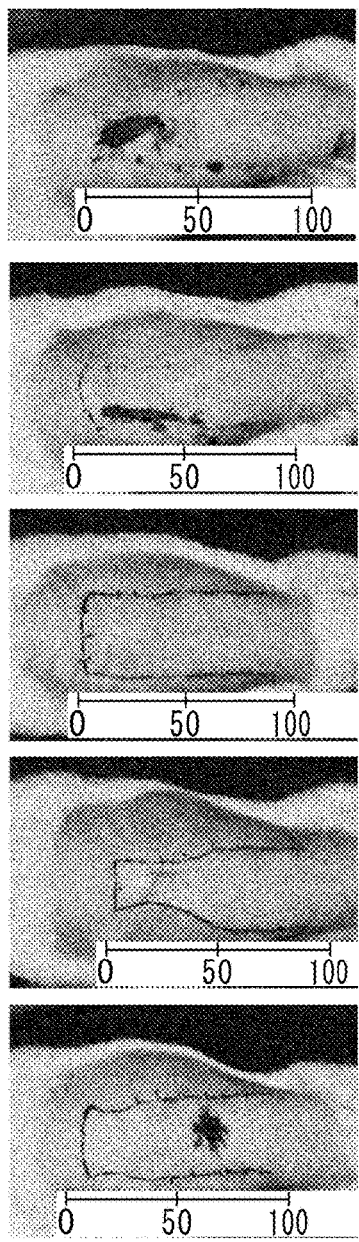
Figure 24:
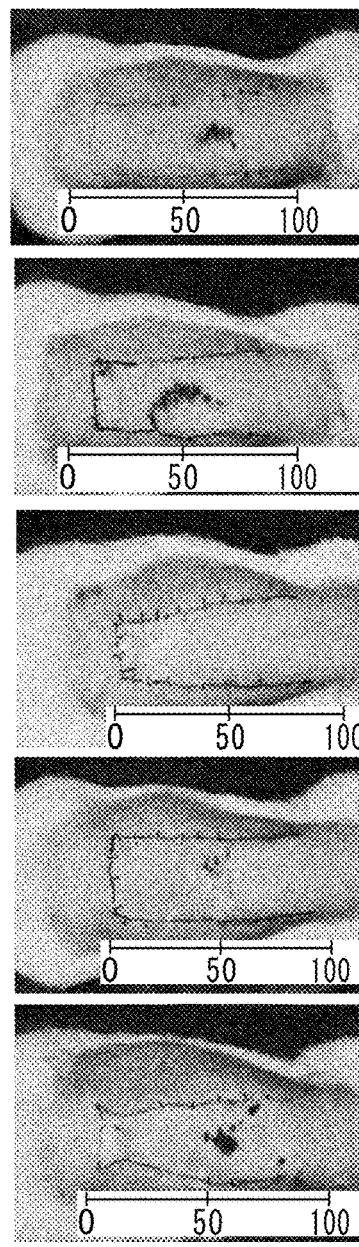
Figure 25:
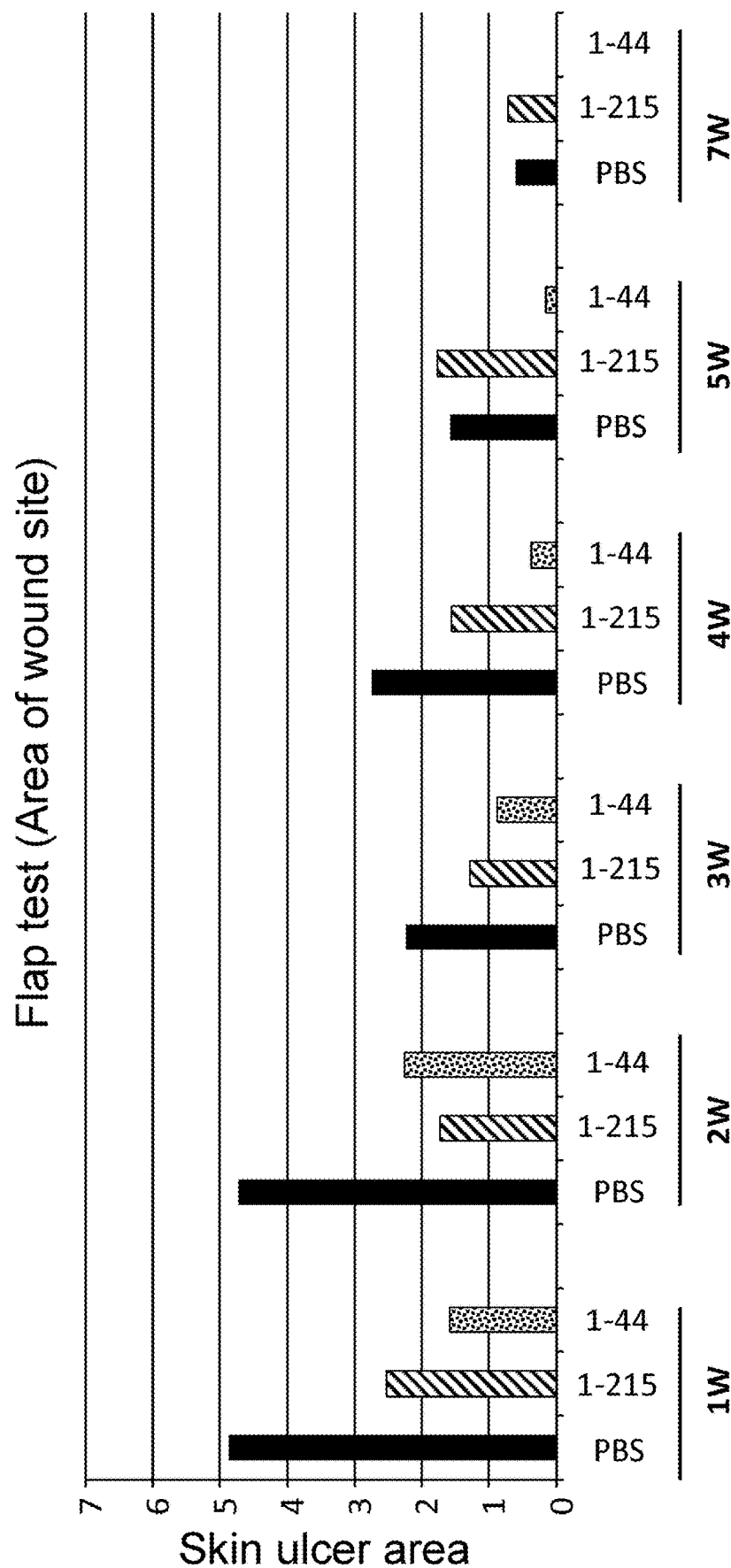
FIG. 25 is a graph showing the quantified area of wound section (necrosed section) that developed in the skin flap made on the rat back. An effect of shrinking the wound section was confirmed in the groups administered with HMGB1 containing the full length produced in HEK293 cells (1-215 (HEK)) and administered with a synthetic peptide of amino acids of positions 1 to 44 (1-44 (synthetic peptide)) in comparison with the negative control group one to three weeks after the skin flap was made. After four weeks and later, a further shrinking effect was observed in 1-44 (synthetic peptide) in comparison with the other two groups.

One week after surgery, skin necrosis developed in four of five rats of the negative control group. In the group administered with the full-length HMGB1, skin necrosis developed in three of five rats. In the HMGB1 peptide (amino acids 1-44) group, skin necrosis developed in one of five rats. Seven weeks after surgery, while severe skin contracture occurred in four of five rats of the negative control group, three of five rats of the full-length HMGB1-administered group and two of five rats of the HMGB1 peptide (amino acids 1-44) group showed such contracture (FIG. 24).

Discussion

The shrinking effect on necrotizing tissues after one week was observed in the group administered with the full-length HMGB1 produced in HEK293 and in the HMGB1 peptide (amino acids 1-44) administration group. The shrinking effect was stronger in the HMGB1 peptide (amino acids 1-44) group. After one, two, and three weeks, the wound area was reduced to a half of the area of the negative control group. After the third week, the wound area in the HMGB1 peptide (amino acids 1-44) administration group was further reduced as compared to the other two groups. During the 7-week healing process, there was also a tendency that the wound area was smaller in the HMGB1 peptide (amino acids 1-44) group. The contracture at the wound site after seven weeks was also the mildest in the HMGB1 peptide (amino acids 1-44) group. Bone marrow mesenchymal stem cells are known to enhance the growth of skin cells under low-oxygen conditions. It is presumed that bone marrow mesenchymal stem cells recruited by HMGB1 enhanced the wound healing by suppressing the expansion of skin necrosis due to undernutrition and hypoxia caused by skin flap production. It is suggested that such effects are advantageous not only in suppressing expansion of damage caused by skin ischemia, injury, and surgery but also in the cosmetic aspect after healing.

Example 19

Methods

Experimental animals used were 15 SD rats (male, eight weeks old) per group. After sufficient anesthesia by isoflurane inhalation, a rectangular skin incision of 3 cm width×7 cm length was made on the back. The cephalic side was left uncut, and the skin was thoroughly detached from the subcutaneous tissues. The incised three sides were sutured to the surrounding skin using #4 silk suture, and protected with Tegaderm (3M) to prevent bacterial infection.

Chemically synthesized HMGB1 peptide (amino acids 1-44; 50 μg/administration/day) or HMGB1 peptide (amino acids 17-25; 50 μg/administration/day) was diluted to 200 μl with phosphate buffer and administered to the rats with experimental wound. The first administration was performed 6 hours after the surgery, and then the agents were administered every 24 hours a total of five times. Phosphate-buffered physiological saline was administered as a negative control. Tegaderm was removed after one week, and the wound was observed two weeks after the wound production. Uncured areas (ulceration and necrosis) were measured.

Results

Figure 26:
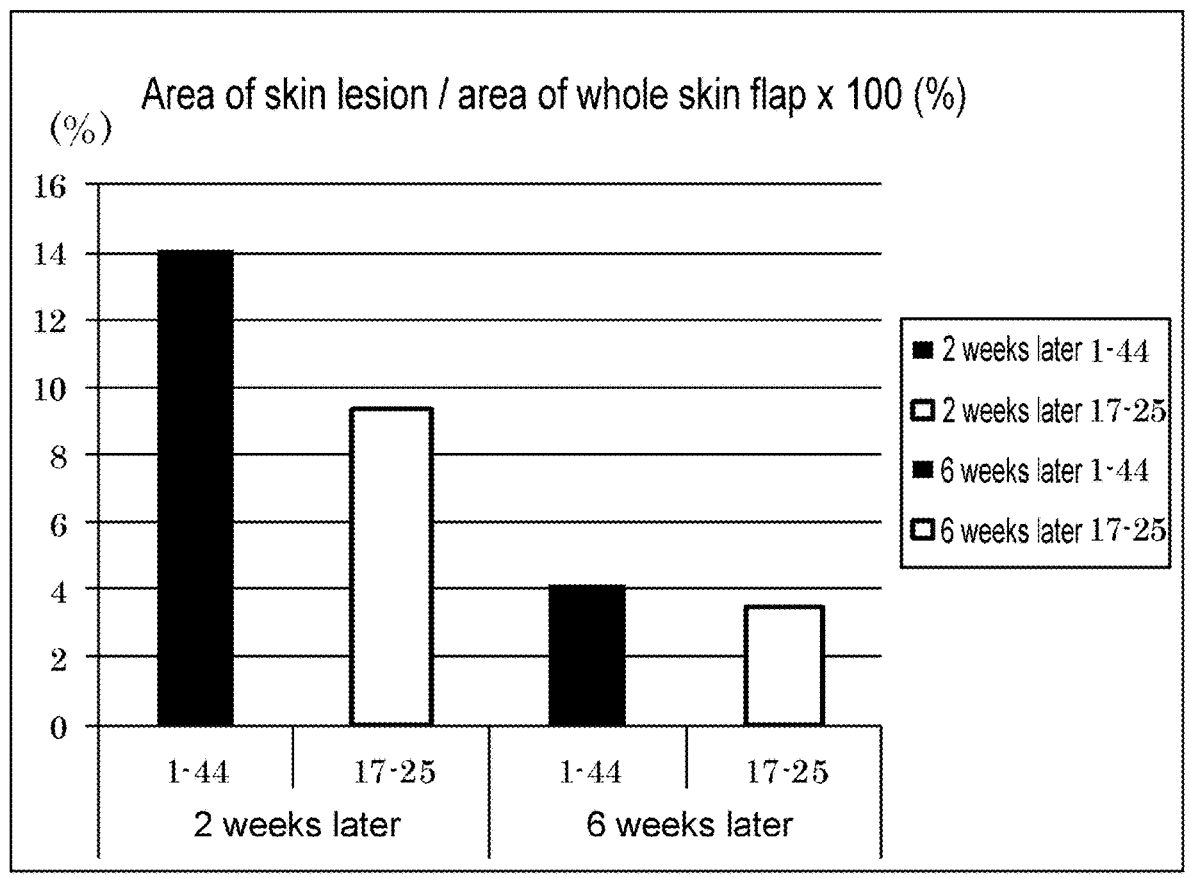
FIG. 26 is chemically synthesized HMGB1 peptides (1-44) and (17-25) were administered to the caudal vein of a rat with produced skin lesion. The figure shows the respective percentages of the area of the skin lesion site relative to the entire area of the skin flap two weeks and six weeks after the skin flap was made.

The ratio (%) of the uncured area relative to the area of the whole skin flap after two weeks of the skin flap production was calculated. The uncured area accounted for 14.1% on average in the HMGB1 peptide (amino acids 1-44) group and 9.1% on average in the HMGB1 peptide (amino acids 17 to 25, 50 μg/administration/day) group. In addition, the ratio (%) of the uncured area relative to the area of the whole skin flap after six weeks of the skin flap production was 4.1% on average in the HMGB1 peptide (amino acids 1-44) group and 3.5% on average in the HMGB1 peptide (amino acids 17-25; 50 μg/administration/day) group (FIG. 26).

Discussion

In the test using the skin damage model in Example 19, there was a tendency that the wound area during the healing process from weeks 1 to 7 after damage was smaller in the group administered with chemically synthesized HMGB1 peptide (amino acids 1-44) as compared to the group administered with the full-length HMGB1 produced in HEK293. Furthermore, the test of the present Example demonstrated that the skin damage-improving effect observed in the chemically-synthesized HMGB1 peptide (amino acids 17-25) group was comparable to or greater than that seen in the HMGB1 peptide (amino acids 1-44, 50 μg/administration/day) group. There are multiple regions (core sequences) having the activity of recruiting bone marrow mesenchymal stem cells in vitro, Of these, the shortest sequence known at present is the sequence consisting of 9 amino acids from position 17 to 25. The other core sequences with the activity of recruiting mesenchymal stem cells require 30 amino acids or 85 amino acids in length. The experiment of this Example demonstrated that the group administered with the HMGB1 peptide consisting of only 9 amino acids (amino acids 17-25) showed improvement of the skin damage not only in vitro but also in vivo. Peptides containing the 9 amino acids as the core domain are expected to be much more stably produced at a lower cost as compared to protein preparations produced from eukaryote-derived cultured cells such as HEK293.

INDUSTRIAL APPLICABILITY

The present invention provides peptides retaining activity of recruiting PDGFRα-positive cells, whose molecular weights are, for example, one tenth or less as compared to the full-length HMGB1 protein consisting of about 200 amino acids. Such peptides can be produced by chemical synthesis methods using peptide synthesizers, as well as production methods using E. coli or eukaryote-derived cultured cells. Thus, when the peptides are produced as pharmaceuticals, one can expect purity improvement, stable production, and cost reduction.

Furthermore, when the recombinant peptides were produced in E. coli or cultured cells, they showed improved activity that was about twice or about six times that of the full-length HMGB1 when compared per mole or per mass, respectively. Thus, when the peptides are clinically used as pharmaceuticals, it is possible to use reduced dosages. This leads to cost reduction and prevention of side effects.

In addition, the full-length HMGB1 is known to have the binding activity with lipopolysaccharide (LPS), which is an endotoxin. Furthermore, there is a report that HMGB1 fragments of amino acids 1 to 79 or amino acids 88 to 162 of HMGB1 lack the LPS-binding activity (Youn et al., J Immunol 2008, 180; 5067-5074).

When pharmaceuticals are contaminated with even a trace amount of LPS, they cause fever and such, often resulting in severe adverse effects. Therefore, there are strict regulations against contamination of pharmaceuticals with LPS. Since HMGB1 has affinity for LPS, it is difficult to completely remove contaminating LPS from pharmaceuticals. However, since the conversion into peptides results in reduction of the affinity for LPS, it is expected that contamination of pharmaceuticals with LPS can be reduced. Thus, by using peptides consisting of a portion identified in the present invention as recruiting PDGFRα-positive cells, it is possible to develop much safer pharmaceuticals.

By administering a peptide of the present invention to a tissue in need of regeneration or an adjacent tissue thereof, regeneration of the tissue can be induced or promoted. Moreover, by administering a peptide of the present invention to a tissue other than a tissue in need of regeneration by intravenous administration and such, regeneration of the tissue in need of regeneration can be induced or promoted. For example, in the treatment of a disease of deep-seated organ, such as cerebral infarction, it is difficult to administer a therapeutic agent directly to a damaged site (brain). On the other hand, in the present invention, such treatment can be carried out by intravenous administration, which is widely used in general medical practice. It is therefore possible to administer a therapeutic agent at any concentration and frequency in a safe and simple manner. This is a superior effect as compared to conventional therapeutic methods.

Meanwhile, a recently developed bone marrow cell-based method that is known to be effective in treating cerebral infarction involves the collection of cells from patient's bone marrow and re-administration of the cells into the bloodstream. This method is inevitably associated with severe invasion because bone marrow cells need to be aspirated with a large-bore needle inserted into the bone marrow, which is located deep inside the body. In contrast, the present invention allows bone marrow cells to be recruited directly to the bloodstream by intravenous administration of an agent, and therefore does not involve severe invasion even when the agent is frequently administered to cerebral infarction patients.

Bone marrow-derived pluripotent stem cells have the potential ability to differentiate into various types of cells such as mesenchymal cells, epithelial cells, and nerve cells. After migrating to a damaged site, they may differentiate depending on a niche environment surrounding the damaged site, and then induce tissue repair. In regenerative medicine and cell therapy, bone marrow pluripotent stem cells, which are rare cells, are expanded by ex vivo culture before use in the treatment. However, this requires adequate safety control because, unlike conventional pharmaceutical agents, there is a risk of deterioration of cells (canceration and contamination with bacteria, viruses, etc.) which may be caused during the culturing process. On the other hand, the present invention is highly safe because the cells are not removed from the body for artificial manipulation.

The invention claimed is:

1. A peptide selected from the group consisting of:
A) a peptide that consists of a portion of an HMGB1 protein of the amino acid sequence of SEQ ID NO: 1 and has an activity of stimulating migration of a cell, wherein the peptide consists of the whole or part of the amino acid sequence of positions 1 to 52 in the amino acid sequence of SEQ ID NO: 1, and comprises any of the amino acid sequences below:

(1) the amino acid sequence of position 2 to position 25 in the amino acid sequence of SEQ ID NO: 1;
(2) the amino acid sequence of position 11 to position 34 in the amino acid sequence of SEQ ID NO:1; and
(3) the amino acid sequence of position 17 to position 44 in the amino acid sequence of SEQ ID NO:1;

B) a peptide that consists of a portion of an HMGB1 protein of the amino acid sequence of SEQ ID NO: 1 and has an activity of stimulating migration of a cell, wherein the peptide consists of the whole or part of the amino acid sequence of positions 1 to 25 or positions 17 to 44 in the amino acid sequence of SEQ ID NO: 1, and comprises the amino acid sequence of position 17 to position 25 in the amino acid sequence of SEQ ID NO: 1;

C) a peptide that consists of a portion of an HMGB1 protein of the amino acid sequence of SEQ ID NO: 1 and has an activity of stimulating migration of a cell, wherein the peptide consists of the whole or part of the amino acid sequence of positions 1 to 205 in the amino acid sequence of SEQ ID NO: 1, and comprises the amino acid sequence of position 89 to position 195 in the amino acid sequence of SEQ ID NO: 1;

D) a peptide that consists of a portion of an HMGB1 protein of the amino acid sequence of SEQ ID NO: 1 and has an activity of stimulating migration of a cell, wherein the peptide consists of the whole or part of the amino acid sequence of positions 45 to 215 in the amino acid sequence of SEQ ID NO: 1, and comprises any of the amino acid sequences below:
(1) the amino acid sequence of position 85 to position 169 in the amino acid sequence of SEQ ID NO: 1;
(2) the amino acid sequence of position 89 to position 185 in the amino acid sequence of SEQ ID NO: 1; and
(3) the amino acid sequence of position 93 to position 215 in the amino acid sequence of SEQ ID NO: 1; and E) a peptide that consists of any of the amino acid sequences below:
(1) the amino acid sequence of position 1 to position 44 in the amino acid sequence of SEQ ID NO: 1;
(2) the amino acid sequence of position 1 to position 70 in the amino acid sequence of SEQ ID NO: 1;
(3) the amino acid sequence of position 1 to position 84 in the amino acid sequence of SEQ ID NO:1;
(4) the amino acid sequence of position 1 to position 170 in the amino acid sequence of SEQ ID NO: 1;
(5) the amino acid sequence of position 1 to position 185 in the amino acid sequence of SEQ ID NO: 1;
(6) the amino acid sequence of position 1 to position 195 in the amino acid sequence of SEQ ID NO: 1;
(7) the amino acid sequence of position 2 to position 44 in the amino acid sequence of SEQ ID NO: 1;
(8) the amino acid sequence of position 2 to position 70 in the amino acid sequence of SEQ ID NO: 1,
(9) the amino acid sequence of position 2 to position 84 in the amino acid sequence of SEQ ID NO: 1;
(10) the amino acid sequence of position 2 to position 170 in the amino acid sequence of SEQ ID NO: 1;
(11) the amino acid sequence of position 2 to position 185 in the amino acid sequence of SEQ ID NO: 1;
(12) the amino acid sequence of position 2 to position 195 in the amino acid sequence of SEQ ID NO: 1;
(13) the amino acid sequence of position 17 to position 25 in the amino acid sequence of SEQ ID NO: 1;
(14) the amino acid sequence of position 45 to position 84 in the amino acid sequence of SEQ ID NO: 1;
(15) the amino acid sequence of position 85 to position 169 in the amino acid sequence of SEQ ID NO: 1;
(16) the amino acid sequence of position 89 to position 185 in the amino acid sequence of SEQ ID NO: 1;
(17) the amino acid sequence of position 89 to position 195 in the amino acid sequence of SEQ ID NO: 1; and
(18) the amino acid sequence of position 93 to position 215 in the amino acid sequence of SEQ ID NO: 1.

2. The peptide of claim 1, that consists of a portion of an HMGB1 protein of the amino acid sequence of SEQ ID NO: 1 and has an activity of stimulating migration of a cell, wherein the peptide consists of the whole or part of the amino acid sequence of positions 1 to 52 in the amino acid sequence of SEQ ID NO: 1, and comprises any of the amino acid sequences below:
(1) the amino acid sequence of position 2 to position 25 in the amino acid sequence of SEQ ID NO: 1;
(2) the amino acid sequence of position 11 to position 34 in the amino acid sequence of SEQ ID NO:1; and
(3) the amino acid sequence of position 17 to position 44 in the amino acid sequence of SEQ ID NO:1.

3. The peptide of claim 1, that consists of a portion of an HMGB1 protein of the amino acid sequence of SEQ ID NO: 1 and has an activity of stimulating migration of a cell, wherein the peptide consists of the whole or part of the amino acid sequence of positions 1 to 25 or positions 17 to 44 in the amino acid sequence of SEQ ID NO: 1, and comprises the amino acid sequence of position 17 to position 25 in the amino acid sequence of SEQ ID NO: 1.

4. The peptide of claim 1, that consists of a portion of an HMGB1 protein of the amino acid sequence of SEQ ID NO: 1 and has an activity of stimulating migration of a cell, wherein the peptide consists of the whole or part of the amino acid sequence of positions 1 to 205 in the amino acid sequence of SEQ ID NO: 1, and comprises the amino acid sequence of position 89 to position 195 in the amino acid sequence of SEQ ID NO: 1.

5. The peptide of claim 1, that consists of a portion of an HMGB1 protein of the amino acid sequence of SEQ ID NO: 1 and has an activity of stimulating migration of a cell, wherein the peptide consists of the whole or part of the amino acid sequence of positions 45 to 215 in the amino acid sequence of SEQ ID NO: 1, and comprises any of the amino acid sequences below:
(1) the amino acid sequence of position 85 to position 169 in the amino acid sequence of SEQ ID NO: 1;
(2) the amino acid sequence of position 89 to position 185 in the amino acid sequence of SEQ ID NO: 1; and
(3) the amino acid sequence of position 93 to position 215 in the amino acid sequence of SEQ ID NO: 1.

6. The peptide according to claim 1, that consists of any of the amino acid sequences below:
(1) the amino acid sequence of position 1 to position 44 in the amino acid sequence of SEQ ID NO: 1;
(2) the amino acid sequence of position 1 to position 70 in the amino acid sequence of SEQ ID NO: 1,
(3) the amino acid sequence of position 1 to position 84 in the amino acid sequence of SEQ ID NO:1;
(4) the amino acid sequence of position 1 to position 170 in the amino acid sequence of SEQ ID NO: 1;
(5) the amino acid sequence of position 1 to position 185 in the amino acid sequence of SEQ ID NO: 1;
(6) the amino acid sequence of position 1 to position 195 in the amino acid sequence of SEQ ID NO: 1;
(7) the amino acid sequence of position 2 to position 44 in the amino acid sequence of SEQ ID NO: 1;
(8) the amino acid sequence of position 2 to position 70 in the amino acid sequence of SEQ ID NO: 1;
(9) the amino acid sequence of position 2 to position 84 in the amino acid sequence of SEQ ID NO: 1;
(10) the amino acid sequence of position 2 to position 170 in the amino acid sequence of SEQ ID NO: 1;
(11) the amino acid sequence of position 2 to position 185 in the amino acid sequence of SEQ ID NO: 1;
(12) the amino acid sequence of position 2 to position 195 in the amino acid sequence of SEQ ID NO: 1;

(13) the amino acid sequence of position 17 to position 25 in the amino acid sequence of SEQ ID NO: 1;
(14) the amino acid sequence of position 45 to position 84 in the amino acid sequence of SEQ ID NO: 1;
(15) the amino acid sequence of position 85 to position 169 in the amino acid sequence of SEQ ID NO: 1;
(16) the amino acid sequence of position 89 to position 185 in the amino acid sequence of SEQ ID NO: 1;
(17) the amino acid sequence of position 89 to position 195 in the amino acid sequence of SEQ ID NO: 1; and
(18) the amino acid sequence of position 93 to position 215 in the amino acid sequence of SEQ ID NO: 1.

7. The peptide of claim 1, which is a synthetic peptide.

8. The peptide of claim 1, which is a peptide produced using a cell.

9. The peptide of claim 1, which is a peptide to which a tag is added.

10. The peptide of claim 1, which is a peptide to which a tag-derived peptide fragment is added.

11. A composition comprising the peptide of claim 1 and a pharmaceutically acceptable carrier or additive.

12. The composition of claim 11, wherein the pharmaceutically acceptable carrier or additive is selected from the group consisting of surfactant, excipient, colorant, perfume, preservative, stabilizer, buffer, suspending agent, isotonizing agent, binder, disintegrant, lubricant, flow promoter, and flavoring agent.

13. The composition of claim 11, wherein the pharmaceutically acceptable carrier or additive is selected from the group consisting of light anhydrous silicic acid, lactose, crystalline cellulose, mannitol, starch, carmellose calcium, carmellose sodium, hydroxypropylcellulose, hydroxypropylmethylcellulose, polyvinylacetaldiethylamino acetate, polyvinylpyrrolidone, gelatin, medium-chain fatty acid triglyceride, polyoxyethylene hydrogenated castor oil 60, white sugar, carboxymethyl cellulose, corn starch, and inorganic salt.

* * * * *

SEQUENCE LISTING

```
<160> NUMBER OF SEQ ID NOS: 14

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
```

```
                65                  70                  75                  80
Pro Lys Gly Glu Thr Lys Lys Phe Lys Asp Pro Asn Ala Pro Lys
                    85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Asp Glu
                195                 200                 205

Glu Glu Asp Asp Asp Asp Glu
        210                 215

<210> SEQ ID NO 2
<211> LENGTH: 648
<212> TYPE: DNA
<213> ORGANISM: Homo sapiens

<400> SEQUENCE: 2
atgggcaaag gagatcctaa gaagccgaga ggcaaaatgt catcatatgc atttttgtg      60 caaacttgtc gggaggagca taagaagaag cacccagatg cttcagtcaa cttctcagag    120
ttttctaaga agtgctcaga gaggtggaag accatgtctg ctaaagagaa aggaaaattt    180
gaagatatgg caaaagcgga caaggcccgt tatgaaagag aaatgaaaac ctatatccct    240
cccaaagggg agacaaaaaa gaagttcaag gatcccaatg cacccaagag gcctccttcg    300
gccttcttcc tcttctgctc tgagtatcgc ccaaaaatca aggagaacat cctggcctg    360 tccattggtg atgttgcgaa gaaactggga gagatgtgga taacactgc tgcagatgac    420 aagcagcctt atgaaaagaa ggctgcgaag ctgaaggaaa atacgaaaa ggatattgct    480 gcatatcgag ctaaaggaaa gcctgatgca gcaaaaaagg gagttgtcaa ggctgaaaaa    540
agcaagaaaa agaaggaaga ggaggaagat gaggaagatg aagaggatga ggaggaggag    600
gaagatgaag aagatgaaga tgaagaagaa gatgatgatg atgaataa                 648

<210> SEQ ID NO 3
<211> LENGTH: 215
<212> TYPE: PRT
<213> ORGANISM: Mus musculus

<400> SEQUENCE: 3

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60
```

```
Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Asp Asp Glu Glu
                180                 185                 190

Asp Glu Glu Asp Glu Glu Glu Glu Glu Glu Asp Glu Asp
                195                 200                 205

Glu Glu Asp Asp Asp Asp Glu
        210                 215
```

<210> SEQ ID NO 4
<211> LENGTH: 648
<212> TYPE: DNA
<213> ORGANISM: Mus musculus

<400> SEQUENCE: 4

```
atgggcaaag gagatcctaa aaagccgaga ggcaaaatgt cctcatatgc attctttgtg    60
caaacttgcc gggaggagca caagaagaag caccccggatg cttctgtcaa cttctcagag   120
ttctccaaga gtgctcaga gaggtggaag accatgtctg ctaaagaaaa ggggaaattt     180
gaagatatgg caaaggctga caaggctcgt tatgaaagag aaatgaaaac ctacatcccc    240
cccaaagggg agaccaaaaa gaagttcaag accccaatg cacccaagag gcctccttcg    300
gccttcttct tgttctgttc tgagtaccgc cccaaaatca aggcgagca tcctggctta    360
tccattggtg atgttgcaaa gaaactagga gagatgtgga caacactgc agcagatgac    420
aagcagccct atgagaagaa agctgccaag ctgaaggaga gtatgagaa ggatattgct    480
gcctacagag ctaaggaaa acctgatgca gcgaaaaagg gggtggtcaa ggctgaaaag    540
agcaagaaaa agaaggaaga ggaagatgat gaggaggatg aagaggatga ggaagaggag    600
gaagaagagg aagacgaaga tgaagaagaa gatgatgatg atgaataa                648
```

<210> SEQ ID NO 5
<211> LENGTH: 215
<212> TYPE: PRT
<213> ORGANISM: Rattus norvegicus

<400> SEQUENCE: 5

```
Met Gly Lys Gly Asp Pro Lys Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Cys Ser Glu Arg
            35                  40                  45

Trp Lys Thr Met Ser Ala Lys Glu Lys Gly Lys Phe Glu Asp Met Ala
 50                  55                  60
```

```
Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
             85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
        210                 215

<210> SEQ ID NO 6
<211> LENGTH: 648
<212> TYPE: DNA
<213> ORGANISM: Rattus norvegicus

<400> SEQUENCE: 6
atgggcaaag agatcctaa gaagccgaga ggcaaaatgt cctcatatgc attctttgtg      60
caaacctgcc gggaggagca agaagaag caccccggatg cttctgtcaa cttctcagag     120
ttctccaaga agtgctcaga gaggtggaag accatgtctg ctaaagaaaa ggggaaattt    180
gaagatatgg caaggctga caaggctcgt tatgaaagag aaatgaaaac ctacatcccc     240
cccaaagggg agaccaaaaa gaagttcaag gaccccaatg cccccaagag gccttccttcg   300 gccttcttct tgttctgttc tgagtaccgc ccaaaaatca aggcgagca tcctggctta    360 tccattggtg atgttgcgaa gaaactagga gagatgtgga acaacactgc tgcggatgac   420
aagcagccct atgaaaagaa ggccgccaag ctgaaggaga gtatgagaa ggatattgct    480 gcctacagag ctaaggaaa acctgatgca gcgaaaaagg gggtggtcaa ggctgagaag    540
agcaagaaaa agaaggaaga ggaagacgac gaggaggatg aagaggatga ggaagaggag   600
gaagaggagg aagacgaaga tgaagaagaa gatgatgatg atgaataa                648

<210> SEQ ID NO 7
<211> LENGTH: 5
<212> TYPE: PRT
<213> ORGANISM: Artificial
<220> FEATURE:
<223> OTHER INFORMATION: fragment added to the expressed protein or
      peptides

<400> SEQUENCE: 7

Gly Pro Gly Tyr Gln
 1               5

<210> SEQ ID NO 8
<211> LENGTH: 60
<212> TYPE: DNA
```

```
<213> ORGANISM: Artificial
<220> FEATURE:
<223> OTHER INFORMATION: nucleotide sequence of cloning site of the
      pCAGGS vector
<220> FEATURE:
<221> NAME/KEY: CDS
<222> LOCATION: (1)..(60)

<400> SEQUENCE: 8 cat cac cat cac cat cac tcc gcg gct ctt gaa gtc ctc ttt cag gga      48
His His His His His His Ser Ala Ala Leu Glu Val Leu Phe Gln Gly
1               5                   10                  15 ccc ggg tac cag                                                      60
Pro Gly Tyr Gln
            20

<210> SEQ ID NO 9
<211> LENGTH: 20
<212> TYPE: PRT
<213> ORGANISM: Artificial
<220> FEATURE:
<223> OTHER INFORMATION: amino acid sequence of cloning site of the
      pCAGGS vector

<400> SEQUENCE: 9

His His His His His His Ser Ala Ala Leu Glu Val Leu Phe Gln Gly
1               5                   10                  15

Pro Gly Tyr Gln
            20

<210> SEQ ID NO 10
<211> LENGTH: 63
<212> TYPE: DNA
<213> ORGANISM: Artificial
<220> FEATURE:
<223> OTHER INFORMATION: artificial nucleotide sequence coding secretory
      signal sequence

<400> SEQUENCE: 10
atggagacag acacactcct gctatgggta ctgctgctct gggttccagg ttccactggt      60
gac                                                                   63

<210> SEQ ID NO 11
<211> LENGTH: 14
<212> TYPE: PRT
<213> ORGANISM: Artificial
<220> FEATURE:
<223> OTHER INFORMATION: artificial 6xHis-tag and TEV protease
      recognition site

<400> SEQUENCE: 11

Met Lys His His His His His His Glu Asn Leu Tyr Phe Gln
1               5                   10

<210> SEQ ID NO 12
<211> LENGTH: 6
<212> TYPE: PRT
<213> ORGANISM: Artificial
<220> FEATURE:
<223> OTHER INFORMATION: 6xHis-tag

<400> SEQUENCE: 12

His His His His His His
1               5

<210> SEQ ID NO 13
```

```
<211> LENGTH: 7
<212> TYPE: PRT
<213> ORGANISM: Artificial
<220> FEATURE:
<223> OTHER INFORMATION: TEV protease recognition site

<400> SEQUENCE: 13

Glu Asn Leu Tyr Phe Gln Gly
1               5

<210> SEQ ID NO 14
<211> LENGTH: 228
<212> TYPE: PRT
<213> ORGANISM: Artificial
<220> FEATURE:
<223> OTHER INFORMATION: recombinant hsHMGB1 with
      6xHis-tag and TEV protease
      recognition site

<400> SEQUENCE: 14

Met Lys His His His His His Glu Asn Leu Tyr Phe Gln Gly Lys
1               5                   10                  15

Gly Asp Pro Lys Lys Pro Arg Gly Lys Met Ser Ser Tyr Ala Phe Phe
            20                  25                  30

Val Gln Thr Cys Arg Glu Glu His Lys Lys His Pro Asp Ala Ser
        35                  40                  45

Val Asn Phe Ser Glu Phe Ser Lys Lys Cys Ser Glu Arg Trp Lys Thr
    50                  55                  60

Met Ser Ala Lys Glu Lys Gly Lys Phe Glu Asp Met Ala Lys Ala Asp
65                  70                  75                  80

Lys Ala Arg Tyr Glu Arg Glu Met Lys Thr Tyr Ile Pro Pro Lys Gly
                85                  90                  95

Glu Thr Lys Lys Lys Phe Lys Asp Pro Asn Ala Pro Lys Arg Pro Pro
                100                 105                 110

Ser Ala Phe Phe Leu Phe Cys Ser Glu Tyr Arg Pro Lys Ile Lys Gly
            115                 120                 125

Glu His Pro Gly Leu Ser Ile Gly Asp Val Ala Lys Lys Leu Gly Glu
    130                 135                 140

Met Trp Asn Asn Thr Ala Ala Asp Asp Lys Gln Pro Tyr Glu Lys Lys
145                 150                 155                 160

Ala Ala Lys Leu Lys Glu Lys Tyr Glu Lys Asp Ile Ala Ala Tyr Arg
                165                 170                 175

Ala Lys Gly Lys Pro Asp Ala Ala Lys Lys Gly Val Val Lys Ala Glu
            180                 185                 190

Lys Ser Lys Lys Lys Lys Glu Glu Glu Glu Asp Glu Glu Asp Glu Glu
            195                 200                 205

Asp Glu Glu Glu Glu Asp Glu Glu Asp Glu Asp Glu Glu Glu Asp
    210                 215                 220

Asp Asp Asp Glu
225
```